United States Patent
Reese et al.

(10) Patent No.: US 10,959,644 B2
(45) Date of Patent: Mar. 30, 2021

(54) COMPLIANT SENSORS FOR FORCE SENSING

(71) Applicant: Bend Labs, Inc., Salt Lake City, UT (US)

(72) Inventors: Shawn P. Reese, Salt Lake City, UT (US); Jared K. Jonas, Seattle, WA (US); Colton Allen Ottley, Farmington, UT (US); Garvin Tran, South Jordan, UT (US); Nathan Briggs, Salt Lake City, UT (US)

(73) Assignee: Bend Labs Inc., Salt Lake City, UT (US)

( * ) Notice: Subject to any disclaimer, the term of this patent is extended or adjusted under 35 U.S.C. 154(b) by 707 days.

(21) Appl. No.: 15/467,978

(22) Filed: Mar. 23, 2017

(65) Prior Publication Data
US 2017/0273599 A1   Sep. 28, 2017

Related U.S. Application Data

(60) Provisional application No. 62/313,048, filed on Mar. 24, 2016.

(51) Int. Cl.
*A61B 5/103*   (2006.01)
*G01L 1/14*    (2006.01)
(Continued)

(52) U.S. Cl.
CPC .......... *A61B 5/1038* (2013.01); *A61B 5/0004* (2013.01); *A61B 5/6807* (2013.01);
(Continued)

(58) Field of Classification Search
CPC ... A61B 5/1036; A61B 5/1038; A61B 5/6807; A61B 2562/0247; A61B 2562/0261;
(Continued)

(56) References Cited

U.S. PATENT DOCUMENTS 4,437,138 A   3/1984 Nicol
4,442,606 A   4/1984 Graham et al.
(Continued)

FOREIGN PATENT DOCUMENTS

EP   0287149 A2   10/1988

OTHER PUBLICATIONS

International Search Report and Written Opinion dated Jul. 1, 2016, on application No. PCT/US2016/027711.
(Continued)

*Primary Examiner* — Devin B Henson
(74) *Attorney, Agent, or Firm* — Parsons Behle & Latimer

(57) ABSTRACT

Disclosed is a first force sensing region of footwear. The first force sensing region includes a first force sensor unit. The first force sensor unit includes a first compliant capacitor disposed with respect to a first plane. The first force sensor unit also includes a strain transformation structure disposed with respect to the first plane. The strain transformation structure includes a first transformation element coupled to an outer surface of the first electrode of the first compliant capacitor and a second transformation element coupled to an outer surface of the second electrode of the first compliant capacitor.

18 Claims, 36 Drawing Sheets

(51) Int. Cl.
*A61B 5/00* (2006.01)
*A43B 3/00* (2006.01)
*A61B 90/00* (2016.01)

(52) U.S. Cl.
CPC .............. *G01L 1/142* (2013.01); *G01L 1/146* (2013.01); *A43B 3/0005* (2013.01); *A61B 2090/064* (2016.02); *A61B 2090/065* (2016.02); *A61B 2562/0247* (2013.01); *A61B 2562/0261* (2013.01); *A63B 2220/50* (2013.01); *A63B 2220/51* (2013.01); *A63B 2220/56* (2013.01)

(58) Field of Classification Search
CPC .............. A43B 3/0005; A63B 2220/50; A63B 2220/51; A63B 2220/56; G01L 1/142; G01L 1/146
See application file for complete search history.

(56) References Cited

U.S. PATENT DOCUMENTS

| | | | |
|---|---|---|---|
| 4,542,291 A | 9/1985 | Zimmerman | |
| 4,897,927 A | 2/1990 | Nicol | |
| 4,944,181 A | 7/1990 | Wnuk | |
| 4,994,181 A | 2/1991 | Mullaney, Jr. | |
| 5,047,719 A | 9/1991 | Johnson et al. | |
| 5,047,952 A | 9/1991 | Kramer et al. | |
| 5,086,785 A | 2/1992 | Gentile et al. | |
| 5,583,476 A | 12/1996 | Langford | |
| 5,610,528 A | 3/1997 | Neely et al. | |
| 5,809,462 A | 9/1998 | Nussbaum | |
| 6,127,672 A | 10/2000 | Danisch | |
| 6,389,187 B1 | 5/2002 | Greenaway et al. | |
| 6,575,041 B2 | 6/2003 | Schwarz et al. | |
| 6,724,359 B2 | 4/2004 | Yamamoto et al. | |
| 6,809,462 B2 | 10/2004 | Pelrine et al. | |
| 7,249,422 B2 | 7/2007 | Bergamasco et al. | |
| 7,373,721 B2 | 5/2008 | Bergamasco et al. | |
| 7,395,717 B2* | 7/2008 | DeAngelis ............... G01L 1/146 73/724 | |
| 7,661,309 B2 | 2/2010 | Lan et al. | |
| 7,958,789 B2 | 6/2011 | Hayakawa et al. | |
| 7,984,659 B2 | 7/2011 | Fujimoto et al. | |
| 8,063,631 B2 | 11/2011 | Fermon et al. | |
| 8,232,797 B2 | 7/2012 | Decitre | |
| 8,384,398 B2 | 2/2013 | Laflamme et al. | |
| 8,410,932 B2 | 4/2013 | Van Gastel | |
| 8,451,011 B2 | 5/2013 | Hayakawa et al. | |
| 8,866,472 B2 | 10/2014 | Decitre et al. | |
| 8,941,392 B1 | 1/2015 | Reese | |
| 9,113,663 B2 | 8/2015 | Stern | |
| 9,125,595 B2* | 9/2015 | Clarke ............... A61B 5/1038 | |
| 9,222,764 B2 | 12/2015 | Reese | |
| 9,476,692 B2 | 10/2016 | Reese | |
| 10,451,493 B2* | 10/2019 | Mathieu ............... G01L 5/165 | |
| 2002/0088931 A1 | 7/2002 | Danisch et al. | |
| 2005/0007106 A1 | 1/2005 | Goldfine et al. | |
| 2005/0101887 A1 | 5/2005 | Stark et al. | |
| 2006/0015191 A1 | 1/2006 | Bergamasco et al. | |
| 2006/0130347 A1 | 6/2006 | Bergamasco et al. | |
| 2008/0007253 A1 | 1/2008 | Takahata | |
| 2008/0034883 A1 | 2/2008 | Majeti | |
| 2009/0015270 A1 | 1/2009 | Hayakawa et al. | |
| 2009/0085444 A1 | 4/2009 | Alvarez Icaza Rivera et al. | |
| 2009/0206831 A1 | 8/2009 | Fermon et al. | |
| 2010/0033196 A1 | 2/2010 | Hayakawa et al. | |
| 2010/0063779 A1 | 3/2010 | Schrock et al. | |
| 2010/0078999 A1 | 4/2010 | Celenza et al. | |
| 2010/0101329 A1 | 4/2010 | Berris, Jr. | |
| 2010/0109658 A1 | 5/2010 | Decitre | |
| 2010/0286950 A1 | 11/2010 | Heijkants et al. | |
| 2011/0232390 A1 | 9/2011 | Matsumoto et al. | |
| 2012/0019239 A1 | 1/2012 | Decitre | |
| 2012/0078999 A1 | 3/2012 | Andrew et al. | |
| 2012/0220904 A1 | 8/2012 | Warren | |
| 2012/0277531 A1 | 11/2012 | Krattiger et al. | |
| 2013/0150755 A1* | 6/2013 | Kubiak ............... A61B 5/1036 600/592 | |
| 2014/0200486 A1* | 7/2014 | Bechtel ............... A61B 5/14551 600/592 | |
| 2015/0054527 A1 | 2/2015 | Reese | |
| 2015/0330855 A1* | 11/2015 | Daniecki ............... A43B 3/0005 73/727 | |
| 2016/0305759 A1 | 10/2016 | Reese et al. | |
| 2017/0074637 A1 | 3/2017 | Reese | |
| 2017/0086704 A1* | 3/2017 | Gwin ............... A61B 5/742 | |
| 2018/0078176 A1* | 3/2018 | Seitz ............... A61B 5/6887 | |

OTHER PUBLICATIONS

Pelrine, Ronal E. et al., "Electrostriction of polymer dielectrics with compliant electrodes as a means of actuation", Sensors and Actuators A 64, Jan. 1998, pp. 77-85, Published by Elsevier Sciences S.A.
International Search Report and Written Opinion dated Feb. 23, 2016, on application No. PCT/US2014/051535.
Bose, Dr. Holger "Highly flexible mechanical sensors made of dielectric elastomers" Fraunhofer Institute for Silicate Research ISC, 2014 www.isc.Fraunhofer.de (2 pages).
Engel, Jonathan M., et al. "Multi-layer Embedment of Conductive and Non-Conductive PDMS for All-Elastomers MEMS" The 12th Solid State Sensors, Actuator, and Microsystem workshop, Hilton Head Island, SC, Jun. 2006 (4 pages).
Lipomi, Darren J., et al. "Skin-like pressure and strain sensors based on transparent elastic films of carbon nanotubes" Nature Nanotechnology Oct. 2011 (5 pages).
Cai, Lee, et al. "Super-stretchable, Transparent Carbon Nanotibe-Based Capacitive Strain Sensors for Juman Motion Detection" Scientific Reports, Oct. 2013 (9 pages).
Cohen, Daniel J., et al. "A Highly Elastic, Capacitive Strain Gauge Based on Percolating Nanotube Networks" American Chemical Society, Nano Letter, Mar. 2012 (5 pages).
Yao, Shanshan and Yong, Zhu "Wearable multifunctional sensors using printed stretchable conductors made of silver nanowires" Royal Society of Chemistry, Dec. 2013 (8 pages).
International Search Report and Written Opinion dated Jun. 9, 2017, on application No. PCT/US2017/024086.

* cited by examiner

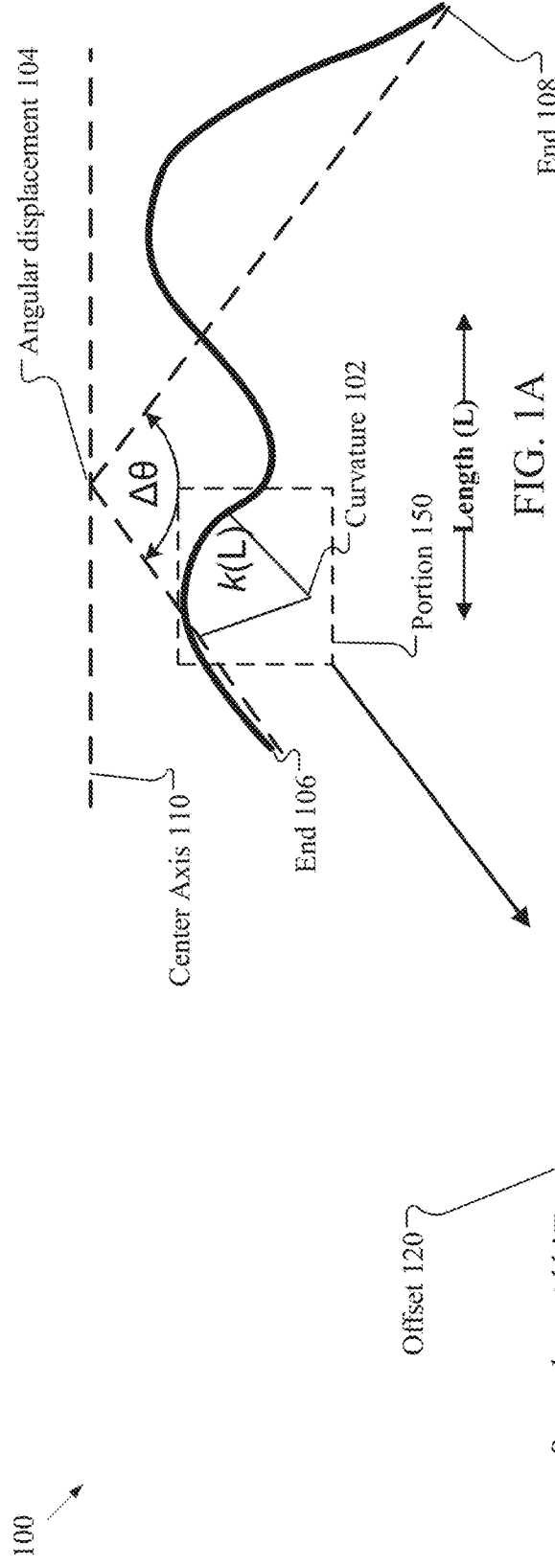
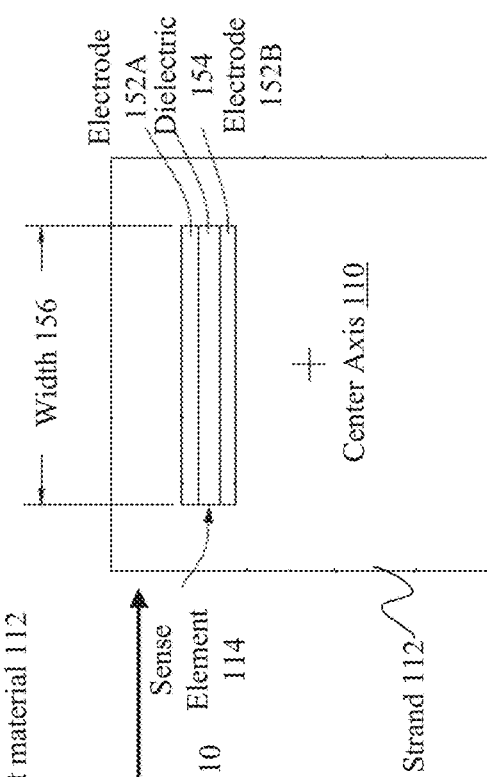
FIG. 1A
FIG. 1B
FIG. 1C

COMPLIANT SENSORS FOR FORCE SENSING

RELATED APPLICATIONS

This application claims the benefit of U.S. Provisional Application No. 62/313,048, filed Mar. 24, 2016, and entitled "Elastomeric Capacitor Networks for Sensing and Actuation," the entire contents of which are incorporated herein by reference.

BACKGROUND

Sensors for detecting, measuring, monitoring, or actuating physical phenomena are ubiquitous in the field of engineering. Some sensors may provide a corresponding output responsive to detecting, measuring, or monitoring physical phenomena. A variety of sensors exist and include temperature sensors, pressure sensors, ultrasonic sensors, strain sensors, light sensors, flex and bend sensors, angular displacement sensors, compressive force sensors, among others. Sensors may use different types of sense elements, such as capacitive sense elements, resistive sense elements, photonic sense elements, or others types of sense elements, to sense or actuate physical phenomena.

BRIEF DESCRIPTION OF THE DRAWINGS

The present disclosure is illustrated by way of example, and not by way of limitation, in the figures of the accompanying drawings.

FIG. 1A is an illustration of a simplified angular displacement unit, in accordance with some embodiments.

FIG. 1B is an illustration of a portion of the simplified angular displacement unit of FIG. 1A, in accordance with some embodiments.

FIG. 1C is an illustration of a cross sectional view of the simplified angular displacement unit of FIG. 1B, in accordance with some embodiments.

DETAILED DESCRIPTION

Sensor systems measure and actuate a variety of physical phenomena. Many applications appreciate, or even demand, sensors having sense capabilities and the ability to move or deform with one, two, or three rotational degrees of freedom. For example, wearable sensor systems may integrate with an object, such as a human body, to measure physical phenomena (such as, joint angles) or to actuate physical phenomena (such as, heat, vibration, or light). Wearable systems may also be robust to destructive forces (such as shear forces), malleable enough to move, pull, compress, twist or bend, or resistant to environmental elements (such as water or salt). Such types of sensor systems present significant challenges.

Embodiments described herein address the above mentioned and other challenges by using a variety of compliant sensors, such as angular displacement sensors, strain sensors, compressive force sensors, haptic actuator sensor, as well as others. Various configurations and embodiments described herein of the compliant sensors address at least the above challenges as well as others.

For example, in one embodiment, a system includes an insole of footwear with a first force sensing region. The first force sensing region includes a first force sensor unit at least partially embedded in the insole. The force sensor unit includes a first compliant capacitor disposed with respect to a first plane. The force sensor unit includes a strain transformation structure disposed with respect to the first plane. The strain transformation structure includes a first transformation element coupled to an outer surface of the first electrode of the first compliant capacitor. The second transformation element is coupled to an outer surface of the second electrode of the first compliant capacitor. A compressive force perpendicular to the first plane applied to the strain transformation structure by a human foot induces a substantially linear change in a capacitance of the first compliant capacitor. The capacitance of the first compliant capacitor is indicative of the compressive force applied by the human foot to the first force sensing region of the insole.

In some embodiments, the compressive force perpendicular to the first plane and applied to the strain transformation structure induces a deformation of a surface of the strain transformation structure that is parallel to the first plane. The deformation of the strain transformation structure is substantially linear to the compressive force and induces a substantially linear change in area of the first compliant capacitor.

Figure 2:
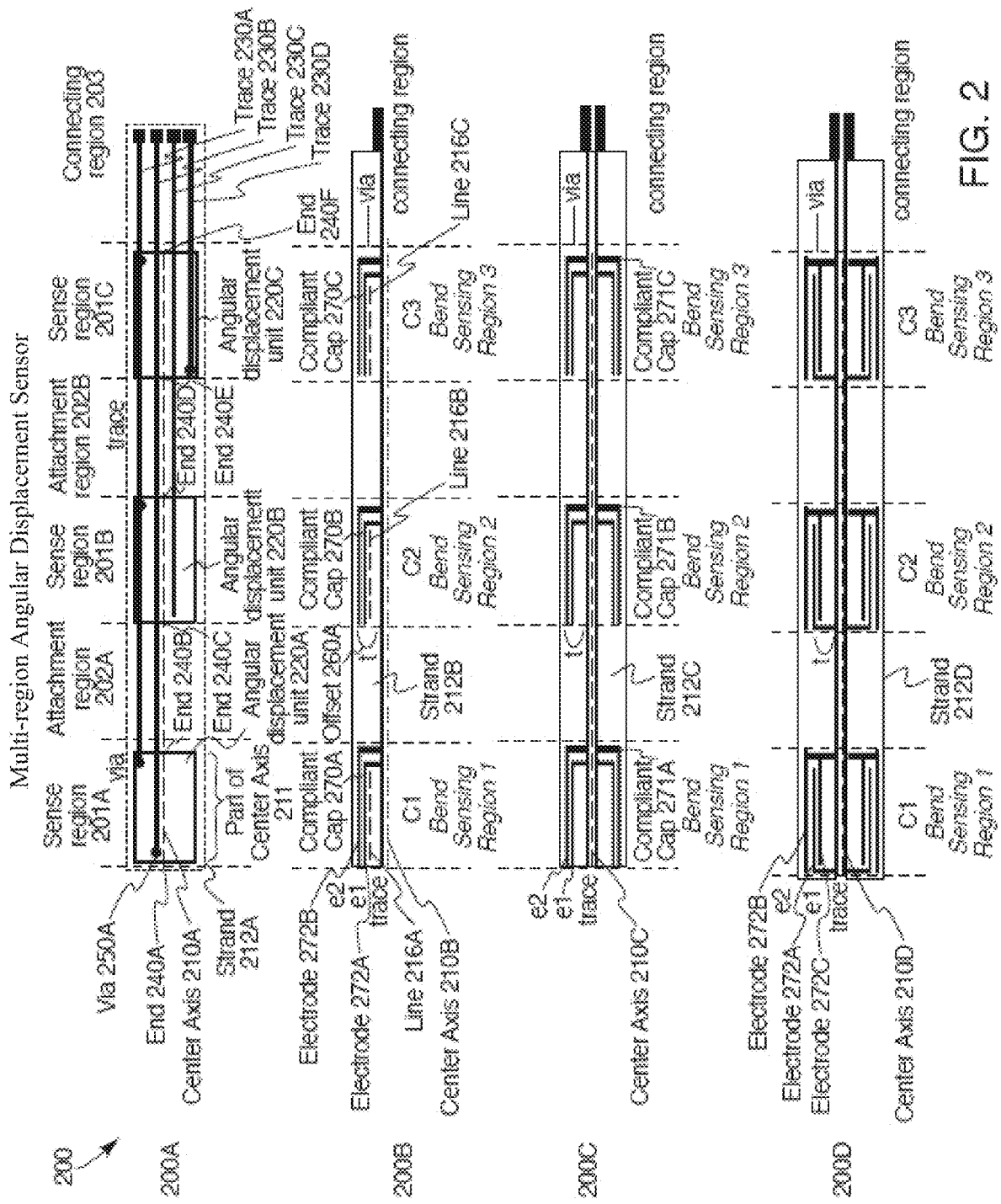
FIG. 2 illustrates different configurations of a multi-region angular displacement sensor, in accordance with some embodiments.
Figure 3:
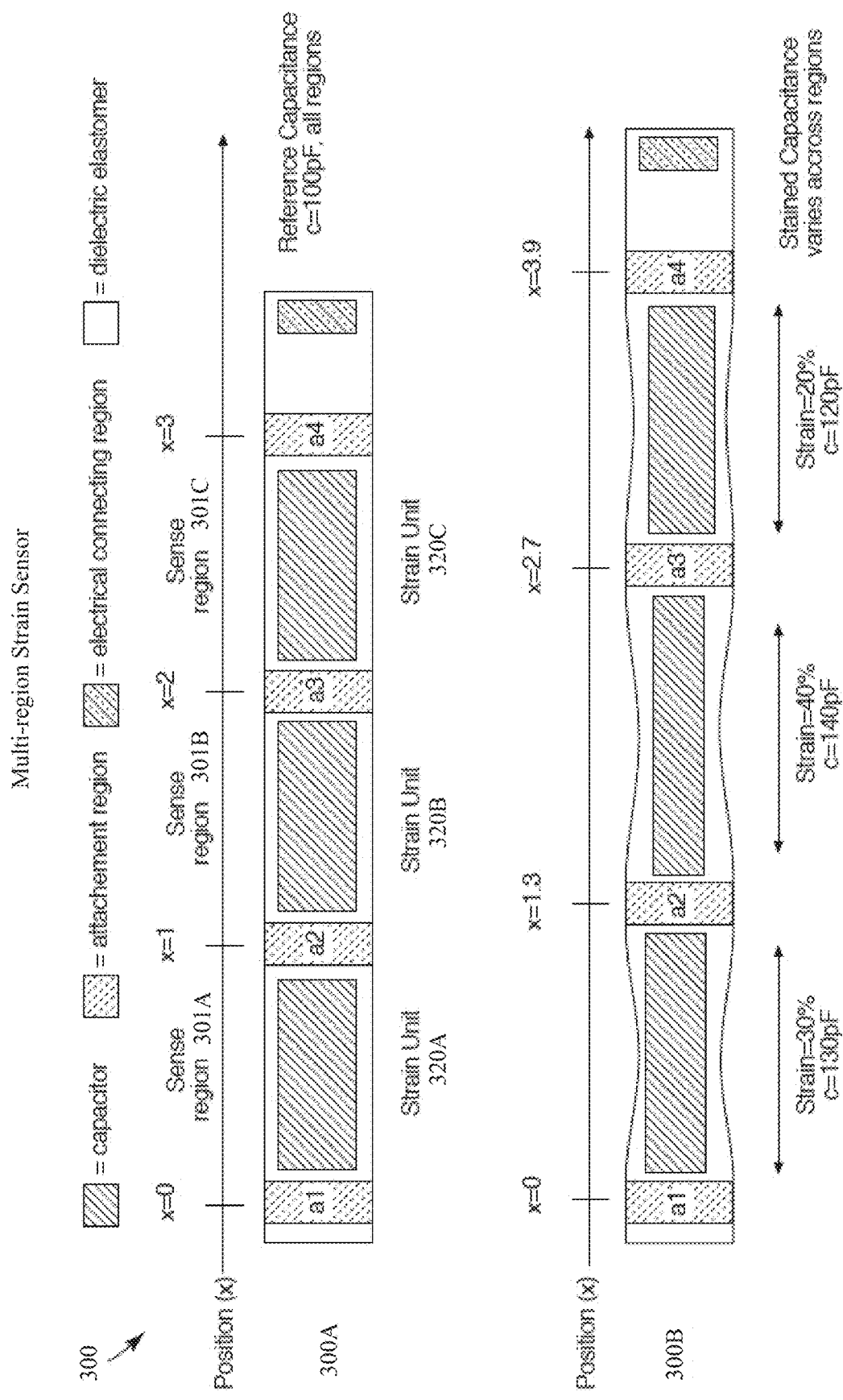
FIG. 3 is an illustration of a multi-region strain sensor, in accordance with some embodiments.

It may be noted that FIGS. 1-3 describe at least embodiments of compliant angular displacement sense units, compliant strain units, and compliant multi-region sensors. FIGS. 4-17 describe at least embodiments of compliant force sensor units and applications, such as footwear. FIG. 18 describes at least embodiments of haptic sense elements. FIGS. 19-26 describe at least embodiments of tape sensors. FIGS. 27-34 describe at least embodiments of wearable sensors It may be noted that elements and features described herein, may be combined in multiple ways or used with different features or elements than described herein. It may also be noted that elements and features described herein, may be applied to different applications than described herein. In some embodiments, a sensor may at least include a sense element, such as a compliant capacitor.

FIG. 1A is an illustration of a simplified angular displacement unit, in accordance with some embodiments. Angular displacement unit 100 is illustrated with end 106 and end 108. The angular displacement unit 100 is stretchable between end 106 and end 108 and bendable along a length (L) of the angular displacement unit 100 in any direction in a three-dimensional space. For example, angular displacement unit 100 may behave similarly to a rubber band. Angular displacement unit 100 may stretch and bend along multiple points along the length. At any point along the length, angular displacement unit 100 may bend at 90 degrees or greater in any direction in three-dimensional space. For example, angular displacement unit 100 may be folded onto itself multiple times and/or twisted, while maintaining electrical connectivity such that the electrodes of the angular displacement unit 100 maintain electrical connection and the capacitance of angular displacement unit 100 may be measured. It may be noted that the deformation and connectivity properties described with respect to angular displacement unit 100, may also be applied to other elements, such as sense elements, sense units, or multi-region sensors, described herein, unless otherwise described.

Angular displacement 104 (also referred to as "bend" herein) may be a change in angle (i.e., $\Delta(\Theta)$) relative to an axis, such as center axis 110, or a center plane (i.e., a plane that intersects the center axis 110 and is coplanar to the width of the angular displacement unit 100). It may be noted that center axis 110, as illustrated in FIG. 1A, shows the center axis 110 when angular displacement unit 100 is in a linear and non-bent position. Center axis 110 of angular displacement unit 100 will curve or bend as angular displacement unit 100 curves and bends, as illustrated in FIG. 1B.

In embodiments, the curvature 102, k(L), varies along the length (L) of the angular displacement unit 100 (e.g., where length (L) extends from end 106 to the other end 108). In embodiments, angular displacement 104 may be determined by integrating the curvature 102, k(L), along the length (L) of the angular displacement unit 100 to generate a value indicative of a change in the angular displacement 104 (i.e. $\Delta(\Theta)$). In embodiments, extraneous bending of the angular displacement unit 100 may not impact the measurement of angular displacement 104 of the ends 106 and 108 (also referred to as sensor ends), as the extraneous positive curvature may cancel out the extraneous negative curvature along the length (L) of angular displacement unit 100.

In embodiments, center axis 110 may an arbitrary axis that is defined relative to the one or more sense elements (e.g., sense element 114 of FIG. 1B) (also referred to as "sensing elements") of angular displacement unit 100. For example, when angular displacement unit 100 is in a linear and non-bent position, angular displacement unit 100 aligns with center axis 110. Center axis 110 may be positioned at some location relative to the sense elements of angular displacement unit 100, as illustrated in FIG. 1B.

In embodiments, end 106 and end 108 may define two respective vectors of angular displacement unit 100. In embodiments, the two vectors may define the angular displacement 104. A vector may be a line from a first point where the center axis intersects a first plane at the end of the angular displacement unit 100, where the first plane is perpendicular to the center axis, and through a second point an infinitesimal distance away from the end of angular displacement unit 100 that is contained within a second plane, where the second plane is orthogonal to the first plane and runs through the center axis by bisecting a sense element of angular displacement unit 100 sensor along the length of the sense element.

FIG. 1B is an illustration of a portion 150 of the simplified angular displacement unit 100 of FIG. 1A, in accordance with some embodiments. FIG. 1C is an illustration of a cross sectional view of the simplified angular displacement unit of FIG. 1B, in accordance with some embodiments. Angular displacement unit 100 may include one or more sense elements, such as sense element 114. In another embodiment, angular displacement unit 100 may include another sense element (not shown) offset from center axis 110 in a −Z direction and orientated parallel to sense element 114. In one embodiment, sense element 114 is compliant capacitor, such as an elastomeric capacitor, as illustrated in FIG. 1C. In one embodiment, sense element 114 may include of three layers of elastomer, electrode 152A (also referred to as "electrode layer" herein), dielectric 154 (also referred to as "dielectric layer" herein), and electrode 152B. In embodiments, electrode 152A and 152B may each be a compliant or elastomeric electrode layer made from conductive filler such as, a conductive carbon nanotube or elastomer composite. The conductive filler may maintain conductivity at small and large deformations responsive to small and large strains. In embodiments, between the two electrode layers 152A and 152B may be a non-conducting compliant dielectric layer 154. In embodiments, the capacitance of the compliant capacitor may be approximated as a parallel plate capacitor using the following equation:

$$c = \frac{k\varepsilon_0 A}{D}$$

C is capacitance, k is relative permittivity, $\varepsilon_0$ is the permittivity of free space, A is the area of the electrodes, and D is the thickness of the dielectric.

Strain and stretch describe how things elastically deform. Strain ($\ominus$) may be described as $$\frac{l - L_0}{L_0},$$

where l is the total length of deformed material and $L_0$ is the length of the undeformed material. Stretch ($\lambda$) may be described as $$\frac{l}{L_0}.$$

The term strain may be used to describe small deformation (e.g., metal rod under tension), while stretch may be used to describe a larger deformation (e.g., rubber band under tension). Strain may be a three-dimensional measure ($\varepsilon_x$, $\varepsilon_y$, $\varepsilon_z$) or a one-dimensional value, where strain is measured along an axis of tensile strain. In tension, strain is positive. In compression, strain is negative. Stretch and strain may be used synonymously herein, unless otherwise described. When in tensile stretch ($\lambda$) and assuming Poisson's ratio of 0.5 (as elastomers a relatively incompressible), the following capacitance-strain relationship may be described in the following equation:

$$c(\lambda) = c_0 \lambda$$

$c_0$ is the capacitance in the unstrained state, $\lambda$ is stretch (or strain) as defined above, and $c(\lambda)$ is the capacitance under strain. It may be noted that $c(\lambda)$ is linear function of strain and is valid for both small and large strains (i.e., for both strain and stretch as defined above).

In one embodiment, angular displacement unit 100 may include sense element 114 embedded within strand 112 (also referred to as "strand of compliant material", "body", "elongated body"), such that the sense element 114 is offset 120 a distance Z from center axis 110 of strand 112. In some embodiments, strand 112 may be a compliant material, such as an elastomeric matrix. It may be noted that in other embodiments, sense element 114 may be partially embedded in the strand 112 or connected to strand 112 (e.g., connected to an outer surface of strand 112). Offset 120 may be a distance Z from the center axis 110. When the angular displacement unit 100 is bent, a curvature 102 (i.e., k (L)) may be induced in the sense element 114. The curvature may result in a positive tensile strain, $\varepsilon_t$, in sense element 114 on the outside (located a distance +Z form the center axis 110) and in a negative compressive strain, $\varepsilon_c$, on the sense element (not shown) on the inside (located a distance −Z from the center axis 110). For small values of Z relative to the curvature, the curvature may be linearly related to the strain in the sense element 114 and estimated by the equation (units are 1/distance):

$$k = \frac{\varepsilon_t - \varepsilon_c}{2z}$$

It may be noted that the above equation may be used when an angular displacement unit 100 includes two coplanar compliant capacitor offset and reflected about a center axis 110 or center plane. For an angular displacement unit 100 with one compliant capacitor offset and reflected about a center axis 110 or center plane the negative compressive strain, $\varepsilon_c$, may be removed from the equation.

In embodiments, a deformation may refer to any change in size or shape of an object, such as an angular displacement unit 100, due to an applied force from another object. The deformation energy may be transferred through work rather than by heat, chemical reaction, moisture, etc. In one example, the deformation may be from a tensile force (e.g., pulling), a compressive force (e.g., pushing), shear force, bending force, and/or torsional force (e.g., twisting).

Although one sense element 114 is illustrated in FIG. 1B, two or more sense elements may be used in an angular displacement unit 100 in some embodiments. In one example, using two sense elements in parallel and reflected about center axis 110 may reduce common mode noise and/or increase the signal to noise ratio. In embodiments, when two or more sense elements orientated parallel are used in an angular displacement unit 100 a differential capacitance measurement may be made. For example, the difference between two separate capacitance measurements may be a differential capacitance measurement. In another example, the sense element 114 may share a ground plane (e.g., relative ground potential) with another sense element, and the difference between two separate capacitance measurements may be a differential capacitance measurement. In some embodiments, by connecting one or more additional sense elements in strand 112 perpendicular to sense element 114, angular displacement unit 100 may measure angular displacement in two orthogonal planes and any point within the two orthogonal planes. In other embodiments, additional sense elements in the strand 112 may be in a position other than perpendicular to sense element 114 so that angular displacement unit 100 may measure the angular displacement 104 about other planes. In some embodiments, connecting a one or more sense elements in a helical fashion about a center axis 110 may allow for the measuring of torsion about the center axis 110. It may be noted that although sense element 114 is described as a parallel plate capacitive sense element, in other embodiments, sense element may be a different type of sense element. In embodiments, width 156 is the width of sense element 114. In other embodiments, the width may be smaller or larger (e.g., extend the width of strand 112).

FIG. 1C shows a cross-sectional view (into the page) of angular displacement unit 100, in embodiments, sense element 114 may be a compliant capacitor including at least two electrodes 152A and 152B (e.g., compliant electrodes) with a compliant dielectric 154 disposed between the two electrodes 152. In embodiments, the electrodes 152 and compliant dielectric may run down the length (L) (e.g., from end 106 to end 108) of angular displacement unit 100. In embodiments, sense element 114 may be a parallel plate compliant capacitor. In some embodiments, sense element 114 may have two or more electrodes, where one or both of the outermost electrodes are coupled to a ground voltage potential. In embodiments, the outermost electrodes of sense element 114 having two or more electrodes may be coupled to a ground voltage material to act as shielding from parasitic capacitance, electric fields, or other undesirable phenomenon. In embodiments, the electrodes 152 may also define a thickness or depth (e.g., Z direction) such that the two electrodes 152 of compliant capacitors may include a similar thickness or depth in the range of about 10-500 microns. In embodiments, the compliant dielectric 154 disposed between the electrodes may define a thickness or depth of about 10 to 200 microns. In embodiments, the strand 112 of compliant material may include a depth in the range of about 0.5-8 mm or greater.

In embodiments, the electrodes 152 of the compliant capacitor may be a partially conductive material (and an elastomer based material) so as to conduct a charge or current. In embodiments, the compliant dielectric 154 between the electrodes may be non-conductive or slightly conductive (e.g., less conductive than the electrodes) and formed of a similar material as the strand 112. In embodiments, the electrodes 152 may be formed along as layers of an elastomer based material with conductive filler, as conductive or metal nano particles. The nano particles may include carbon nanotubes, carbon nanofibers, nickel nanostrands, silver nanowires, carbon black, graphite powder, graphene nano platelets, and/or other nano particles. In another embodiment, the conductive filler may be a micro particle of the same or similar material as the nano particle. In one embodiment, the electrodes 152 of the compliant sense element 114 may be manufactured using ion embodiment of the conductive filler to embed the nano particles, for example, into an elastomer.

In one embodiment, a minimum amount of conductive filler particles is used, as excess filler concentrations may alter the elastic behavior of the elastomer. Excessive conductive filler particles may limit the ability of the angular displacement unit 100 to effectively bend and result in an electrical circuit break through bending the angular displacement unit 100. Furthermore, intrinsically conductive elastomers or other compliant materials may be used, such as ionogels and elastomer or polymers with free charge carriers or similar, in some embodiments.

In embodiments, the strand 112 (e.g., elastomeric matrix) may be a thermoset or thermoplastic elastomer. In other embodiments, the strand 112 may be a dielectric material and non-conductive. In embodiments, strand 112 may include structural characteristics of high elongation at failure greater than 20% and preferably greater than 500%, a low durometer preferably at a 60 Shore A scale, but may be anywhere in the range of 1-90 on the Shore A scale. In some embodiments, strand 112 may include a low compression set of 1-30%. In an embodiment, a thermoset elastomer may include tin or platinum cured silicone elastomers and/or polyurethane elastomer components or any other suitable elastomer material. In another embodiment, a thermoplastic elastomer may include components of styrene-ethylene/butylene-styrene (SEBS), styrene-block-butadiene-block-styrene (SBS), and/or polyurethanes or any other suitable thermoplastic elastomer. In still other embodiments, sense element may be used without strand 112.

FIG. 2 illustrates different configurations of a multi-region angular displacement sensor, in accordance with some embodiments. Multi-region angular displacement sensor 200 includes several views of multi-region angular displacement sensors with different configurations. In embodiments, multi-region angular displacement sensor 200 may include multiple sensing regions 201 where the multiple sensing regions 201 include angular displacement units 220, similar to angular displacement unit 100 described with respect to FIG. 1A-C. In embodiments, each sensing region 201 may be used to sense angular displacement independent from other sensing regions 201.

It should be noted that features that are described with respect to multi-region angular displacement sensor 200 apply to multi-region angular displacement sensor 200A-200D, unless otherwise described. Multi-region angular displacement sensor 200 illustrates a top view of multi-region angular displacement sensor 200A, a cross section of a side view of multi-region angular displacement sensor 200B, another cross section of a side view of another multi-region angular displacement sensor 200C, and a cross section of a side view of still another multi-region angular displacement sensor 200D.

In embodiments, multi-region angular displacement sensor 200 (or strand 212A) has multiple sense regions 201 including sense region 201A, sense region 201B, and sense region 201C (also referred to as "sensing regions" herein). Although three sense regions are described, two or more sense regions may be included in multi-region angular displacement sensor 200. Sense region 201A includes angular displacement unit 220A, sense region 201B includes angular displacement unit 220B, and sense region 201C includes angular displacement unit 220C. It may be noted that for purposes of illustration, rather than limitation, all sense regions 201 are illustrated with angular displacement units 220. In other embodiments, some of sense regions 201 may contain other sense units, such as strain unit (as described with respect to FIG. 3), or force sensor unit, or torsional unit, a haptic actuator unit (e.g., includes at least one haptic actuator sense element), for example.

In embodiments, angular displacement units 220 include two ends 240, where each end defines a vector of angular displacement. Angular displacement unit 220A includes end 240A and 240B, angular displacement unit 220B includes end 240C and 240D, and angular displacement unit 220C includes end 240E and 240F. In embodiments, the vectors associated with ends 240 are defined with respect to the center axis 210 (also referred to as angular displacement axis). In embodiments, the vectors associated with ends 240 define angular displacement for the respective angular displacement units 220 or respective sense regions 201.

For purposes of illustration, rather than limitation, center axis 210 is illustrated as common to all the angular displacement units 220 of multi-region angular displacement sensor 200. For example, end 240A and end 240B of angular displacement unit 220A extend between part 211 of center axis 210A. The respective part 211 of the center axis 210A corresponding to the angular displacement unit 220A is the angular displacement axis for angular displacement unit 220A. The respective part of the center axis 210A corresponding to the angular displacement unit 220B is the angular displacement axis for angular displacement unit 220B. The respective part of the center axis 210A corresponding to the angular displacement unit 220C is the angular displacement axis for angular displacement unit 220C.

In other embodiments, center axis 210 may be distinct for one or more of angular displacement units 220 or distinct for one or more compliant capacitors (e.g., compliant capacitor 270) of an angular displacement unit 220. For example, one or more angular displacement units 220 may have a respective center axis (e.g., part of center axis) that is not common with the center axes of other angular displacement units 220. For example, angular displacement unit 220B may be rotated 90 degrees so that end 240C and end 240D are orientated vertically. The center axis associated with rotated angular displacement unit 220B may be at a 90 degree angle (or any other angle or orientation, for example) to center axis 210A.

Multi-region angular displacement sensor 200 may be connected to a strand 212 (e.g., strand 212A, 212B, 212C, and 212D) of compliant material, such as an elastomeric matrix. In one embodiment, multi-region angular displacement sensor 200 is embedded in strand 212. In another embodiment, multi-region angular displacement sensor 200 is partially embedded in strand 212. In still another embodiment, multi-region angular displacement sensor 200 is connected on an outer surface of strand 212.

In embodiments, sense regions 201 may be connected by respective attachment regions 202. For example, sense region 201A and sense region 201B are physically connected to attachment region 202A, sense region 201B and sense region 201C are physically connected to attachment region 202B. Attachment region may be of any material. In one embodiment, attachment region 202 may be stretchable and made of a compliant material, such as an elastomeric matrix. In another embodiment, attachment region may be made of a material that is inelastic or less elastic than strand 212A.

For purposes of illustration, rather than limitation, multi-region angular displacement sensor 200 is shown embedded in a single strand 212A of compliant material. However, it may be noted that other configurations may be implemented. For example, one or more angular displacement units 220 may be implemented on independent strands connected by attachment regions 202. Attachment region 202 may be any length starting from 0 centimeters. In some embodiments, attachment region 202 is not implemented.

In embodiments, each angular displacement unit 220 is connected to one or more traces 230. Angular displacement unit 220A is connected to trace 230A and 230B. Angular displacement unit 220B is connected to trace 230A and 203C. Angular displacement unit 220C is connected to trace 230A and 203D. In embodiments, traces 230 may be a compliant conductive material able to deform similarly to strand 212. In one embodiment, the traces 230 are made from an elastomer, similar to compliant capacitors 270. In another embodiment, traces 230 made from an elastomer but of a different composition than compliant capacitors 270. For example, traces 230 may use different conductive fillers and/or different amounts of conductive filler than compliant capacitors 270. In embodiments, traces 230 may be stretchable along the length of trace 230 while maintaining connectivity and conductivity. In embodiments, traces 230 may be bendable in any direction in a three-dimensional space and maintain connectivity and conductivity. In embodiments, traces 230 may be on the same plane as the electrodes of angular displacement unit 220, as illustrated by trace 203C connected to angular displacement unit 220B. In embodiments, traces 230 may be on a different plane than the electrodes of angular displacement unit 220, as illustrated by trace 230B connected to angular displacement unit 220A through via 250A.

In embodiments, additional vias are illustrated by black dots associated with multi-region angular displacement sensor 200A (e.g., via 250A) and vertical lines as illustrated with respect to multi-region angular displacement sensor 200B-200C. In embodiments, vias, such as via 250A, may be made from numerous materials, such as a compliant conductive material.

In embodiments, multi-region angular displacement sensor 200 may also include connecting region 203. In an embodiment, connecting region 203 may be an electrical connecting area or terminal area for one or more traces. In other embodiments, connecting region may be made of any material. In one embodiment, connecting region 203 is part of strand 212. In another embodiment, connecting region 203 may be a flexible or hard circuit board. In embodiments, connecting region 203 may connect multi-region angular displacement sensor 200 to other circuits, power, and/or other multi-region angular displacement sensors. In an embodiment, connecting region 203 may include electrode pads to facilitate an electrical connection.

In one embodiment, multi-region angular displacement sensor 200B illustrates a cross section of a side view of a multi-region angular displacement sensor 200. Multi-region angular displacement sensor 200B includes angular displacement units 220 that each include a compliant capacitor 270 offset 260A a distance "t" away from center axis 210B and along a line 216 (e.g., line 216A, line 216B, and line 216V) offset from center axis 210B. Angular displacement unit 220A of multi-region angular displacement sensor 200B includes a sense element, such as compliant capacitor 270A. Angular displacement unit 220B of multi-region angular displacement sensor 200B includes a sense element, such as compliant capacitor 270B. Angular displacement unit 220C of multi-region angular displacement sensor 200B includes a sense element, such as compliant capacitor 270C. In some embodiments, compliant capacitors 270 include two electrodes. For example, compliant capacitor 270A includes electrode 272A and electrode 272B with a dielectric interposed between. It may be noted that although angular displacement units 220 (and the compliant capacitor 270 of the angular displacement units 220) are illustrated as rectangles, angular displacement unit 220 and the associated compliant capacitors 270 may be circular, ellipsoidal, V-shaped, or any other shape.

In embodiments, in each sense region 201, a positive curvature will induce positive strain in the angular displacement unit 220 for the respective sense region 201 that will increase the capacitance for the compliant capacitor 270 in the respective sense region 201. The capacitance may be a linear function of angular displacement between the two vectors defined by the ends 240 of the respective angular displacement unit 220.

In embodiments, the angular displacement of each sense region 201 may be determined independent from the angular displacement of other sense regions 201. For example, a change in electrical characteristics of angular displacement unit 220A in response to deformation (e.g., a bend or angular displacement) of the strand 212A in the sense region 201A is independent from a change in electrical characteristics of the angular displacement unit 220B in response to deformation of the strand 212A in the sense region 201B and independent from a change in electrical characteristics of the angular displacement unit 220C in response to deformation of the strand 212A in the sense region 201C. The change in capacitance of compliant capacitor 270A (or electrical signal indicative of the capacitance) in response to a bend in sense region 201A is independent from the change in capacitance of compliant capacitor 270B and 270C associated with sense region 201B and 201C, respectively.

In embodiments, multi-region angular displacement sensor 200C shows a cross section of a side view of a multi-region angular displacement sensor 200. In one embodiment, each angular displacement unit 220 includes two compliant capacitors, compliant capacitor 270 and 271, reflected about center axis 210C. The first compliant capacitor 270 (see multi-region angular displacement sensor 200B) is offset 260A a distance 't' from center axis 210C. The second compliant capacitor 271 is offset a distance 't' from center axis 210C in the opposite direction. Angular displacement unit 220A of multi-region angular displacement sensor 200C includes compliant capacitor 270A and 271A. Angular displacement unit 220B of multi-region angular displacement sensor 200C includes compliant capacitor 270B and 271B. Angular displacement unit 220C of multi-region angular displacement sensor 200C includes compliant capacitor 270C and 271C. Compliant capacitors 271 include two electrodes. Multi-region angular displacement sensor 200C is illustrated as embedded in strand 212C.

In embodiments, sensitivity of a multi-region angular displacement sensor 200C may be increased by combining two compliant capacitors, such as compliant capacitor 270 and 271, reflected about center axis 210C. In one embodiment. reflecting compliant capacitor 270 and 271 about center axis 210C may help reject common mode signals resulting from noise and tensile strain. In each sense region 201, the difference in the capacitance between compliant capacitor 270 and 271 is proportional to the curvature of the respective sense region.

In an embodiment, multi-region angular displacement sensor 200D shows a cross section of a side view of a multi-region angular displacement sensor 200. Similar to multi-region angular displacement sensor 200C, each angular displacement unit 220 of multi-region angular displacement sensor 200D includes two compliant capacitors, compliant capacitor 270 and 271, reflected about center axis 210D. The compliant capacitors 270 and 271 of multi-region angular displacement sensor 200D include three electrodes, electrode 272A, electrode 272B, and 272C. Electrode 272A is disposed between electrodes 272B and 272C. Electrodes 272B and 272C may be coupled to a relative ground voltage potential and function as a shield against noise or other parasitics, or help the signal to noise ratio. Multi-region angular displacement sensor 200D is illustrated as embedded in strand 212D.

It may be noted that FIG. 2 is provided for illustration rather than limitation. It should be further noted that features described herein may be combined, mixed, or eliminated with other features described herein. For example, in embodiments multi-region angular displacement sensor 200 may include sense regions 201 or angular displacement units 220 that have non-rectangular shapes, such as V-like shapes or split shapes. In embodiments, multi-region angular displacement sensor 200 may include an angular displacement unit 220 orientated along different axes. For example, as discussed above, an angular displacement unit 220 may be orientated perpendicular to center axis 210, or in any other orientation. In embodiments, an angular displacement unit 220 may be orientated in any arbitrary orientation to measure angular displacement along an arbitrary axis and or may include any arbitrary number of additional planes of measurement. In embodiments, compliant capacitors 270 and/or 271 may include one or more electrode configurations. For example, a first electrode of a compliant capacitor may be fully enclosed by a second electrode. In another example, an electrode of a compliant capacitor may be on the surface (or partially embedded) in strand 212 to help shield from noise and other parasitic signals. In embodiments, multi-region angular displacement sensor 200 or strand 212 may be include compliant regions made from softer compliant material than surrounding regions, or material with cutouts for decreasing compliant, or material with reduced thickness compared to surrounding regions. In some embodiments, the traces 230 may be made with compliant conductive material and are embedded in strand 212. In still other embodiments, multi-region angular displacement sensor 200 may include one or more sense regions 201 that include sense units with other sense elements, such as compliant strain sense elements of a strain unit, compliant force element of a force sensor unit, haptic actuator element of a haptic actuator element, or compliant electrodes (e.g., for measuring skin surface bio-potentials or skin conductivity). For example, a multi-region angular displacement sensor 200 that includes a sense region 201 with an angular displacement unit and another sense region 201 with a compliant strain unit may measure angular displacement in a sense region 201 and strain in another sense region 201.

FIG. 3 is an illustration of a multi-region strain sensor, in accordance with some embodiments. Multi-region strain sensor 300 may include similar features as multi-region angular displacement sensor 200, unless otherwise described. In embodiments, a strain unit 320 may include a sense element, such as compliant capacitor, as described with respect to FIGS. 1A-C and 2. In some embodiments, the compliant capacitor of strain unit 320 may be orientated in a plane intersecting a center axis, rather than offset from the center axis. In embodiments, strain units 320 may be used measure strain responsive to a tensile force (e.g., stretch). In other embodiments, strain units 320 may be modified to be used to measure compressional forces, as described with respect to FIG. 4.

In embodiments, multi-region strain sensor 300 includes multiple sense regions 301 including sense region 301A, 301B, and 301C. In embodiments, each sense region 301 includes a strain unit 320 (e.g., stretch sensor). For example, sense region 301A includes strain unit 320A, sense region 301B includes strain unit 320B, and sense region 301C includes strain unit 320B. In embodiments, strain units 320 are compliant and deform similarly to an angular displacement unit.

In embodiments, sense regions 301 may include one or more sense elements, such as a compliant capacitor, and may sense strain independently. Sense region 301 may deform proportionally or substantially linearly to the applied strain. For example, in an unconstrained tensile test, the deformation should be linearly proportional to the applied strain for all strain values. In another example, in a constrained tensile test (e.g. the ends are clamped), the deformation may be linear from 20-100%, depending on width and length of the strain unit.

In some embodiments, attachment regions (e.g., a1-a4) are located between the one or more strain units 320. In embodiments, attachment regions of multi-region strain sensor 300 may be similar to the attachment regions described with respect to multi-region angular displacement sensor, described herein. In another embodiment, attachment regions may be located on top of the sense elements. In embodiments, the attachment regions may provide an attachment point to which the multi-region strain sensor 300 may be secured to a surface. In one embodiment, the attachment region of multi-region strain sensor 300 may have limited or no elasticity, so that tensile force may be imparted to strain units 320. In embodiments, the attachment region may provide a boundary so that a load may be applied and strain induced on a sense element. For example, a sense element may lie over a joint and an attachment region may be secured at a position above the joint and another attachment region may be secured below the joint. When the joint flexes, the flex induces a strain on the sense element, rather than in the attachment region. In embodiments, the attachment region may be made of any material, such as non-conducting elastomer or another non-conducting material. In other embodiments, the attachment region may be secured to another surface by any material, such as glue, a staple, or thread-like material.

In an embodiment, the multi-region strain sensor 300A illustrates the sense elements of the strain units 320 in a state of negligible strain. In an embodiment, multi-region strain sensor 300B illustrates the sense elements of the strain units 320 under different amounts of strain (e.g., 30%, 40%, and 20%). The percentage of strain is an indication of the amount of deformation (i.e., change in area) of each sense element from a negligible strain state to a strained state. A change in distance between the attachment regions induces a strain within the sense element. For example, if the reference capacitance (no deformation) for each sense region 301 is 100 pF, the capacitance resulting from the applied strain (shown as x values on the axis on the top of multi-region strain sensor 300) may result in a proportional or substantially linear increase in capacitance for each sense element. Although multi-region strain sensor 300 illustrates a multi-region strain sensor with three sense regions 301, it may be noted that multi-region strain sensor may have any number of sense regions 301. It should also be noted that a multi-region sensor may include one or more sense regions with angular displacement units, one or more sense regions with strain units, and/or any one or more sense regions with other types of sense units.

Figure 4:
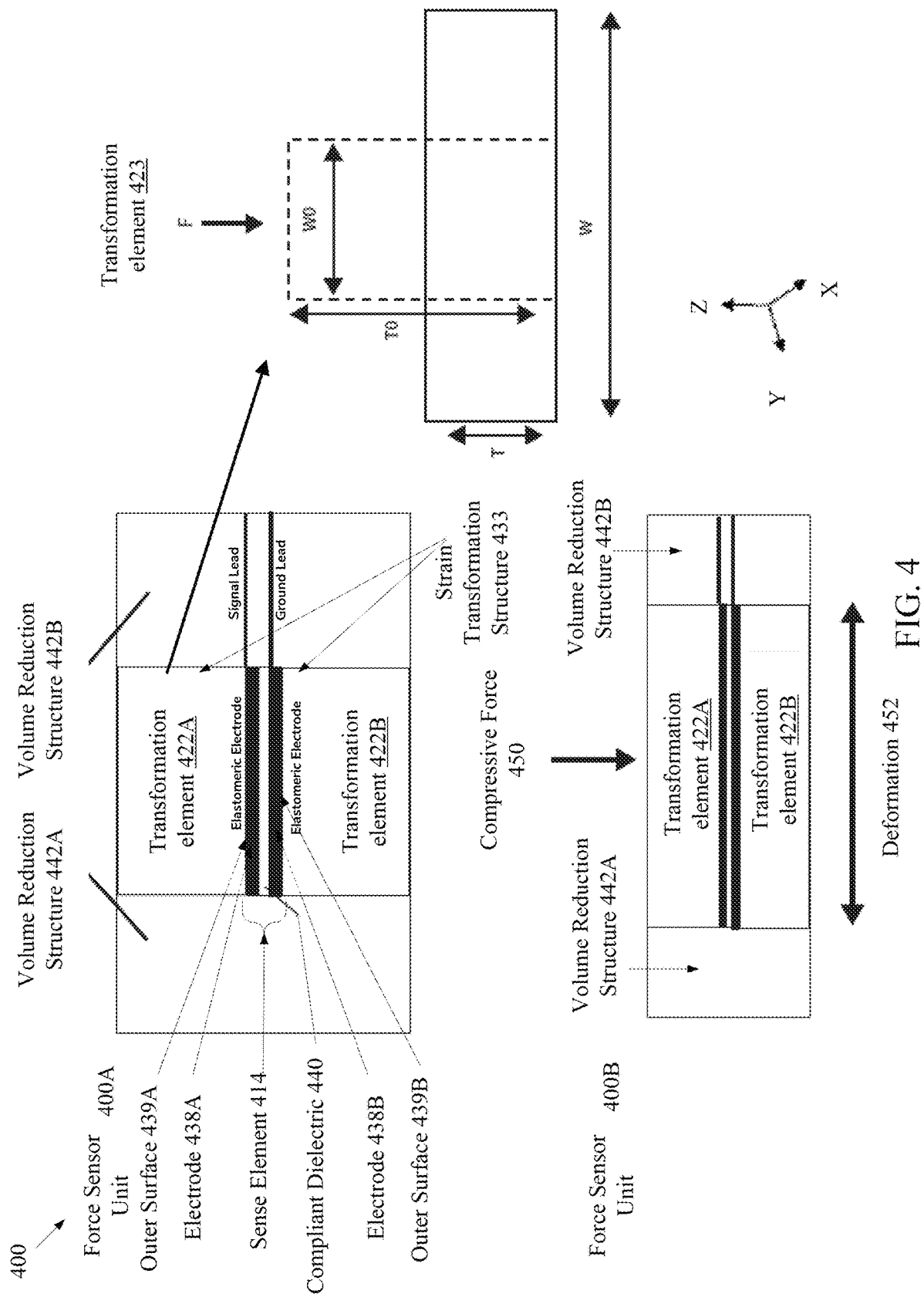
FIG. 4 is an illustration of a force sensor unit, in accordance with some embodiments.

FIG. 4 is an illustration of a force sensor unit 400, in accordance with some embodiments. In embodiments, a force sensor unit 400 may translate a received compressive force 450 into a substantially linear change in capacitance of the sense element 414. It may be noted that features of strain unit 320 as described with respect to FIG. 3, may be further applied in describing force sensor unit 400. For example, strain unit 320 is described as having a proportional or substantially linear change in capacitance responsive to tensile strain. In embodiments, capacitance of a sense element 414, such as a parallel plate compliant capacitor, of strain unit 320 is a linear function of area of the compliant capacitor.

In embodiments, compressive force 450 perpendicular to the X-Y plane may be applied to the strain transformation structure 433. The compressive force 450 may induce a deformation of a surface of strain transformation structure 433 (e.g., area of the bottom surface of transformation element 422A) parallel the X-Y plane. For example the bottom surface of transformation element 422A may deform axially (e.g., along the Y-direction) or bi-axially (e.g., along the X and Y direction). In embodiments, the deformation of strain transformation structure 433 may be substantially linear to the compressive force 450. The deformation of the surface of strain transformation structure 433 (e.g., surfaces coupled to the sense element 414) induces a substantially linear change in the area of sense element 414. In embodiments, the change in area of the sense element induces a change in area of one or more of the electrodes of the sense element 414. In other embodiments, the change in area of the sense element also induces a decrease in thickness or distance between the electrodes of sense element 414. In instances where the sense element 414 is a parallel plate compliant capacitor, the substantially linear change in area of sense element 414 may induce a substantially linear change in capacitance in the sense element 414. In embodiments, the capacitance of sense element 414 may be indicative to the applied compressive force 450 on strain transformation structure 433. In embodiments, the strain transformation structure 433 may convert a compressive force 450 to an axial or biaxial strain within sense element 414. The compressive force 450 is converted to a measurable and substantially linear change in capacitance. In embodiments, strains along the Z-axis of the strain transformation structure in response to force would be within 0-50%, with 0-20% being ideal. The force will induce strains in the X and Y-axis of 0-40% strain. In one embodiment the range of strain is within 0-10%.

In embodiments, force sensor unit 400A shows force sensor unit 400 under no or negligible compressive force 450 (e.g., load). Force sensor unit 400B shows force sensor unit 400 under compressive force 450. In embodiments, the compressive force 450 may be perpendicular to the X-Y plane. For purposes of illustration, the X-Y plane may be orthogonal to the page illustrating FIG. 4 and bisect the page. In embodiments, sense element 414 may be orientated parallel to the X-Y plane, where each layer (electrode 438A, dielectric 440, and electrode 438B) is also orientated parallel to the X-Y plane.

In embodiments, sense element 414 is a compliant capacitor similar as described with respect to FIGS. 1-3. Sense element 414 may include electrode 438A and electrode 438B. A dielectric 440 may be disposed between electrodes 438 in the X-Y plane. In other embodiments, sense element 414 may include more than two electrodes 438. For example, another electrode (not shown) may be disposed between electrode 438A and 438B, where the other electrode is disposed parallel to the X-Y plane. In embodiments, one or more outer electrode 438 (in a two electrode or greater configuration) may be coupled to a ground voltage potential using leads, for example. In embodiments, electrodes 438 and dielectric 440 are a compliant material, such as an elastomeric. In embodiments, the sense element 414 may deform in any direction in the X-Y plane and maintain connectivity and conductivity.

In embodiments, the force sensor unit 400 includes at least one strain transformation structure 433. In embodiments, a strain transformation structure 433 may include one or more transformation elements 422. As illustrated, strain transformation structure 433 includes transformation element 422A and 422B above and below sense element 414, respectively. Transformation element 422A may be coupled to the outer surface 439A of electrode 438A in a manner that a deformation of the bottom surface of transformation element 422A induces a similar deformation of electrode 438A. Transformation element 422B may be coupled to the outer surface 439B of electrode 438B in a manner that a deformation of the bottom surface of transformation element 422B induces a similar deformation of electrode 438B. Transformation elements 422 may be coupled directly or in some other manner to respective transformation elements 422. As noted above the transformation elements 422 may deform axially or bi-axially. In some embodiments, transformation element 422 may constrained so as to be prevented to deform along at least one axis (e.g., X-axis), but allowed to deform along another axis (e.g., Y-axis). In some embodiments, transformation element 422A and 422B of strain transformation structure 433 may be the same material or different materials.

In embodiments, strain transformation structure 433 may be at least partially surrounded by volume reduction structure 442. As illustrated, in one embodiment, volume reduction structure 442 may surround the sides of strain transformation structure 433. In embodiments, volume reduction structure 442 may be a compressible material, such as open cell foam, closed cell foam or a fluid or gas allowed to flow outside the volume reduction structure 442. In embodiments, volume reduction structure 442 may be made from a material that is more compressible than a material used for transformation elements 422. In embodiments, volume reduction structure 442 may reduce in volume to allow the strain transformation structure 433 to deform responsive to compressive force 450. As illustrated in force sensor unit 400b, volume reduction structure 442 illustrates a decrease in volume responsive to the deformation of strain transformation structure 433.

In embodiments, transformation elements 422 are further illustrated by transformation element 423. Force (F) may represent an applied force, such as compressive force 450, applied to transformation element 423. Transformation element 423 may be a certain shape, such as a rectangular shape, a cylindrical shape, or any other geometric or non-geometric shape. In embodiments, transformation element 423 may be an incompressible material, such as an incompressible elastomeric material (e.g., silicones). In embodiments, an incompressible material may be deformed and remain of substantially the same volume. In some implementations, a substantially incompressible material has a Poisson's ratio very close to 0.5 (perfectly incompressible), and within the range of 0.4-0.5 in real materials. In embodiments, responsive to force (F), transformation element 423 may induce a lateral deformation or expansion. For example, the dotted line may represent an non-deformed transformation element 423 having a reference width (W0) and reference thickness (T0). As force (F) is applied, a new thickness (T) and width (W) is induced. It may be appreciated that Force (F) may induce a lateral deformation (W) (axial deformation) in two-dimensional space and/or similar depth deformation into direction of the page in three-dimensional space.

In embodiments, incompressible materials may deform in a linear or substantially linear manner. The deformation of transformation element 423 responsive to force on a rectangular piece of material with a given surface area may be illustrated by Equation 1.

$$\alpha=(1-F*K) \qquad [\text{Eq. 1}]$$

"F" is the applied force. "K" is the stiffness of the material, which may be a function of area and compressive modulus. "a" is the compression ratio, which is less than 1 form compressive deformation and is related to engineering strain (e) by Equation 2.

$$\alpha=(1-e) \qquad [\text{Eq. 2}]$$

"e" is negative for compression. For an incompressible material, such as an incompressible elastomer, the resulting deformation perpendicular to the applied force (F) may be identical in both directions and may described by Equation 3.

$$\lambda=1/\sqrt{\alpha} \qquad [\text{Eq. 3}]$$

"λ" is the resulting deformation, such as stretch in the X-Y plane that results from compression α in the z direction. The thickness (T), width (W), and surface area (A) is described by Equations 4-6. Surface area (A) may be the bottom and/or top (e.g. perpendicular surface to compressive force 450) of transformation element 423 (assuming that the deformation is constant through the thickness).

$$T=T0\alpha \qquad [\text{Eq. 4}]$$

$$W=W0\lambda \qquad [\text{Eq. 5}]$$

$$A=W0^2\lambda^2 \qquad [\text{Eq. 6}]$$

Capacitance (C) may be described by Equation 7.

$$C=\varepsilon A/T \qquad [\text{Eq. 8}]$$

"ε" is the permittivity of the material. Assuming that a compliant capacitor is embedded in the transformation element 423, the capacitance induced by a deformation of transformation element 423 where the deformation is induced by the applied force (F) may be expressed in Equation 8.

$$C=(\varepsilon W0^2 T0)(\alpha)^{-2} \qquad [\text{Eq. 8}]$$

It may be noted that Equation 8 is nonlinear, but for small values of the compression ratio "α", a substantially linear relationship may be achieved. For example, for a compression ratio of 95%, the capacitance error is approximately 1.3%, for a compression ratio of 90%, the capacitance error (e.g., the deviation of capacitance from a linear model of percent capacitance change to compression ratio) is approximately 2.7%, for a compression ratio of 85%, the capacitance error is approximately 4.3%, for a compression ratio of 80%, the capacitance error is approximately 6%, and for a compression ratio of 70%, the capacitance error is approximately 10%.

In embodiments, the compression ratio of transformation element 423 may be chosen to meet a particular application's requirements. In some embodiments, a compression ratio of 90% or greater may be used to minimize errors in the measurement of force (F). In some embodiments, to achieve an adequate compression ratio for a given incompressible material a proper stiffness (K) may be selected for transformation element 423. For stiffness (K) may scale the compression ratio as illustrated by Equation 1. In embodiments, stiffness (K) may be a function of both the cross-sectional area of the transformation element 423 and the elastic module of the material of transformation element 423. In embodiments, the stiffness may be selected in view of the desired dynamic range of the force sensor unit. For example, for large dynamic ranges (e.g., range of force applied to force sensor unit), a stiffer material and/or larger cross section may be selected, while the opposite may be selected for smaller dynamic ranges. In embodiments, for a given range of compressive force 450, a transformation element 422 or strain transformation structure 433 may be designed to have a substantially linear relationship between compressive force 450 and capacitance.

It may be noted that embodiments herein may also be applied to applications that use a non-linear response of elements and features described herein. For example, in applications where a linear response is not used, a force sensor unit and other embodiments described herein may be used. In embodiments, a force sensor unit may be used in high-strain applications (e.g., large range of compression ratios), such as between—the strut and frame of a car. In high-strain applications, a nonlinear calibration may be performed to generate accurate force measurement.

Figure 5:
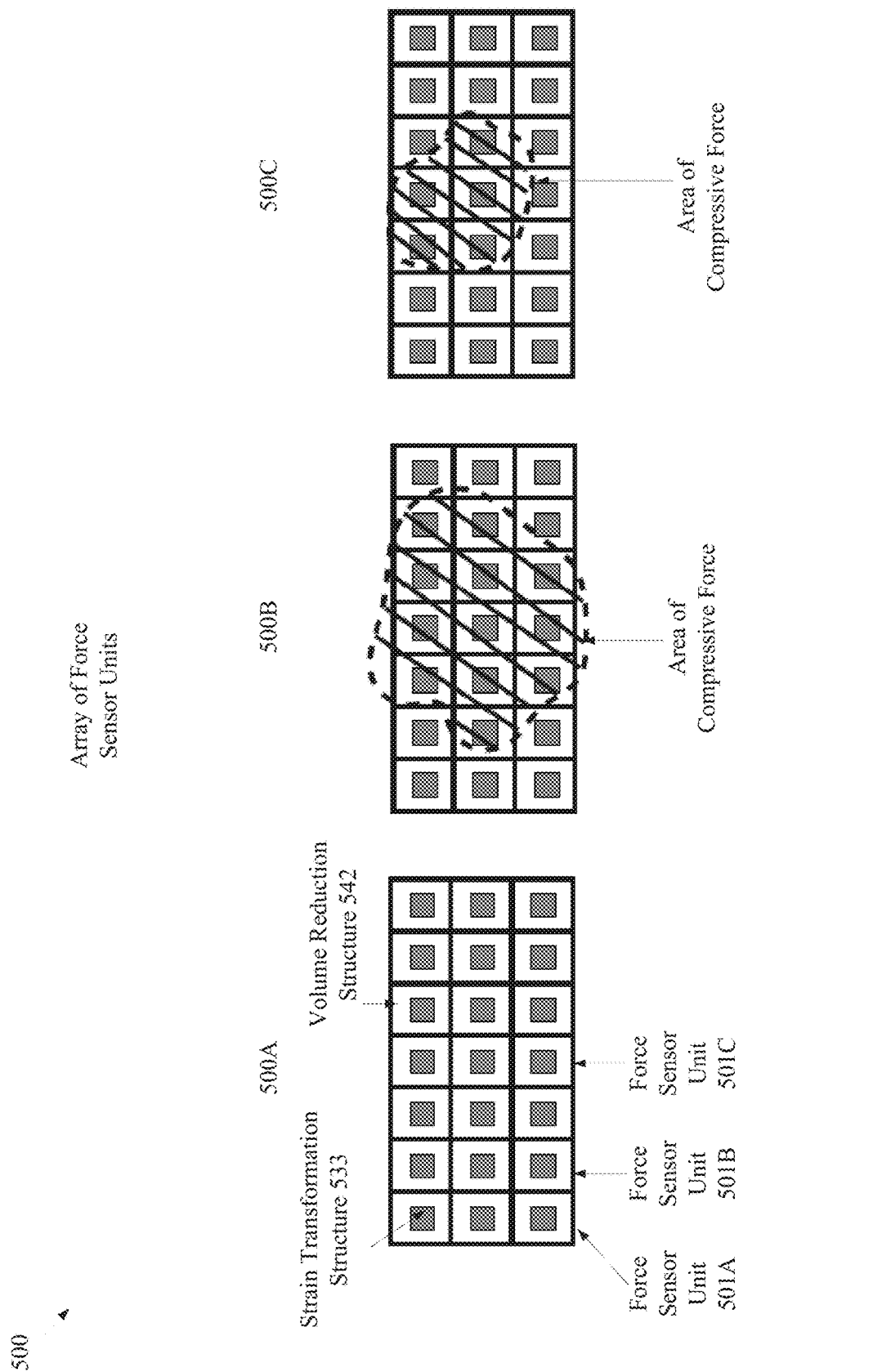
FIG. 5 is an illustration of an array of force sensor units, in accordance with some embodiments.

FIG. 5 is an illustration of an array of force sensor units 500, in accordance with some embodiments. In embodiments, an array of force sensor units 500 may include two or more force sensor units 501 arranged in any physical pattern. For purposes of illustration, rather than limitation, the array of force sensor units 500 includes 21 force sensor units 501. The force sensor units 501 have a strain transformation structure 533 surrounded on the sides by volume reduction structure 542. In embodiments, the force sensor units 501 of the array of force sensor units 500 may each have a separate sense element, such as a compliant capacitor. In other embodiments, one or more force sensor units 501 of the array of force sensor units 500 may share a sense element.

In embodiments, the force sensor units 501 of the array of force sensor units 500 may be coupled in parallel. In embodiments, force sensor units 501 may be coupled in parallel in a variety of ways. For example, force sensor units 501 may be physically wired to electrically couple in parallel. In another example, a multiplexer or other switch may be used to couple the force sensor units 501 in parallel. The multiplexer may also switch the coupling of force sensor units 501 to other configurations, in embodiments. In still another example, the one or more force sensor units 501 may be measured independently and later added together, by a processing device, for example.

In embodiments, array of force sensor units 500A shows the array under no to negligible compressive force. Array of force sensor units 500B and 500C shows a constant and same compressive force applied to each of the arrays but with different contact areas (e.g., area covered by dashed circular shape). In embodiments, an absolute force may be determined by the array of force sensor units 500. For example, the substantially linear response of the array of force sensor units 500 may induce a change in capacitance that is the same in array of force sensor units 500B and 500C. The array of force sensor units 500 may be an absolute force sensor invariant to the pressure profile. It may be noted that the aforementioned pressure profile may relate to the linear supposition principle, where adding a linear response of a linear force measurement unit, such as a force sensor unit 500, provides a total force irrespective of the force profile. It may be noted that the size and density of the strain transformation structure 533 may be selected to support the range of compressive forces being sensed. In some embodiments, strain transformation structures 533 may be spaced so as to allow expansion under the full range of compressive force and not be obstructed by adjacent force sensor units 501 or adjacent strain transformation structures 533. In embodiments, the stiffness or the shape of the strain transformation structures 533 may be chosen to provide a substantially linear capacitance response to a given range of compressive force or loading conditions.

Figure 6:
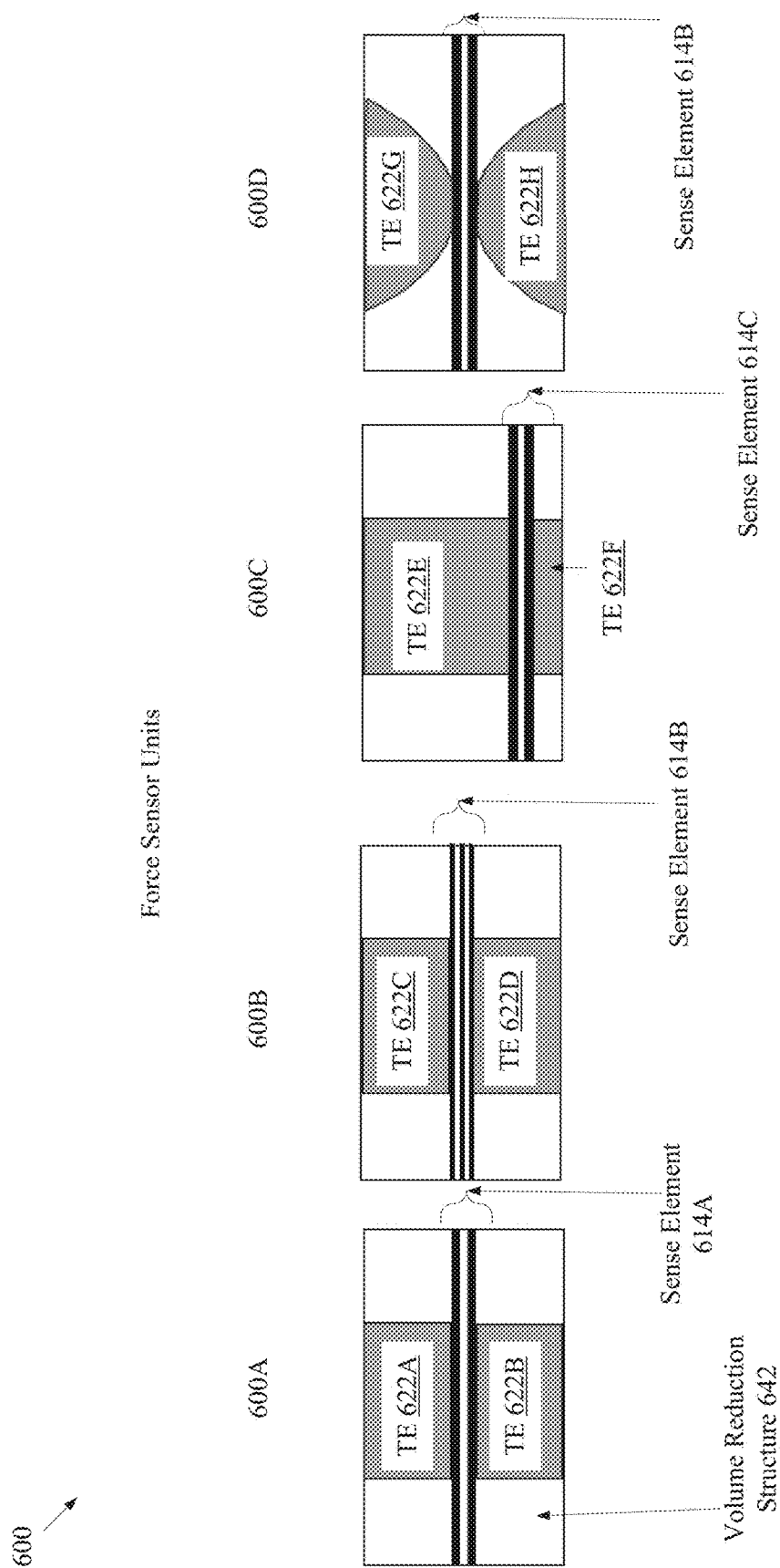
FIG. 6 is an illustration of force sensor units with different configurations, in accordance with some embodiments.

FIG. 6 is an illustration of force sensor units 600 with different configurations, in accordance with some embodiments. Force sensor units 600 show some variations of the force sensor unit. Force sensor units 600 are provided for illustration, rather than limitation, and are not meant to be exhaustive.

In an embodiment, force sensor unit 600A includes transformation element 622A and 622B which share a sense element 614B, such as a compliant capacitor. The transformation elements 622A and 622B are surrounded on the sides by volume reduction structures 642. In another embodiment, force sensor unit 600B is similar to force sensor unit 600A but has a sense element 614B with three electrodes. The middle electrode is between an upper and lower dielectric layer. In one embodiment, one or more outer electrodes of sense element 614B are coupled to a ground voltage potential (e.g., for shielding) and the middle electrode is a signal electrode to receive an applied voltage. In embodiments, force sensor unit 600C may be similar to force sensor unit 600A, but for the transformation elements 622E and 622F of the strain transformation structure being asymmetric. In another embodiment, force sensor unit 600D may be similar to force sensor unit 600A, but for the transformation elements 622G and 622H being different shapes. As noted above, the transformation elements 622 may be any shape and dependent on application. In some embodiments, an array of force sensor units may have the same or a variety of strain transformation structures.

Figure 7:
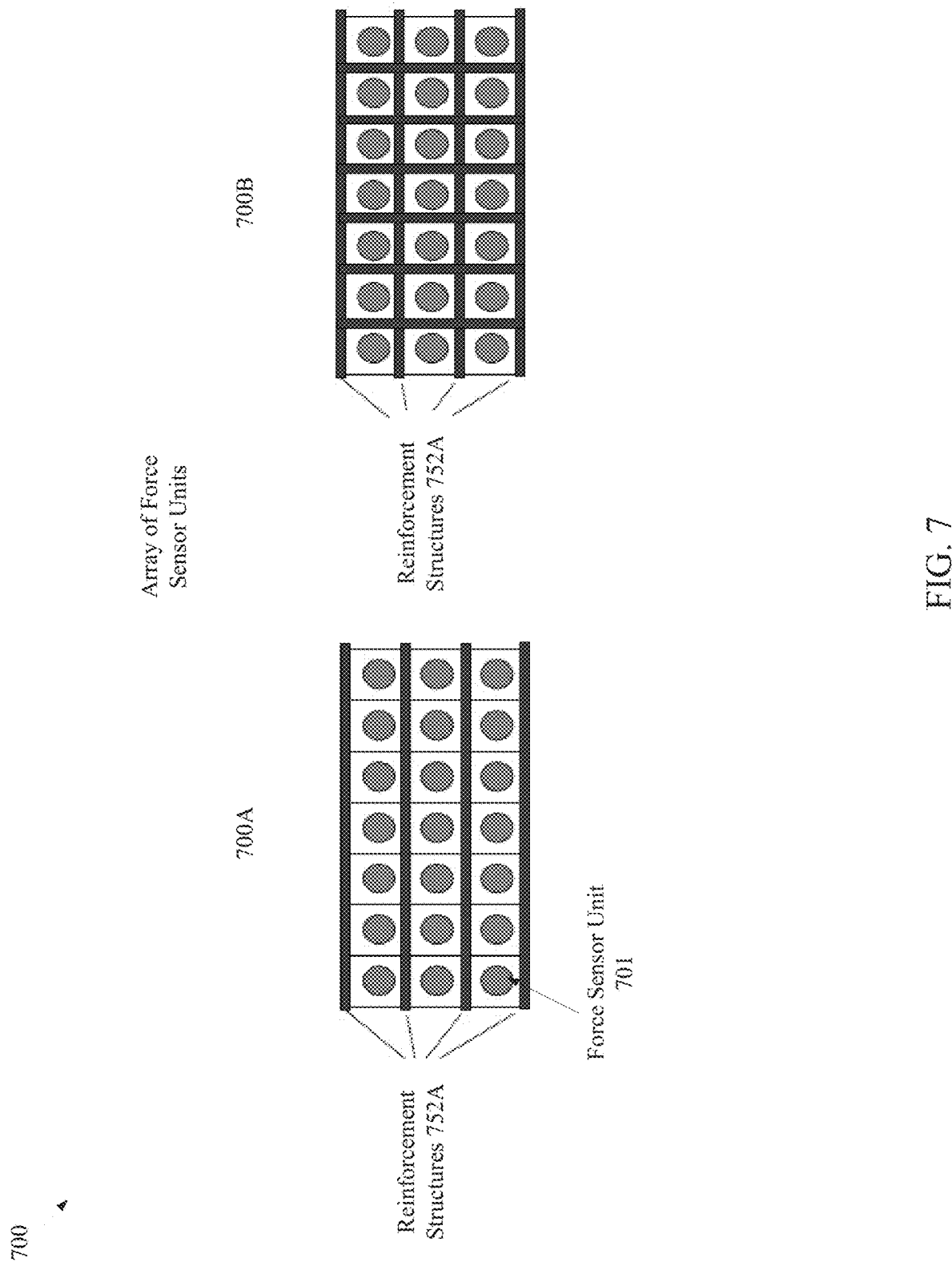
FIG. 7 is an illustration of an array of force sensor units with a reinforcement structure, in accordance with some embodiments.

FIG. 7 is an illustration of an array of force sensor units with a reinforcement structure, in accordance with some embodiments. Array of force sensor units 700 show the array with reinforcement structures 752. The array of force sensor units 700 are similar to other array of force sensor units as described herein. In embodiments, reinforcement structures 752 may be a material that is stiffer than strain transformation structures of the force sensor units 701. In embodiments, the reinforcement structure 752 may be a low profile so that a negligible load is deflected from the force sensor units 701, for example. In embodiments, the reinforcement structures 752 may provide additional rigidity, durability, or stiffness to a force sensor unit 701 or array of force sensor units 700.

Figure 8:
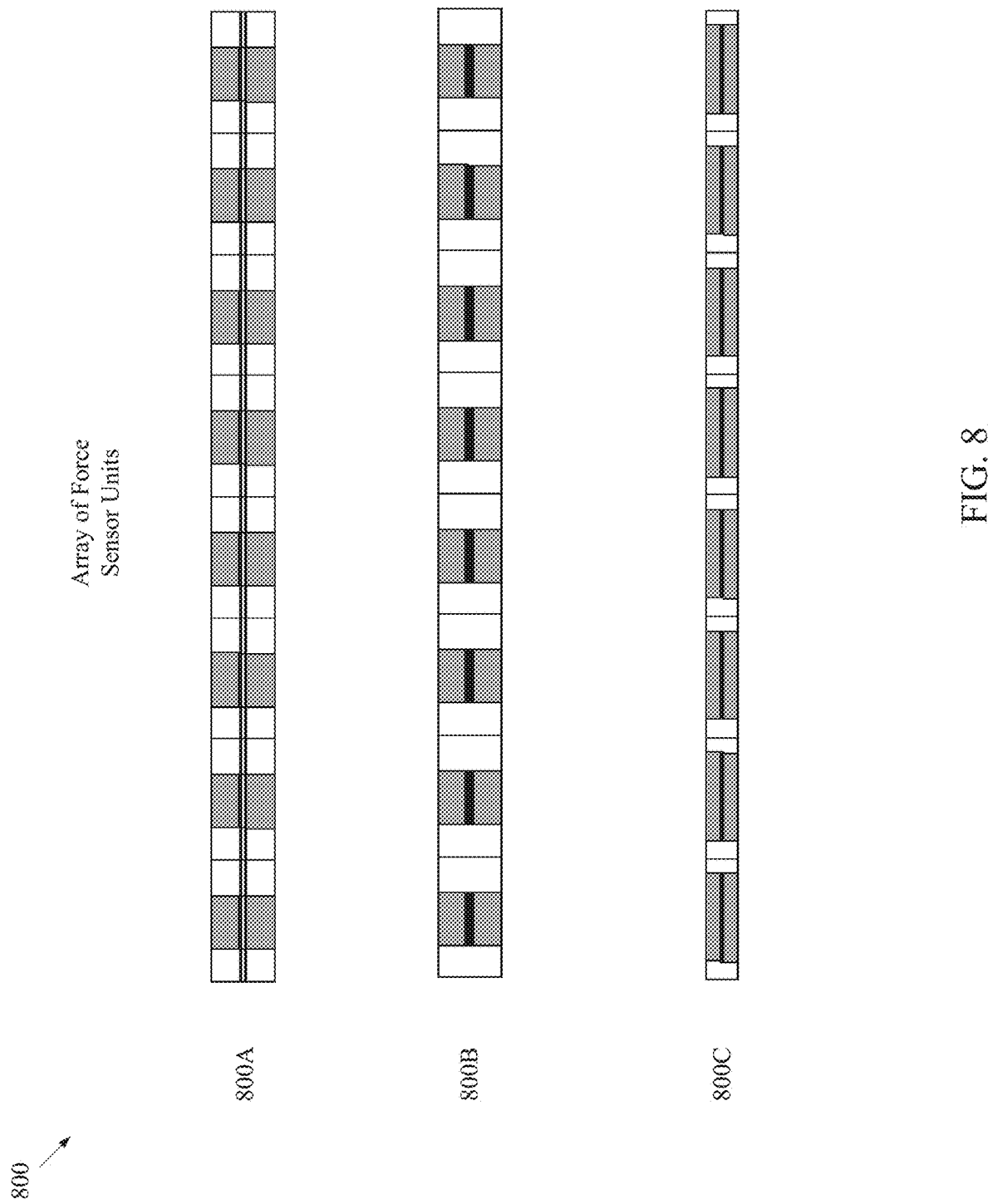
FIG. 8 is an illustration of cross-sectional view an array of force sensor units, in accordance with some embodiments.

FIG. 8 is an illustration of cross-sectional view an array of force sensor units 800, in accordance with some embodiments. In an embodiment, array of force sensor units 800A illustrates an array that uses a single large compliant capacitor that is shared between the individual force sensor units of the array of force sensor units 800A. In another embodiment, array of force sensor units 800B shows individual compliant capacitors associated with each of the force sensor units of the array of force sensor units 800B. In an embodiment, the force sensor units of array of force sensor units 800B may be coupled in parallel. Array of force sensor units 800A and 800B show the respective arrays with no or negligible compressive force (e.g., no load). In an embodiment, array of force sensor units 800C shows the force sensor unit of array of force sensor units 800B deformed under an applied compressive force. It may be noted that the force sensor units of array of force sensor units 800B may deform responsive to an applied compressive force 450 in a similar manner as illustrated in array of force sensor units 800C.

Figure 9:
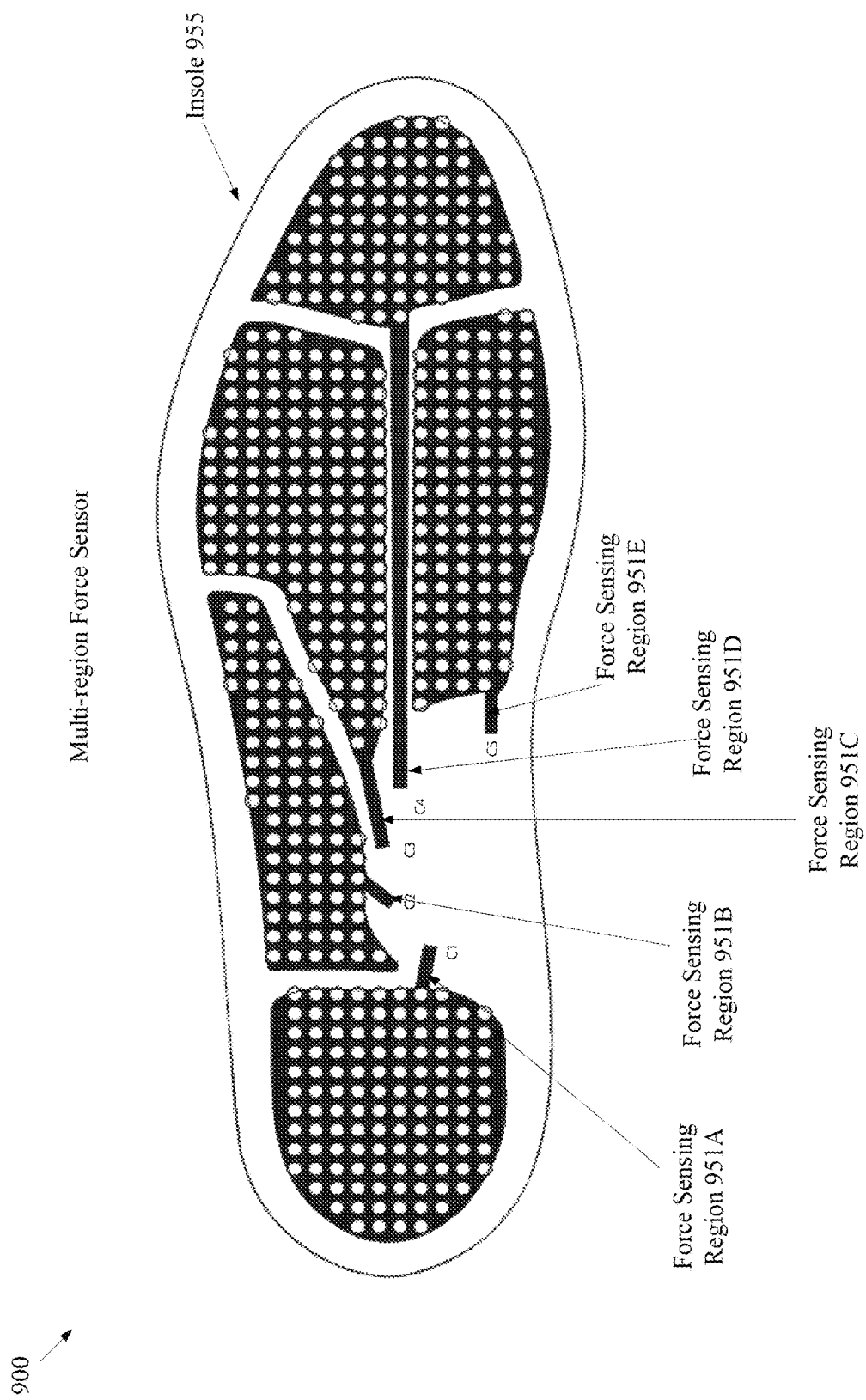
FIG. 9 is an illustration of multi-region force sensor embedded in an insole of footwear, in accordance with some embodiments.

FIG. 9 is an illustration of multi-region force sensor 900 embedded in an insole 955 of footwear, in accordance with some embodiments. In embodiments, multi-region force sensor 900 may have two or more force sensing regions, such as force sensing regions 951A through 951E. In embodiments, a force sensing region 951 may have one or more force sensor units. In embodiments, a force sensing region 951 may include an array of force sensor units. For purposes of illustration, rather than limitation, the multi-region force sensor 900 is shown to be at least partially embedded (or fully embedded) in an insole 955 of footwear, such as a shoe, sandal, clog, or others. In other embodiments, a multi-region force sensor 900 may be embedded in or part of numerous other objects, such as gloves, other parts of a footwear, mats, chairs, seats, clothing, socks, robotic elements, or automotive elements, among others.

In embodiments, force sensing regions 951 may be spatially and/or electrically distinct regions. In embodiments, force sensing regions 951 may have distinct compliant capacitors, strain transformation structures, and volume reduction structures. In embodiments, force sensing regions 951 may sense force independently from other force sensing regions 951. In some embodiments, the measured capacitance of different force sensing regions 951 may be added to determine a total compressive force on the insole by a human foot, for example. In embodiments, force sensing regions 951 may provide spatially discrete measurements of force.

Figure 10:
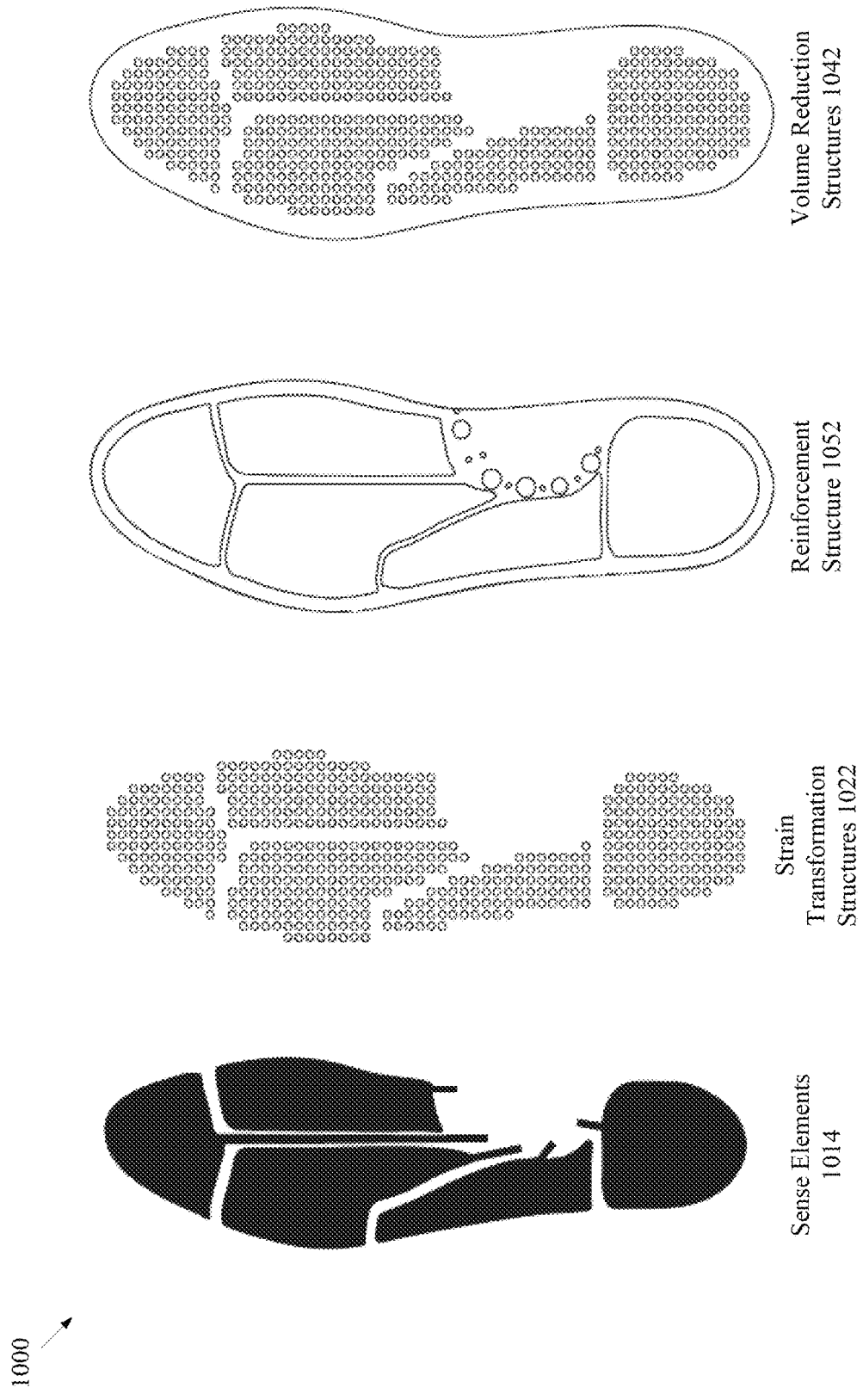
FIG. 10 is an illustration of the different parts of a multi-region force sensor of FIG. 9, in accordance with some embodiments.

FIG. 10 is an illustration of the different parts of a multi-region force sensor of FIG. 9, in accordance with some embodiments. In embodiments, multi-region force sensor 1000 may be an exploded view of multi-region force sensor 900. In embodiments, sense elements 1014 may be compliant capacitors where each force sensing region has a distinct compliant capacitor. In other embodiments, a force sensing region may have more than one compliant capacitor. In embodiments, sense element 1014 may be placed between transformation elements of strain transformation structures 1022. In embodiments, the insole may include a reinforcement structure 1052. In embodiments, reinforcement structure 1052 may be a stiffer material than strain transformation structure 1022 and add rigidity to multi-region force sensor 1000. The added rigidity may help prevent crumpling under shear and bending loads, for example. In embodiments, volume reduction structures 1042 may be embedded between the sides of strain transformation structures 1022. In one embodiment, volume reduction structure 1042 may be low-density open cell foam.

Figure 11:
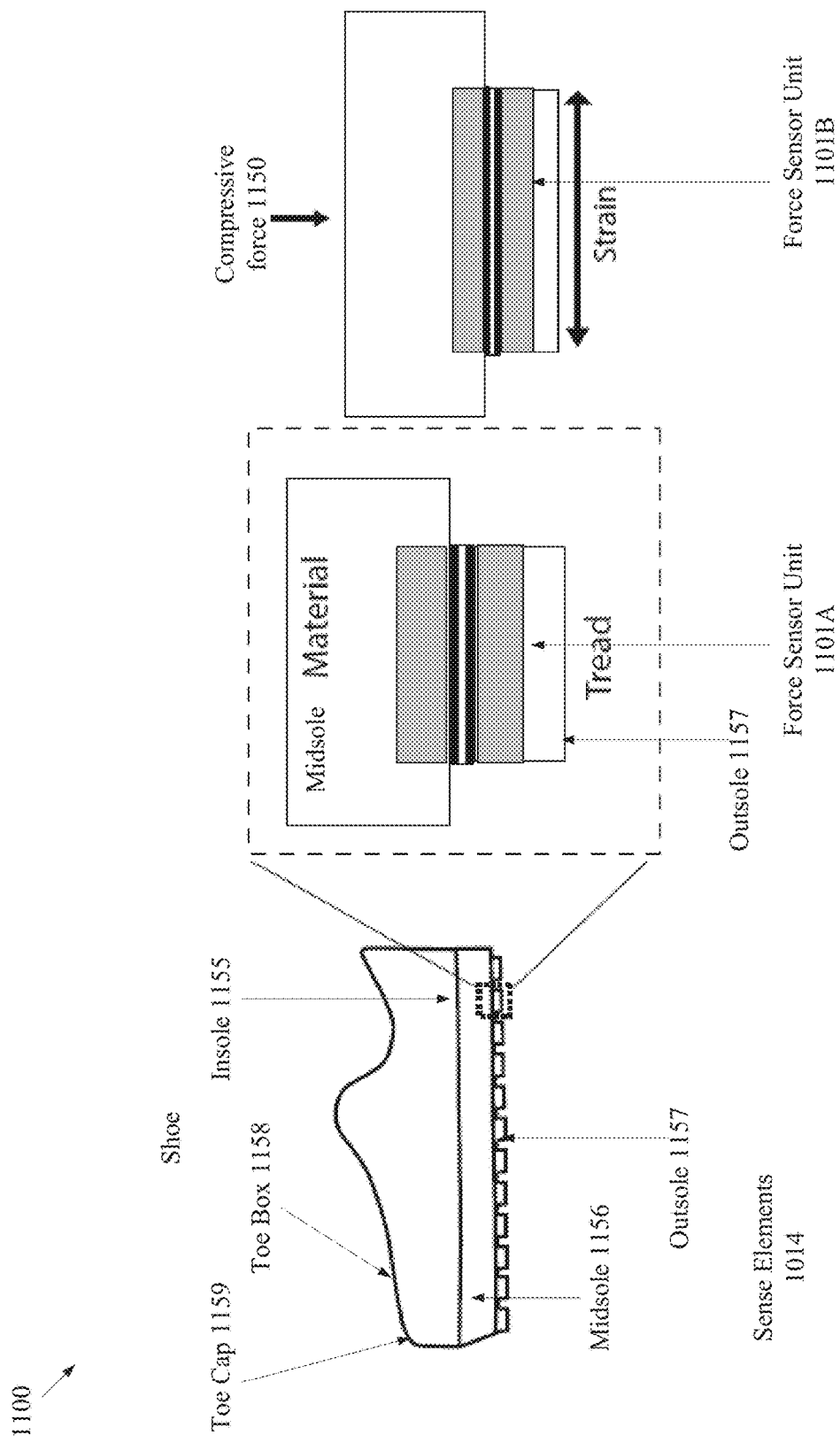
FIG. 11 is an illustration of force sensor units integrated into footwear, in accordance with some embodiments.

FIG. 11 is an illustration of force sensor units integrated into footwear, in accordance with some embodiments. In embodiments, footwear 1100 includes different parts such as a removable or non-removable insole 1155, midsole 1156, outsole 1157, toe box 1158, and toe cap 1159. It may be noted that footwear 1100 is simplified for purposes of illustration, rather than limitation, and may include fewer, additional, or different parts. In embodiments, force sensor units 1101 may be embedded at least partially in the outsole 1157 or between the midsole 1156 and outsole 1157. In some embodiments, the material of the outsole 1157 or material of the midsole 1156 may be used as transformation elements of a strain transformation structure. In other embodiments, transformation elements of a different material than the outsole 1157 or midsole 1156 may be used to provide the appropriate stiffness for the transformation elements, for example. Any of the sense units, multi-regions sensors, sense arrays, or sense elements described herein may be used in conjunction with footwear 1100.

In other embodiments, force sensor units 1101 may be positioned in different places in footwear 1100. For example, the force sensor units 1101 may be at least partially embedded the insole 1155, as illustrated in FIG. 10. In another example, the force sensor units 1101 may be at least partially embedded in the midsole 1156. In other examples, force sensor units 1101 may be located between the midsole 1156 and outsole 1157, as illustrated in FIG. 11. In other examples, force sensor units 1101 may be partially or totally embedded in the outsole 1157. In other examples, force sensor units 1101 may connected or embedded in the toe box 1158 or toe cap 1159, or any other location within or about footwear 1100.

Figure 12:
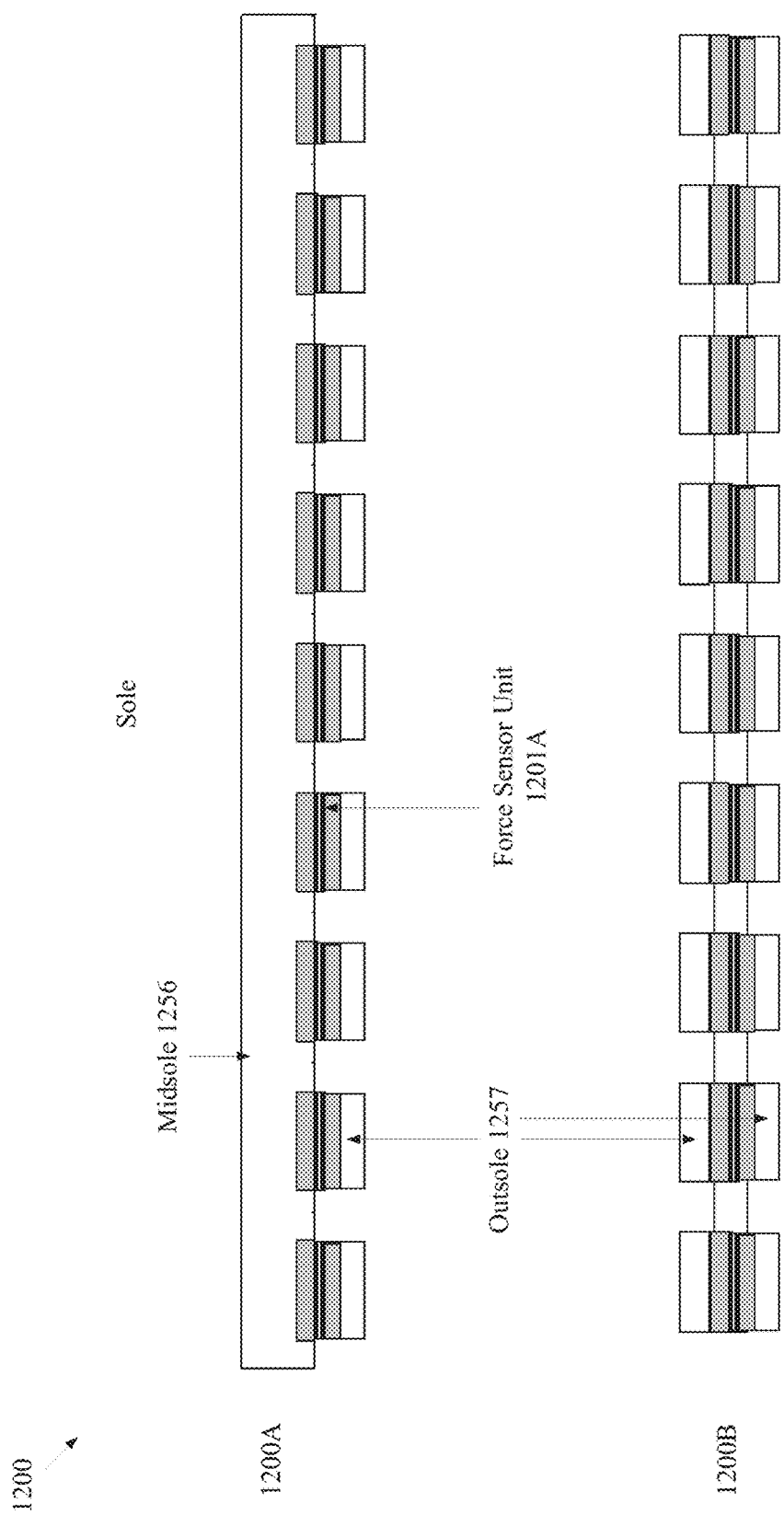
FIG. 12 is an illustration of force sensor units integrated into different parts of a sole for footwear, in accordance with some embodiments.

FIG. 12 is an illustration of force sensor units integrated into different parts of a sole for footwear, in accordance with some embodiments. Sole 1200 may be constructed to permanently or detachably affix to the bottom of footwear for force measurement. In one embodiment, midsole 1256 may be a sheet of material. Force sensor units 1201 may be attached between the outsole 1257 and midsole 1256. In embodiments, transformation elements may be used to achieve the desired stiffness. In other embodiments, the material of the midsole 1256 or outsole 1257 may be used transformation elements of a strain transformation structure.

In other embodiments, the configuration of sole 1200A may be used in other applications or with other materials. For example, the configuration of sole 1200A may be used as a scale, in a bath mat that measures force, or in seat cushions that measure force, etc.

Figure 13:
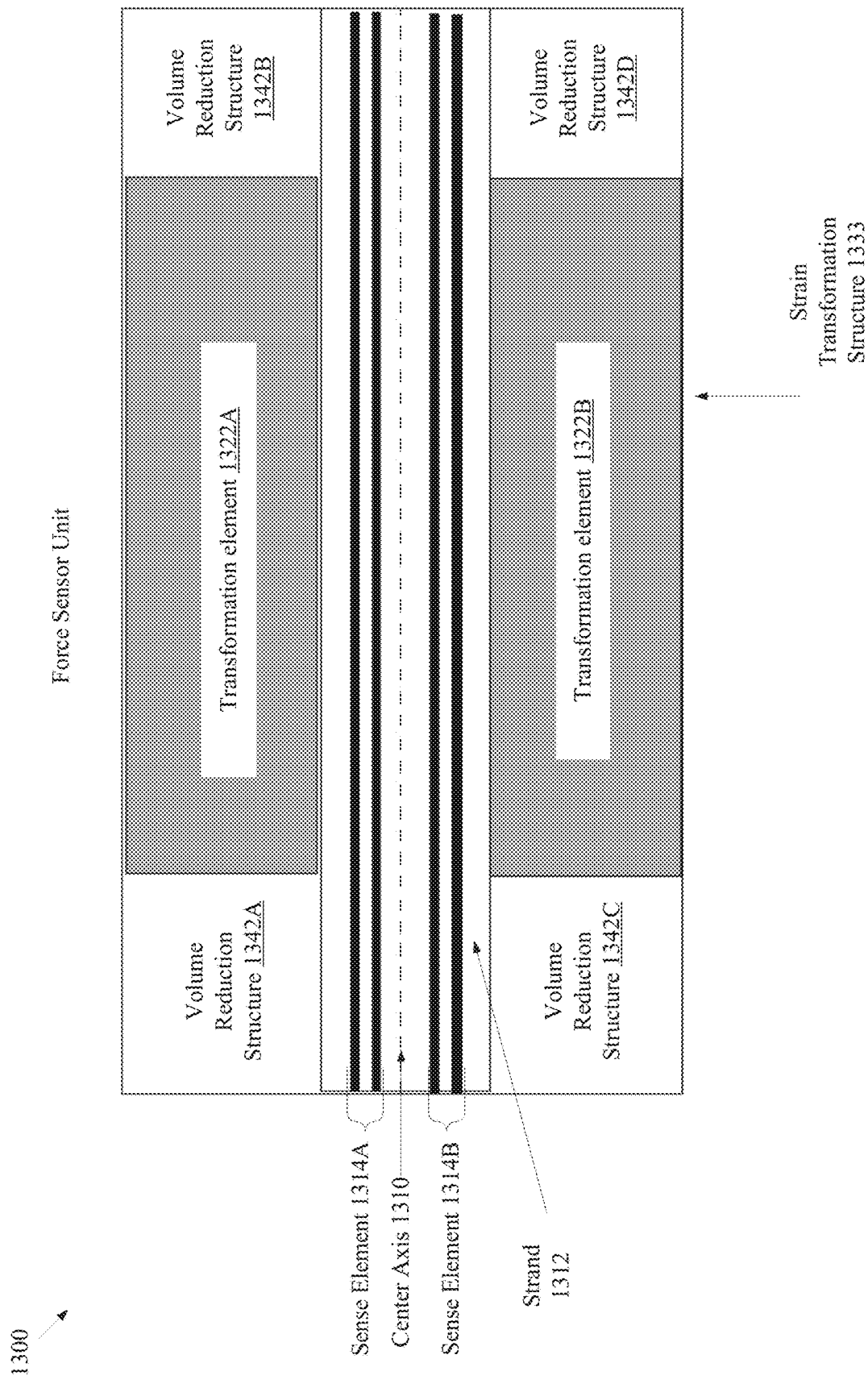
FIG. 13 is an illustration of a force sensor unit, in accordance with some embodiments.

FIG. 13 is an illustration of a force sensor unit 1300, in accordance with some embodiments. In embodiments, force sensor unit 1300 includes two or more sense elements 1314 offset and reflected about center axis 1310. In embodiments, sense elements 1314 are compliant capacitors. In embodiments, the sense element 1314 are embedded in strand 1312. In embodiments, strand 1312 may function similar to transformation elements 1322 or aid transformation elements 1322 of strain transformation structure 1333. In some embodiments, force sensor unit 1300 may include volume reduction structures 1342.

In some embodiments, using multiple sense elements 1314 in force sensor unit 1300 may aid in signal noise reduction. For example, the capacitances of sense element 1314 may be added to double the capacitance signal and reject noise, such as parasitic capacitance from bending (rather than desired capacitance from lateral strain from compressive force).

Figure 14:
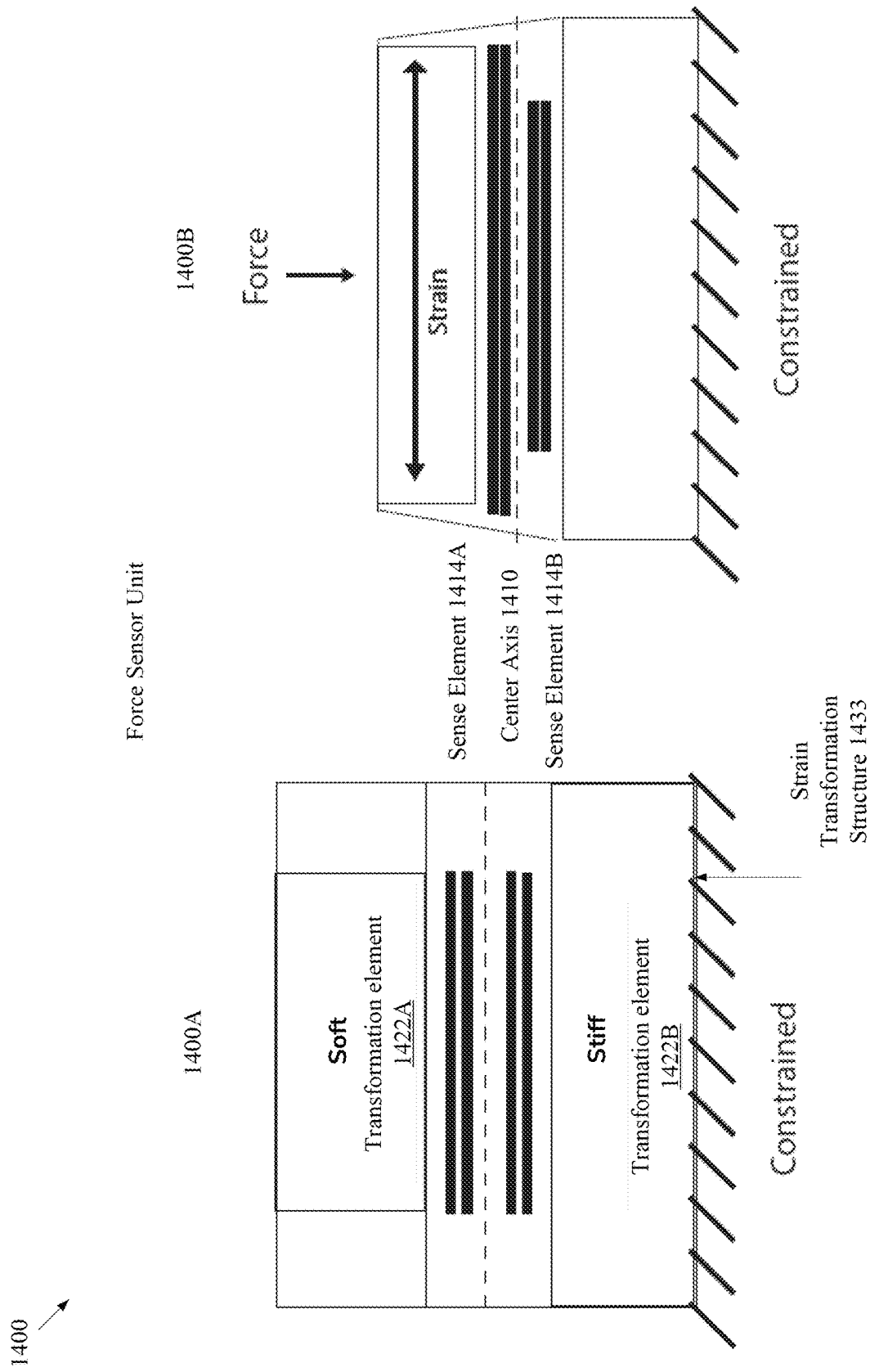
FIG. 14 is an illustration of a force sensor unit, in accordance with some embodiments.

FIG. 14 is an illustration of a force sensor unit 1400, in accordance with some embodiments. In embodiments, force sensor unit 1400 includes transformation elements 1422 of strain transformation structure 1433. Force sensor unit 1400 includes two sense elements 1414, illustrated as compliant capacitors, reflected about center axis 1410. Force sensor unit 1400A is shown with no or negligible applied compressive force, and force sensor unit 1400B is shown with an applied compressive force.

In embodiments, at least one side of strain transformation structure 433 may be constrained (e.g., not able deform such as in the lateral direction). For example, transformation element 1422B may be constrained by being glued or attached to a piece of metal, while transformation element 1422A is free to deform. In embodiments, transformation element 1422B may more or less be prevented from deformation. In some embodiments, where one of the transformation elements 1422 is constrained, compressive force 450 applied to the unconstrained transformation element 1422A may induce sense element 1414A to deform more than sense element 1414B. In embodiments, a differential measurement, such as a differential capacitance measurement of force sensor unit 1400B may be indicative of an applied compressive force 450 to force sensor unit 1400B.

Figure 15:
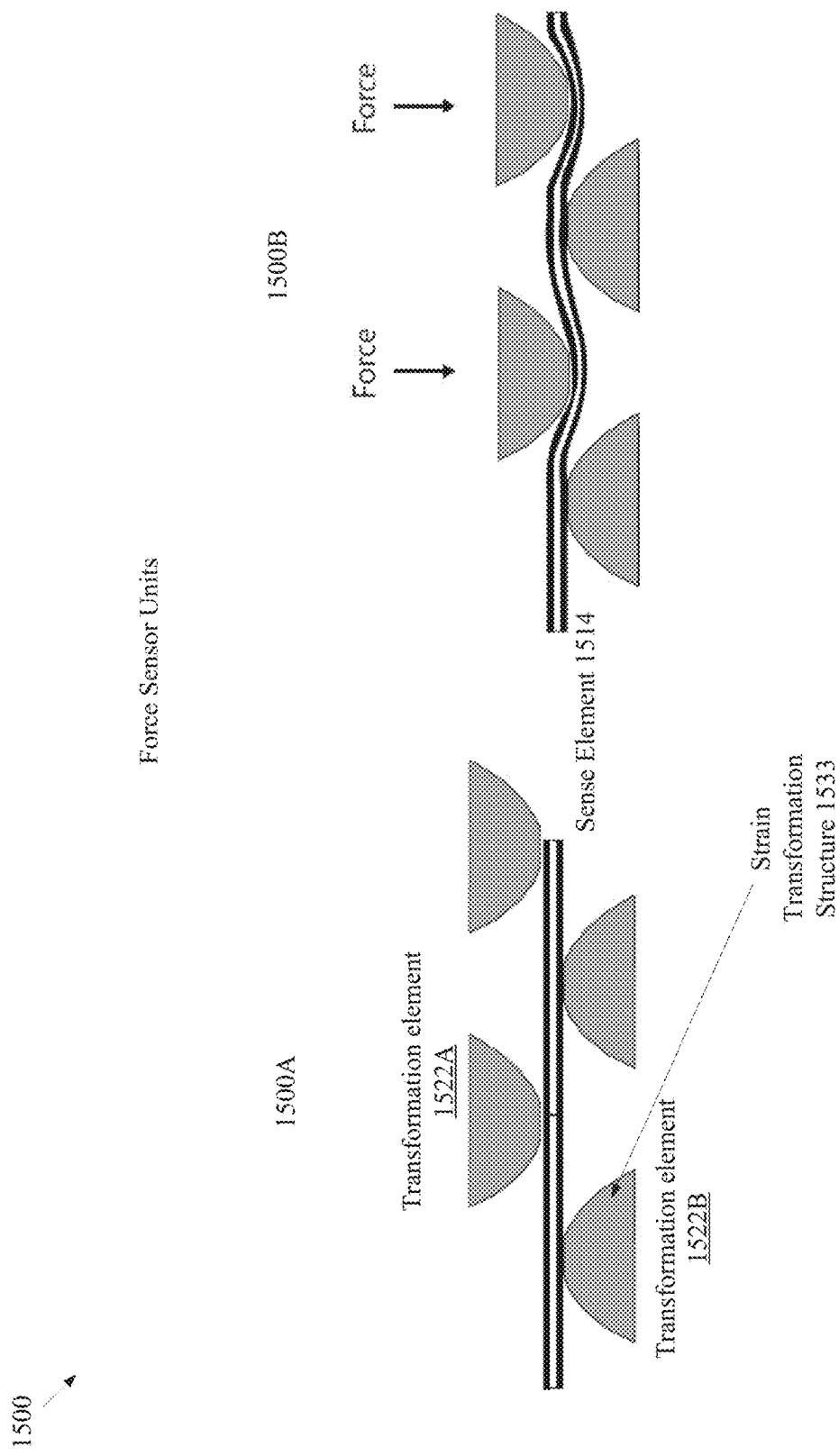
FIG. 15 is an illustration of a force sensor unit with offset transformation elements of a strain transformation structure, in accordance with some embodiments.

FIG. 15 is an illustration of a force sensor unit 1500 with offset transformation elements of a strain transformation structure, in accordance with some embodiments. In embodiments, force sensor unit 1500 may have strain a transformation structure 1533 with offset transformation elements 1522A and 1522B. For purposes of illustration, rather than limitation, two force sensor units are shown as part of force sensor units 1500A. In other embodiments, one or more force sensor units may be used.

In embodiments, responsive to an applied compressive force, strain transformation structure 1533 may induce a tensile or biaxial strain on the sense element 1514, illustrated as a compliant capacitor. In embodiments, the change in capacitance from a negligible applied compressive force to an applied compressive force may be substantially linear and indicative of the applied compressive force.

Figure 16:
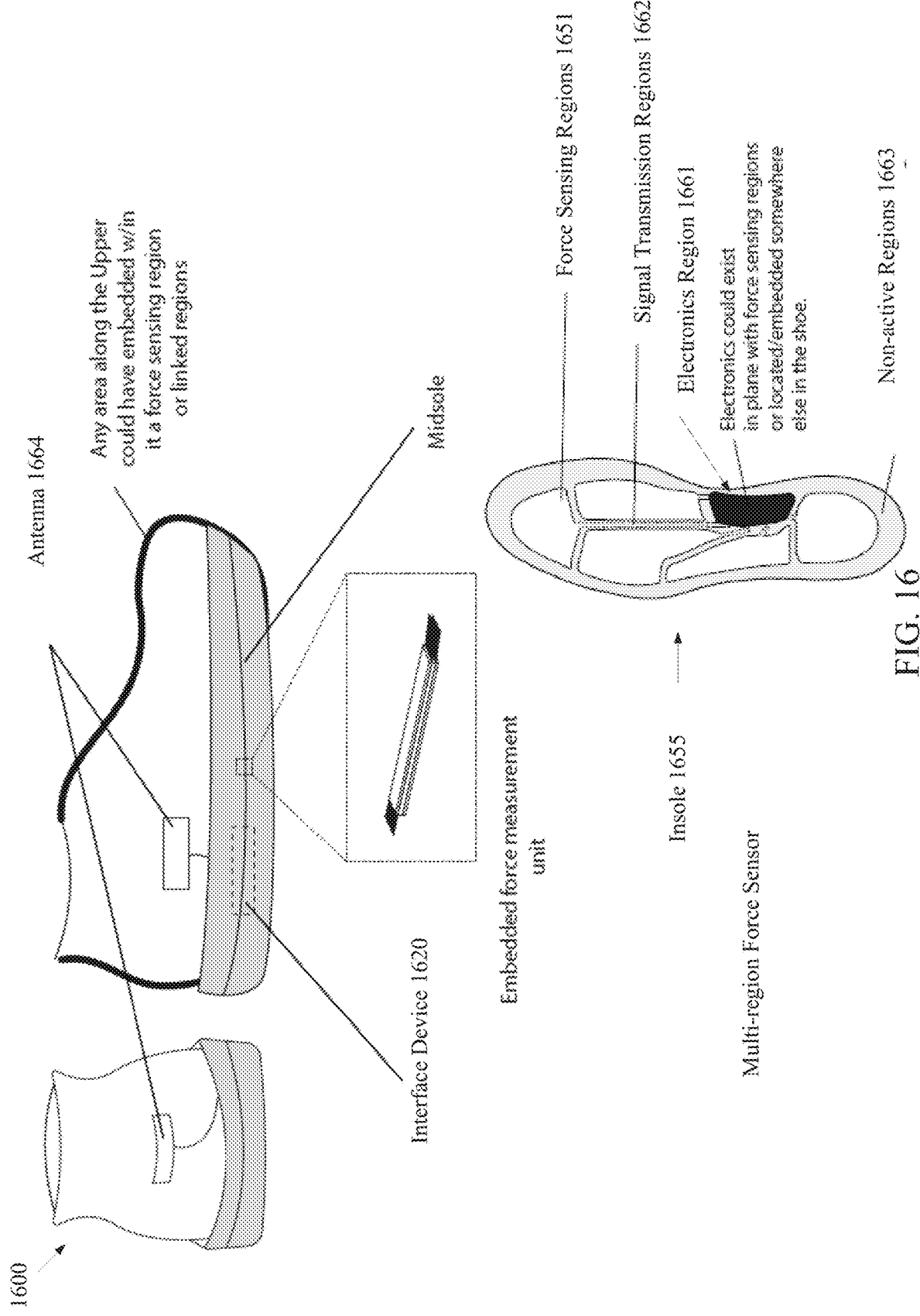
FIG. 16 is an illustration of a multi-region force sensor with associated electronics, in accordance with some embodiments.

FIG. 16 is an illustration of a multi-region force sensor 1600 with associated electronics, in accordance with some embodiments. In embodiments, multi-region force sensor 1600 may have one or more different regions, such as force sensing regions 1651, signal transmission regions 1662, electronics regions 1661, or non-active regions 1663. The multi-region force sensor 1600 is shown as part of insole 1655 for purposes of illustration, rather than limitation. In other embodiments, multi-region force sensor 1600 may be implanted in or about different objects. In some embodiments, non-active regions 1663 may include a reinforcement structure or insole padding material, for example.

In an embodiment, signal transmission regions 1662 conduct signals from force sensing regions 1651 to electronics region 1661. Electronics region 1661 may house an interface device 1620 (also referred to as "electronics module" or "electronics unit" or "electronics" herein). In some embodiments, interface device 1620 may include one or more of a capacitance measurement circuit, transceiver, or power source. In some embodiments, the power source may be a battery. In other embodiments, power harvesting circuits may be used as a power source. In some embodiments, the electronics region 1661 may be located in a different part of the footwear.

In some embodiments, an antenna 1664 may be coupled to interface device 1620. In embodiments, the antenna 1664 may be a radio-frequency (RF) antenna and be located conducive to sending and receiving signals, such as the heel or side of the footwear, for example.

Figure 17:
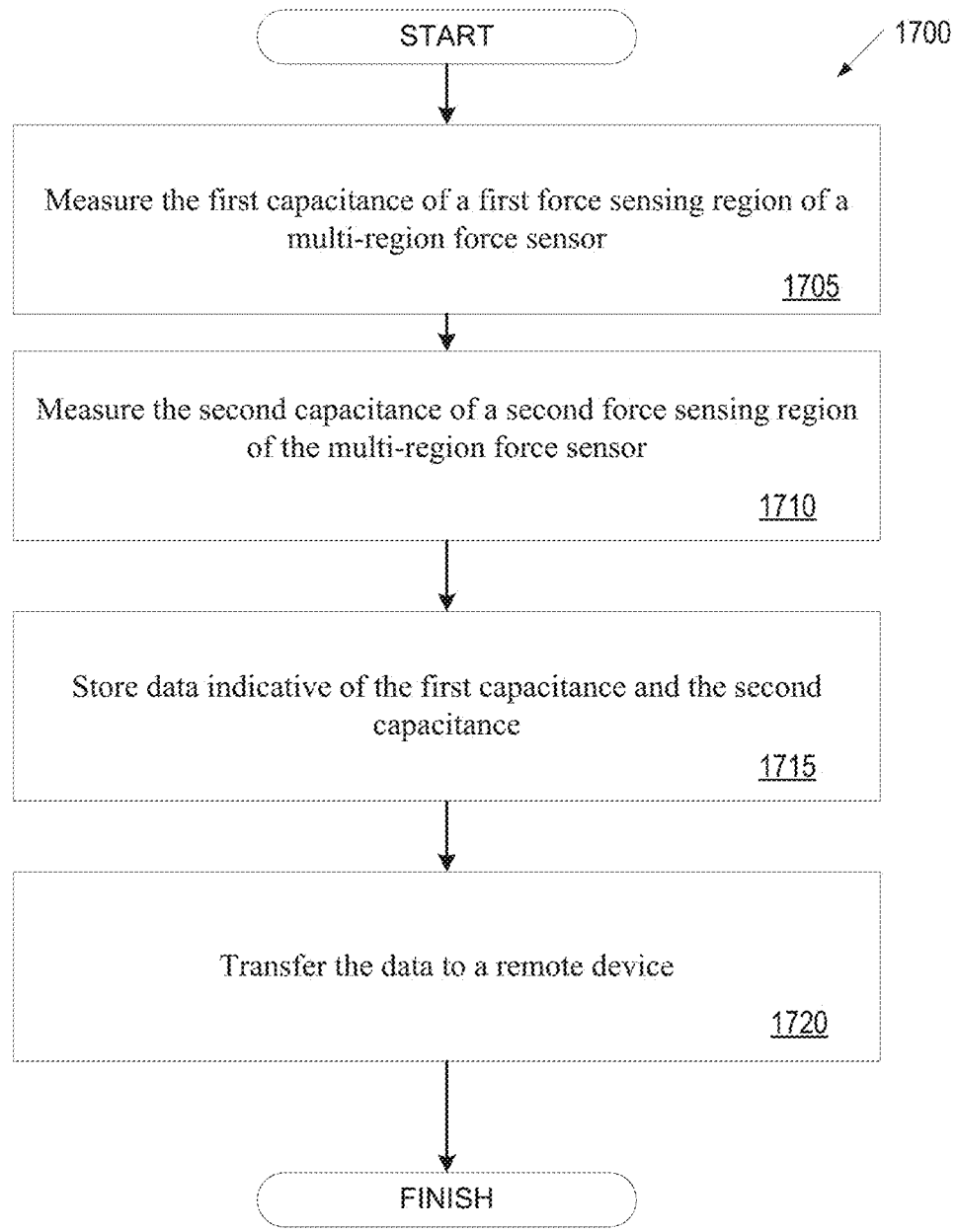
FIG. 17 illustrates a flow diagram of a method of compressive force using a multi-region force sensor, in accordance with some embodiments.
Figure 18:
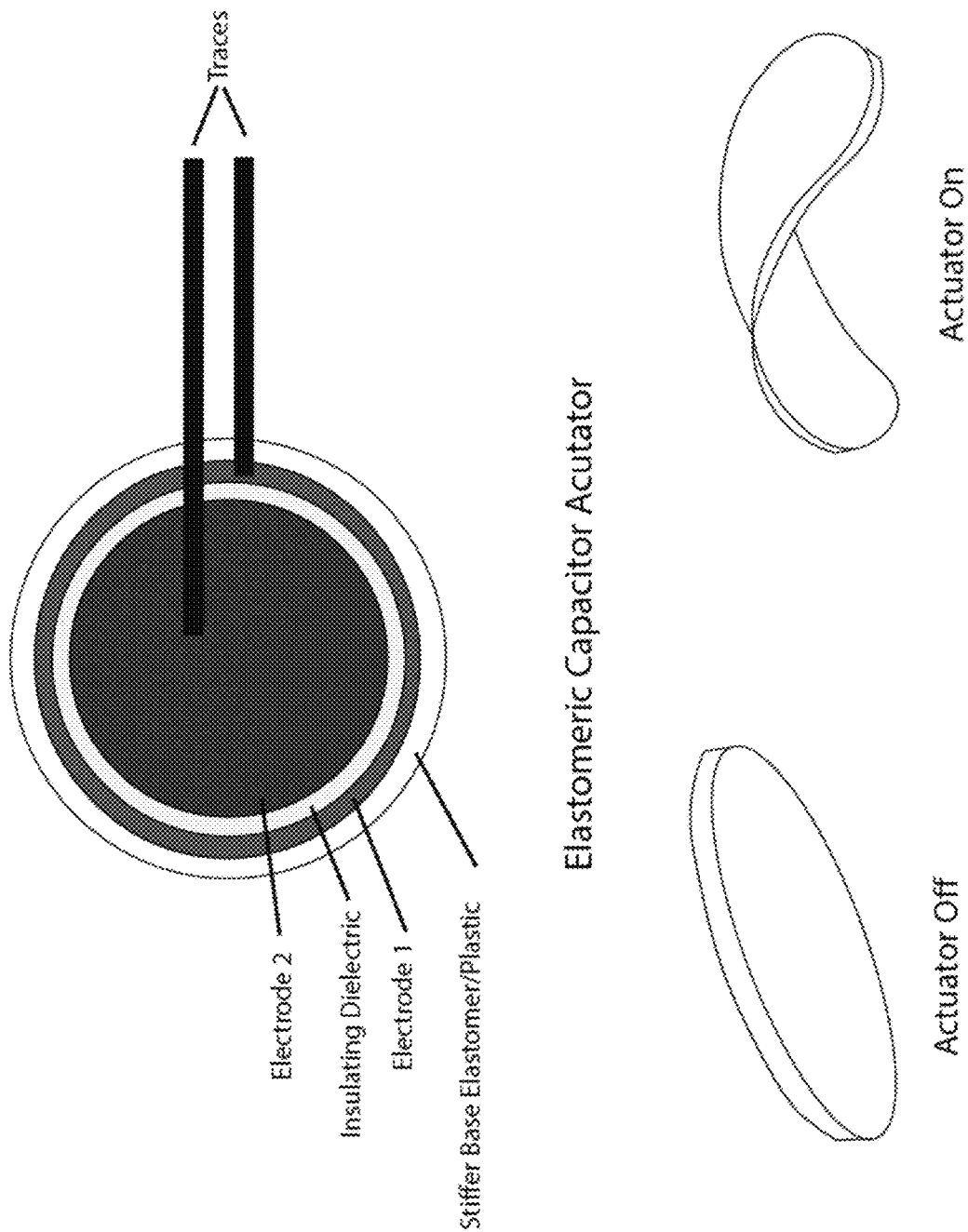
FIG. 18 illustrates a haptic actuator sense element, in accordance with one embodiment.

FIG. 17 illustrates a flow diagram of a method of compressive force using a multi-region force sensor, in accordance with some embodiments. The multi-region force sensor may include any elements as described herein. Method 1700 may be performed all or in part by processing logic that comprises hardware (e.g., circuitry, dedicated logic, programmable logic, microcode), software (e.g., instructions run on a processing device to perform hardware simulation), or a combination thereof. In one embodiment, an interface device performs all or part of method 1700.

The method 1700 includes providing a multi-region force sensor with multiple force sensing regions. A first sense region includes a first force sensor unit or array of force sensor units. A second force sensing region includes a second force sensor unit or array of force sensor units.

The method 1700 begins at block 1705 where processing logic measures a first capacitance of the first force sensing region of the multi-region force sensor. At block 1710, processing logic measures a second capacitance of a second force sensing region of the multi-region force sensor. At block 1715, processing logic stores data indicative of the first capacitance and the second capacitance. In some embodiments, the data may be raw capacitance data or digital counts. In some embodiments, the data may be the sum of the first and the second capacitance values. In other embodiments, the capacitance measurements may be used to determine a compressive force measurement (e.g. by applying a linear calibration or other calibration model), and the data may be indicative of the applied compressive force. The data may be stored at the interface device, for example. At block 1720, processing logic may transfer the data to a remote device, wirelessly or otherwise.

FIG. 18 illustrates a haptic actuator sense element, in accordance with one embodiment. In embodiments, haptic actuator sense element 1800 illustrates an elastomeric capacitor actuating sense element. In embodiments, the haptic actuator sense element 1800 includes two or more compliant electrode layers separated by one or more non-conducting elastomer layers (i.e., elastomeric capacitor). In one embodiment, the haptic actuator sense element 1800 may be placed on top of a compliant substrate (e.g., elastomer substrate) to form a haptic actuator unit. In embodiments, a compliant substrate may be isotropic or anisotropic. In embodiments, the compliant substrate may be stiffer or less stiff than the elastomeric capacitor. It may be noted the elastomeric capacitor of the haptic actuator sense element 1800 may be similar to the complaint capacitors, as described herein.

In embodiments, a voltage applied across the electrodes of the haptic actuator sense element 1800 cause the haptic actuator sense element 1800 to expand or contract (e.g., bend) due to Maxwell stress. In embodiments, a stiff compliant substrate causes the expansion of the haptic actuator sense element 1800 to be restricted, and causes a buckling or bending of the haptic actuator sense element 1800. In one embodiment, high frequency activation may cause a vibration of the haptic actuator sense element 1800. In other embodiments, a haptic actuating sense element may be one or more electrodes that produces an amount of heat or electric shock to simulate the touching of a hot object by a user, for example.

In embodiments, haptic actuator sense element 1800 may be included in a haptic actuator unit. In some embodiments, sense regions may include one or more haptic actuator units. In other embodiments, haptic actuator sensing regions may include one or haptic actuator units or a haptic actuator array. In embodiments, haptic actuator units may be implemented in a multi-region haptic actuator sensor. In embodiments, haptic actuator sense elements 1800 may be spatially separated from one another and each individually controlled, or controlled in parallel. In another embodiment, the haptic actuator sense elements 1800 may be configured in glove, insole, footwear, or other object to provide tactile stimulation, for example.

In embodiments, haptic actuator sense elements 1800 may provide haptic feedback. For example, haptic feedback may be a physical stimulation created by an electro-tactile and/or a vibro-tactile device. In other examples, haptic feedback may be used to create a sense of touch for a user by applying forces, vibrations, heat, electric current, and/or motions using haptic actuator sense elements 1800.

Figure 19:
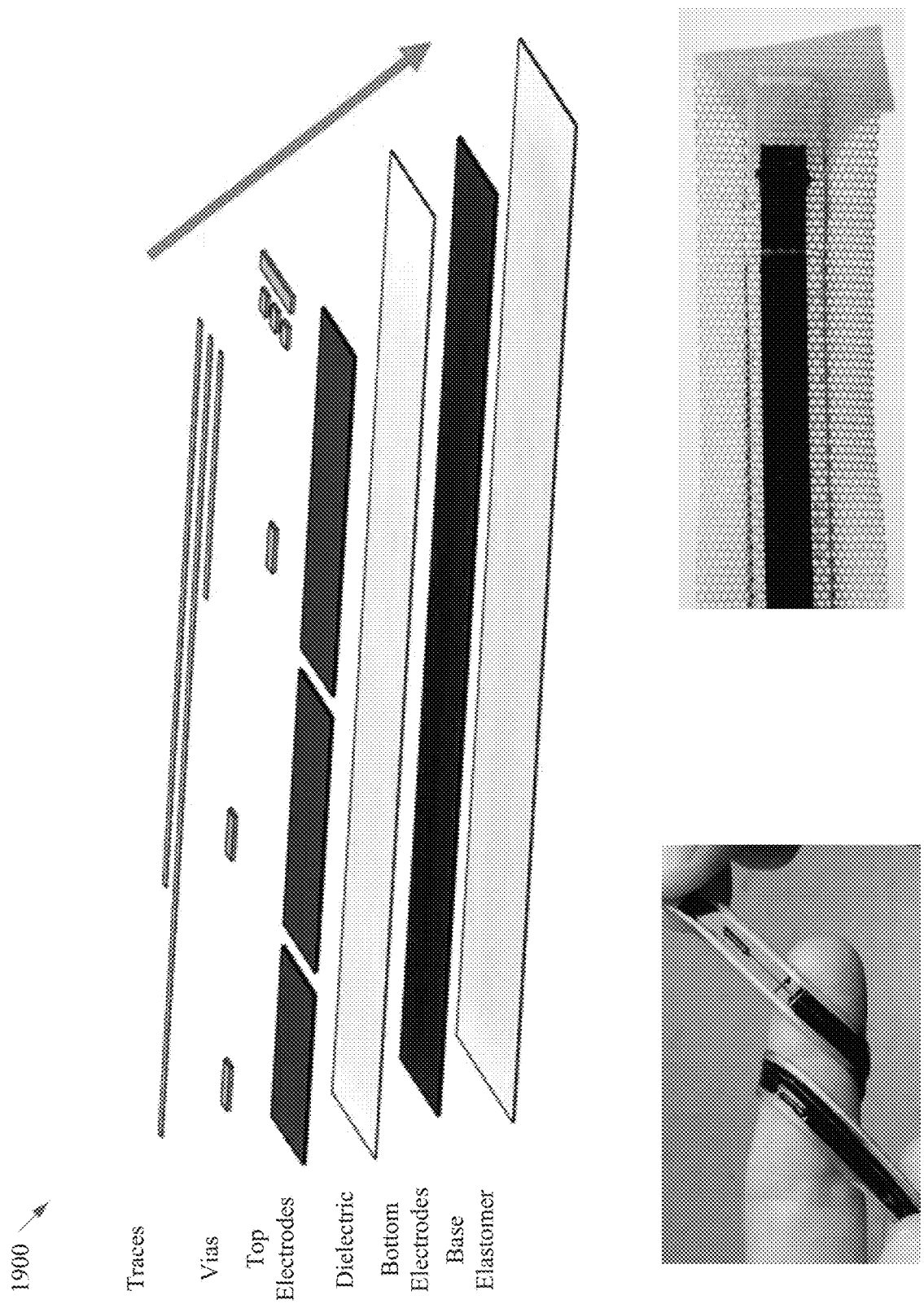
FIG. 19 illustrates a multi-region strain sensor on a flexible substrate, in accordance with some embodiments.

FIG. 19 illustrates a multi-region strain sensor on a flexible substrate, in accordance with some embodiments. Multi-region strain sensor 1900 shows an example of the various horizontal layers of a multi-region strain sensor. In embodiments, the conductive traces may be made from a conductive elastomer or other material and are coupled to the top electrodes through conductive vias. In embodiments, the top electrodes are spatially separated and are disposed above a dielectric layer. In embodiments, the dielectric layer is on top of a single shared bottom electrode. In embodiments, the single bottom electrode is disposed above a compliant substrate, such as a base elastomer.

As illustrated in the bottom left figure, in embodiments, the multi-region strain sensor 1900 is a compliant capacitor capable of bending or folding 360 degrees or more without breaking or compromising the physical and electrical integrity of the multi-region strain sensor 1900.

The bottom left figure illustrates the multi-region strain sensor 1900 wrapped around a finger. The bottom right figure illustrates a multi-region strain sensor 1900 manufactured on a compliant base material, such as fabric (e.g., a spandex mesh fabric). In some embodiments, one side of the fabric may have an adhesive to removably adhere to an object such as a human body part.

It may be noted that any sense unit (e.g., force sensor unit, angular displacement unit, or haptic actuator unit, strain unit, etc.), described herein, may configured in a similar manner. It should also be noted that the multi-region strain sensor 1900 may also include an encapsulating layer (not shown) that encapsulates the multi-region strain sensor 1900 and/or a shield layer (not shown) coupled to a voltage potential, such as electronic ground, to provide shielding from stray electric field lines and enable more accurate capacitance measurements.

Figure 20:
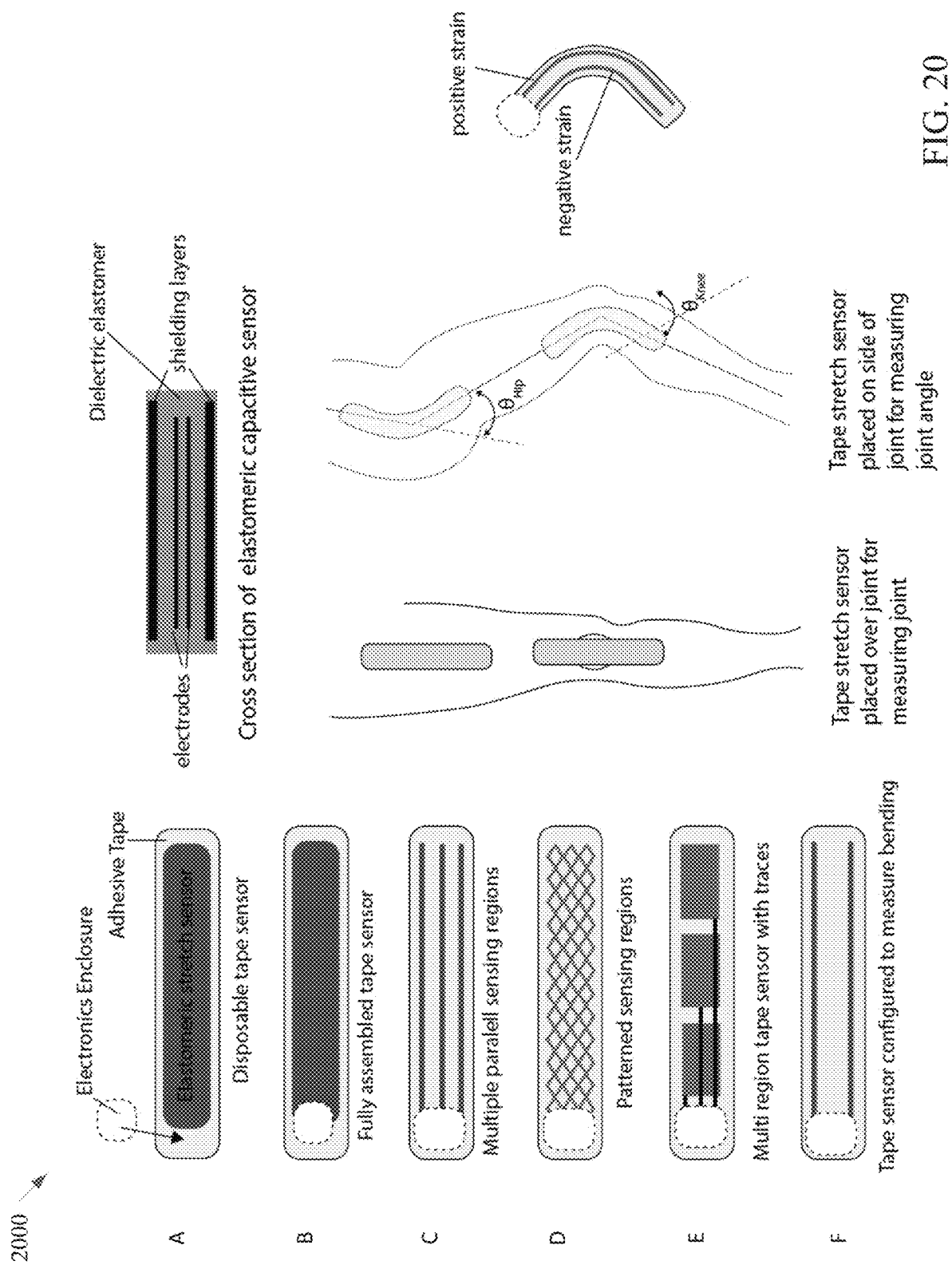
FIG. 20 illustrates one or more sense units on a flexible substrate, in accordance with some embodiments.

FIG. 20 illustrates one or more sense units on a flexible substrate, in accordance with some embodiments. For the sake of simplicity, sense unit 2000 may refer to a single sense unit or multi-region sensor. It may be noted that any sense unit, such as force sensor unit, angular displacement unit, haptic actuator unit, strain unit, or otherwise, may configured in a similar manner as described with respect to FIG. 20.

In embodiments, the sense units 2000 A-D may removably or permanently couple to a compliant substrate, such as adhesive tape. Examples of adhesive tape may include elastic therapeutic tape (e.g., kinesio tape), elastomeric tape, fabric tape, or the like. In embodiments, the sense units 2000 on the compliant substrate, such as adhesive tape, may be disposable or reusable. Sense units integrated onto a flexible adhesive substrate may also be referred to as "tape sensors" herein.

In another embodiment, the compliant substrate may be disposable and the sense units 2000 may be reusable. In one embodiment, sense units 2000 may be manufactured directly on the compliant substrate. In some embodiments, sense units 2000 on compliant substrates may prevent or limit the sense units 2000 from necking. Necking, created by the Poisson effect, may cause sense units 2000 to deform unevenly when stretched along an axis.

For example, when a multi-region strain sensor, having multiple strain units and no compliant substrate, is stretched along a horizontal axis the multi-region strain sensor may deform to be thinner at the center and thicker at each end. In some embodiments, a multi-region strain sensor with a compliant substrate that is stretched along a horizontal axis may deform substantially evenly and have a similar width at the center and ends.

In one embodiment, sense units 2000 coupled to an adhesive tape may be used on human joints to measure joint angle, as well as provide benefits of conventional elastic therapeutic taping. Sense units 2000 may be stretched and measure joint angles, for example when placed over a knee joint (at the knee cap) or top of the thigh. Sense units 2000 may be bent and measure joint angles, for example when placed at the side of the knee or side of the hip. In embodiments, angles may be measured by angular displacement unit or strain units.

In some embodiments, sense units 2000 A though F illustrate sense units with different electrode patters on adhesive tape. In embodiments, different electrode patterns, for example the electrode pattern of sense unit 2000D, may help prevent necking. In some embodiments, different electrode patterns, for example the electrode pattern of sense unit 2000E, may be used to sense stretch or bend. In other embodiments, other electrode patterns, for example sense unit 2000F, may be used to sense angular displacement. The sense unit on the far right may be an example of sense unit 2000F in a bent position. One sense element is positively strained and the capacitance increases, while the other sense element is negatively strained and the capacitance decreases. In embodiments, a differential capacitance measurement may be indicative of the angular displacement.

Figure 21:
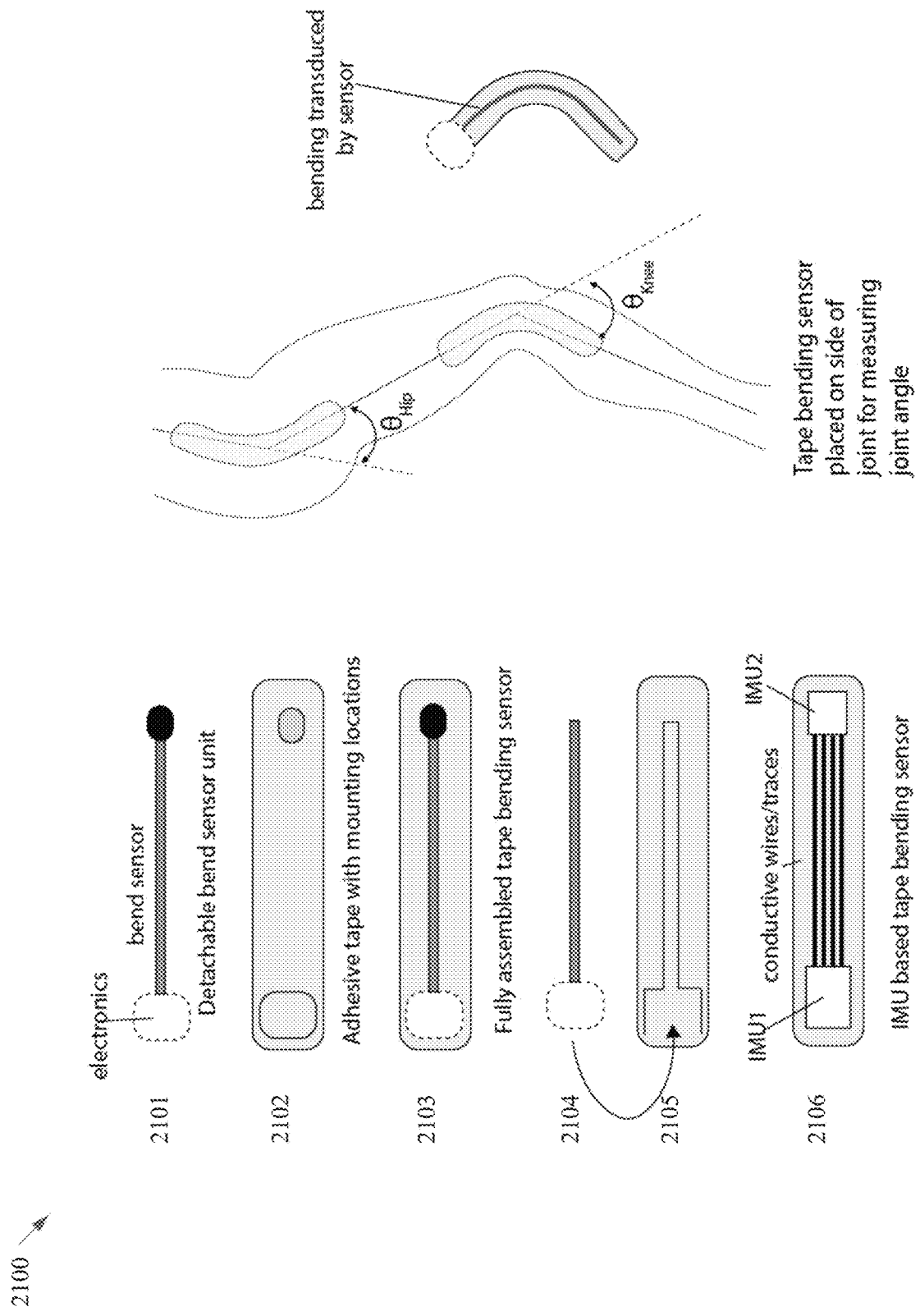
FIG. 21 illustrates a single sense unit or multi-region sensor on a flexible substrate, in accordance with another embodiment.

FIG. 21 illustrates a single sense unit or multi-region sensor on a flexible substrate, in accordance with another embodiment. For the sake of simplicity, sense unit 2101 and 2104 may refer to a single sense unit or multi-region sensor. It may be noted that any sense unit, such as force sensor unit, angular displacement unit, haptic actuator unit, strain unit, or otherwise, may configured in a similar manner as described with respect to FIG. 21.

In embodiments, sense units, such as sense units 2101 and 2104 and associated electronics, may be removed from the compliant substrate, such as adhesive tape. For example, sense unit 2101 may attach to adhesive tape 2102. In some embodiments, adhesive tape 2102 or 2105 may include one or more mounting locations where a sense unit 2101 or 2104 may be secured to adhesive tape 2102 or 2105. Element 2103 shows a fully assembled sensor including sense unit 2101 and associated electronics secured to adhesive tape 2102. In another example, sense unit 2104 may be assembled to adhesive tape 2105 using a pocket design. Sense unit 2104 may slide into adhesive tape 2105. It may be noted that multiple configurations may be used so that a sense unit may be removed from a compliant substrate.

In embodiments, element 2106 shows two inertial measurement units (IMU) connected by conductive traces on a compliant substrate. The IMUs and/or conductive traces may be removable or not removable from the compliant substrate.

Figure 22:
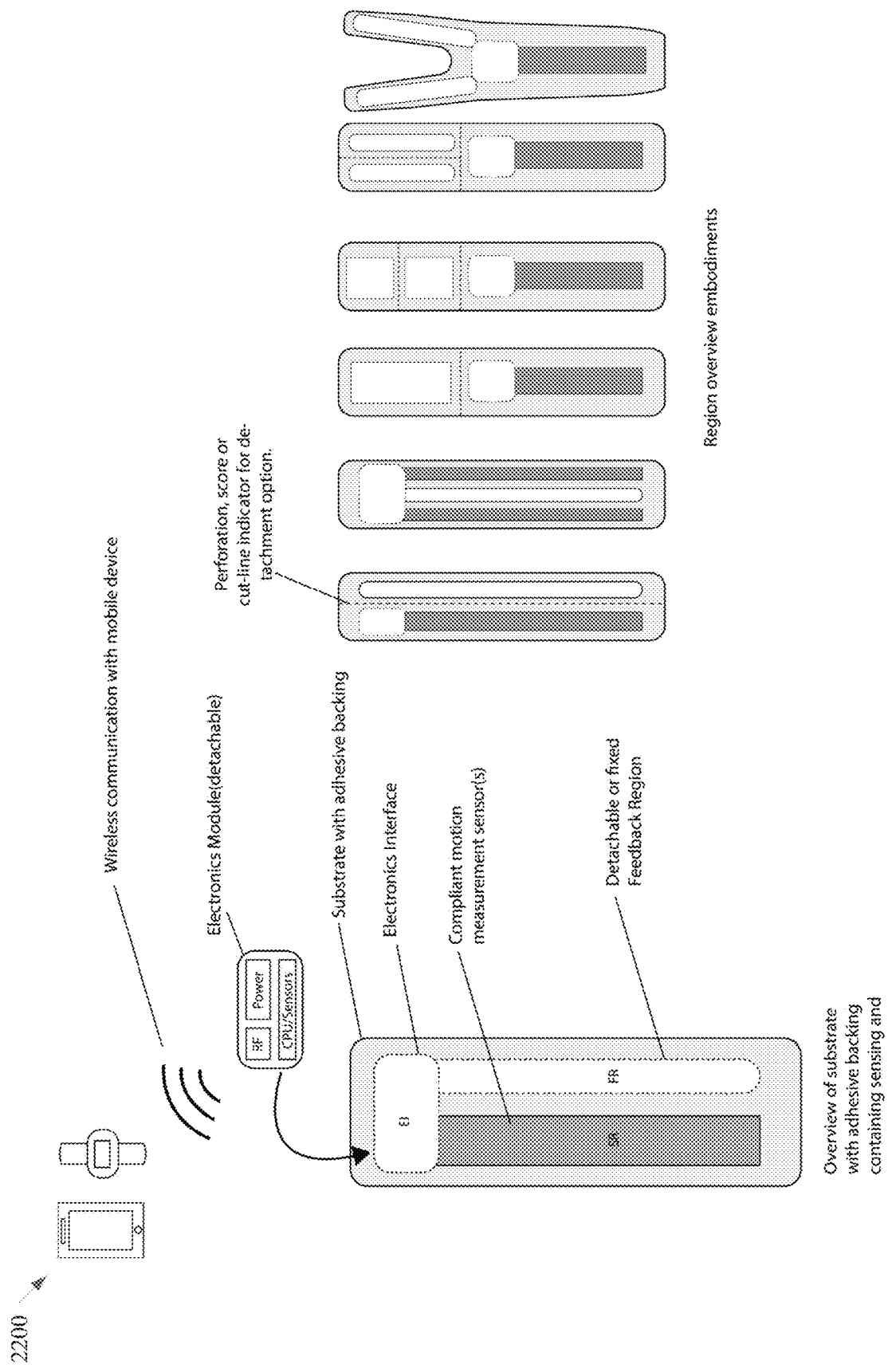
FIG. 22 illustrates one or more sense units or multi-region sensor on a flexible substrate of a motion measurement system, in accordance with another embodiment

FIG. 22 illustrates one or more sense units or multi-region sensor on a flexible substrate of a motion measurement system, in accordance with another embodiment. For the sake of simplicity, the sense units illustrated may refer to a single sense unit or multi-region sensor. It may be noted that any sense unit, such as force sensor unit, angular displacement unit, haptic actuator unit, strain unit, or otherwise, may configured in a similar manner as described with respect to FIG. 22.

In an embodiment, system 2200 shows sense units coupled to an adhesive substrate (also referred to as "tape sensors" herein) with an electronics interface (EI) to house or interface with an interface device. In an embodiment, the sense region (SR) may include one or more sense units and be detachable or non-detachable regions. In some embodiments, the sense regions may include a strain unit or angular displacement unit. In embodiments, the tape sensors may also include feedback regions (FB), which may also be detachable or non-detachable regions. In embodiments, the feedback regions may include sense units as described herein, as well as additional sense units, such as those that provide tactile sensation or biofeedback (e.g., haptic actuator units, vibrating sensor, heat sensor, light sensor, acoustic sensor, pressure sensor, biofeedback sensor, such as heart rate, sweat, respiration, or other biometrics). In embodiments, the dotted lines can signify perforation for easy region detachment. Additional embodiments are shown for measuring joints with more than one degree of freedom, as well as additional locations for feedback regions.

Figure 23:
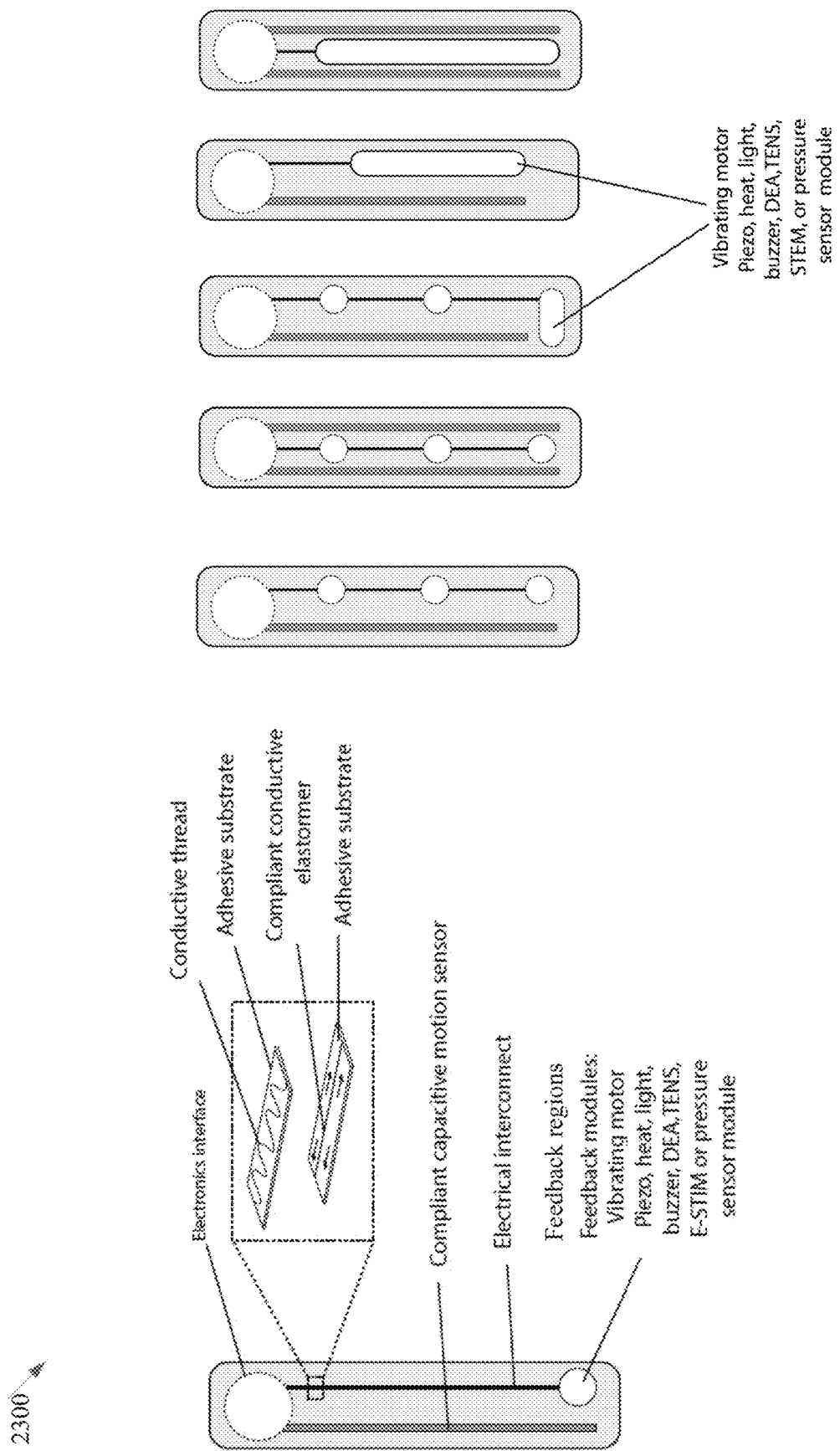
FIG. 23 illustrates one or more sense units or multi-region sensor on a flexible substrate of a motion measurement system, in accordance with another embodiment.

FIG. 23 illustrates one or more sense units or multi-region sensor on a flexible substrate of a motion measurement system, in accordance with another embodiment. For the sake of simplicity, the sense units illustrated may refer to a single sense unit or multi-region sensor. It may be noted that any sense unit, such as force sensor unit, angular displacement unit, haptic actuator unit, strain unit, or otherwise, may configured in a similar manner as described with respect to FIG. 23.

In embodiments, system 2300 shows sense units coupled to an adhesive substrate with an electronics interface (EI) to house or interface with an interface device. In an embodiment, the sense region (SR) may include one or more sense units and be detachable or non-detachable regions. In some embodiments, the sense regions may include a strain unit or angular displacement unit. In embodiments, the tape sensors may also include feedback regions (FB). System 2300 may be similar to system 2200 of FIG. 22. In embodiments, system 2300 may include stretchable power and data transmission elements. Note that inextensible conductive threads may be made compliant by using a wavy or zig-zag stitching pattern, in embodiments.

In some embodiments, tape sensors may be used for measuring joint angle, breathing, swelling, or other parameters. In other embodiments, the feedback regions may include biofeedback mechanisms, such as injecting electrical current (e.g. electrical stimulation (ESTIM) vibro-tactile feedback (e.g., dielectroactive elastomer actuator (DEA)), auditory feedback, or others. For example, some tape sensors may wirelessly communicate with the electronics unit (which may be fully integrated or detachable from the tape) and measure joint position in one location (e.g. over the knee) and provide biofeedback in another location (e.g. over the hamstrings tendon).

Figure 24:
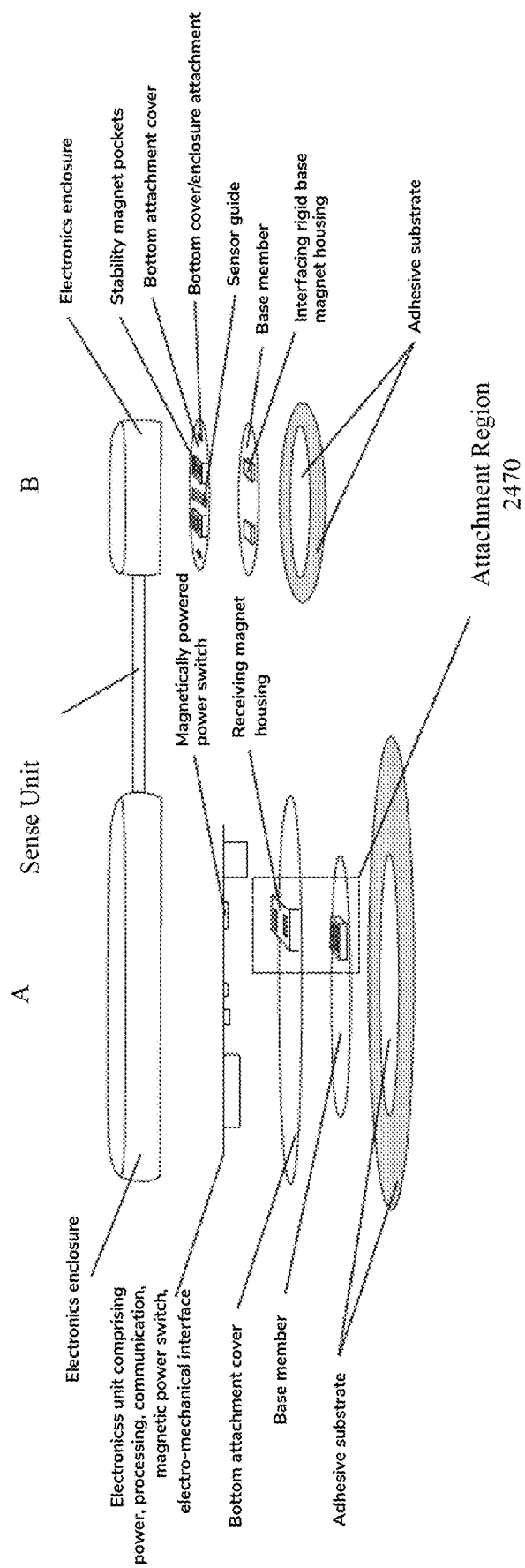
FIG. 24 illustrates stack-up of a tape sensor of a motion measurement system, in accordance with another embodiment.

FIG. 24 illustrates stack-up of a tape sensor 2400 of a motion measurement system, in accordance with another embodiment. For the sake of simplicity, the sense units illustrated may refer to a single sense unit or multi-region sensor. It may be noted that any sense unit, such as force sensor unit, angular displacement unit, haptic actuator unit, strain unit, or otherwise, may configured in a similar manner as described with respect to FIG. 24.

In embodiments, tape sensor 2400 may include an electronics enclosure to house electronics, such as a power source (e.g., battery), processing device (e.g., capacitive measuring circuit or central processing unit or ASIC), an IMU an ADC, communication device (e.g., transmitter, antenna, etc.), switches (e.g., power on/sleep/off switch), or electro-mechanical interface. In embodiments, the electronics may be sealed with the electronics enclosure with the attachment cover A. In embodiments, the seal between the electronics enclosure and attachment cover A may be air tight, water resistant, or water proof. The electronics enclosure may include the electronics enclosure and the attachment cover A hereinafter, unless otherwise described.

In embodiments, an attachment enclosure is coupled to the electronics enclosure with one or more sense units. In embodiments, the attachment enclosure may couple to an attachment cover B and seal the contents in a similar matter as electronics enclosure and the attachment cover A. In embodiments, attachment cover B may contain a sensor guide or stability magnet regions. Some or all the aforementioned elements of tape sensor 2400 may be considered a detachable sensor, herein after.

In embodiments, adhesive substrates A and B may removably adhere to a surface such as a human body. The adhesive substrates A and B may be an exterior surface that attaches to a respective base member. In embodiments, the detachable sensor may detach from the base member, leaving the adhesive substrates A and B and respective base members on the surface on which the adhesive substrate is attached. In embodiments, the attachment covers A and B and base members form an attachment region 2470. It may be noted that attachment region 2470 may be different than attachment region 202, in embodiments. In embodiments, the attachment modalities at the attachment region may be on or more of magnetic, Velcro, glue, zipper, button, among others.

Figure 25:
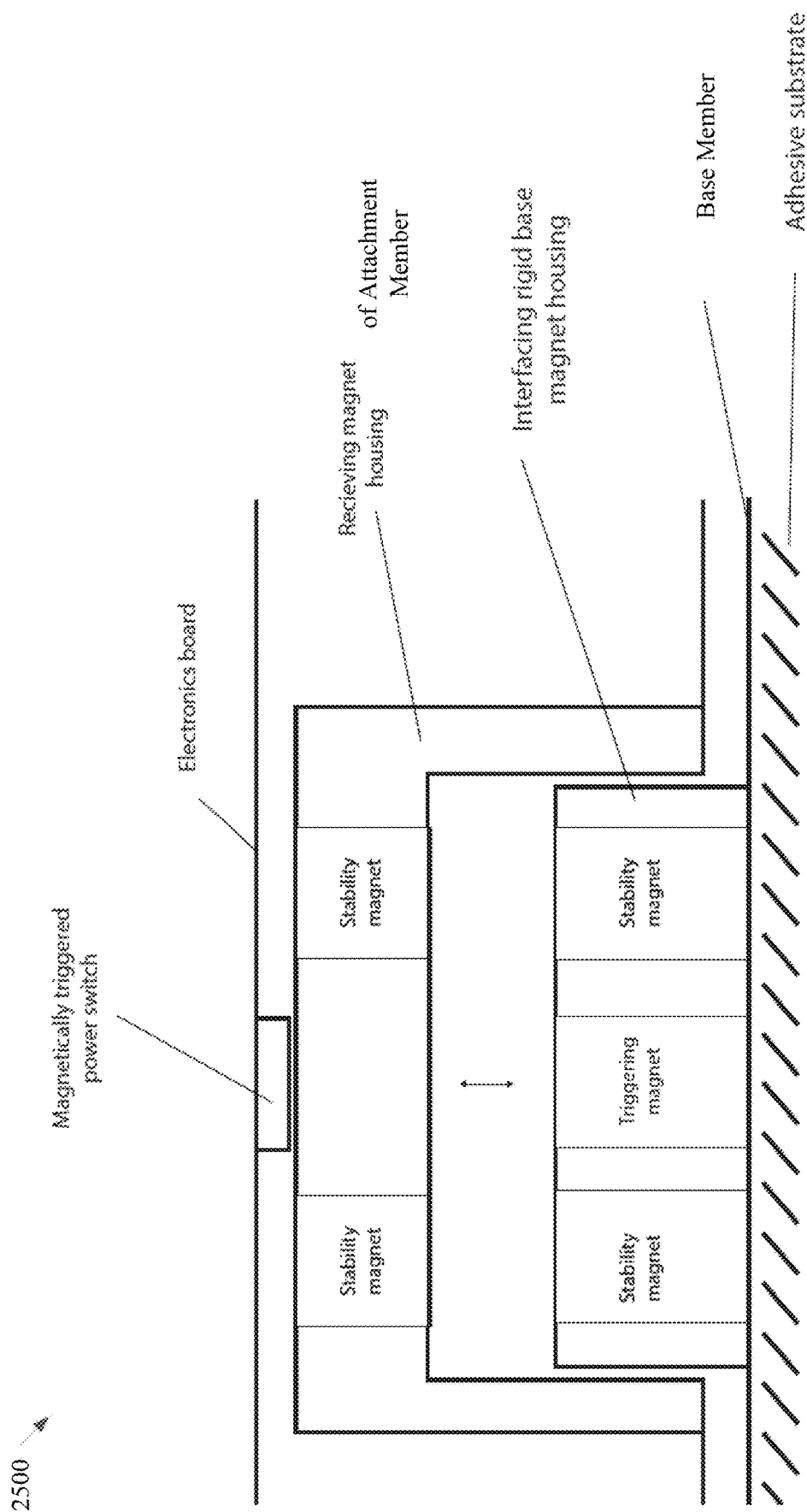
FIG. 25 illustrates an attachment region of the tape sensor of FIG. 24, in accordance with another embodiment.

FIG. 25 illustrates an attachment region of the tape sensor 2400 of FIG. 24, in accordance with another embodiment. Attachment region 2500 may be an example of attachment region 2470 of FIG. 24. In embodiments, attachment region 2500 may include one or more stability magnets. In embodiments, the stability magnets of the base member may be magnetically attracted to the respective stability magnets of the magnet housing of the attachment member. In one embodiment, a proximate magnetic field of the triggering magnet may trigger the power of the detachable sensor to be powered on via the magnetically triggered power switch. In embodiments, detaching the detachable sensor may turn the power off under similar principles.

Figure 26:
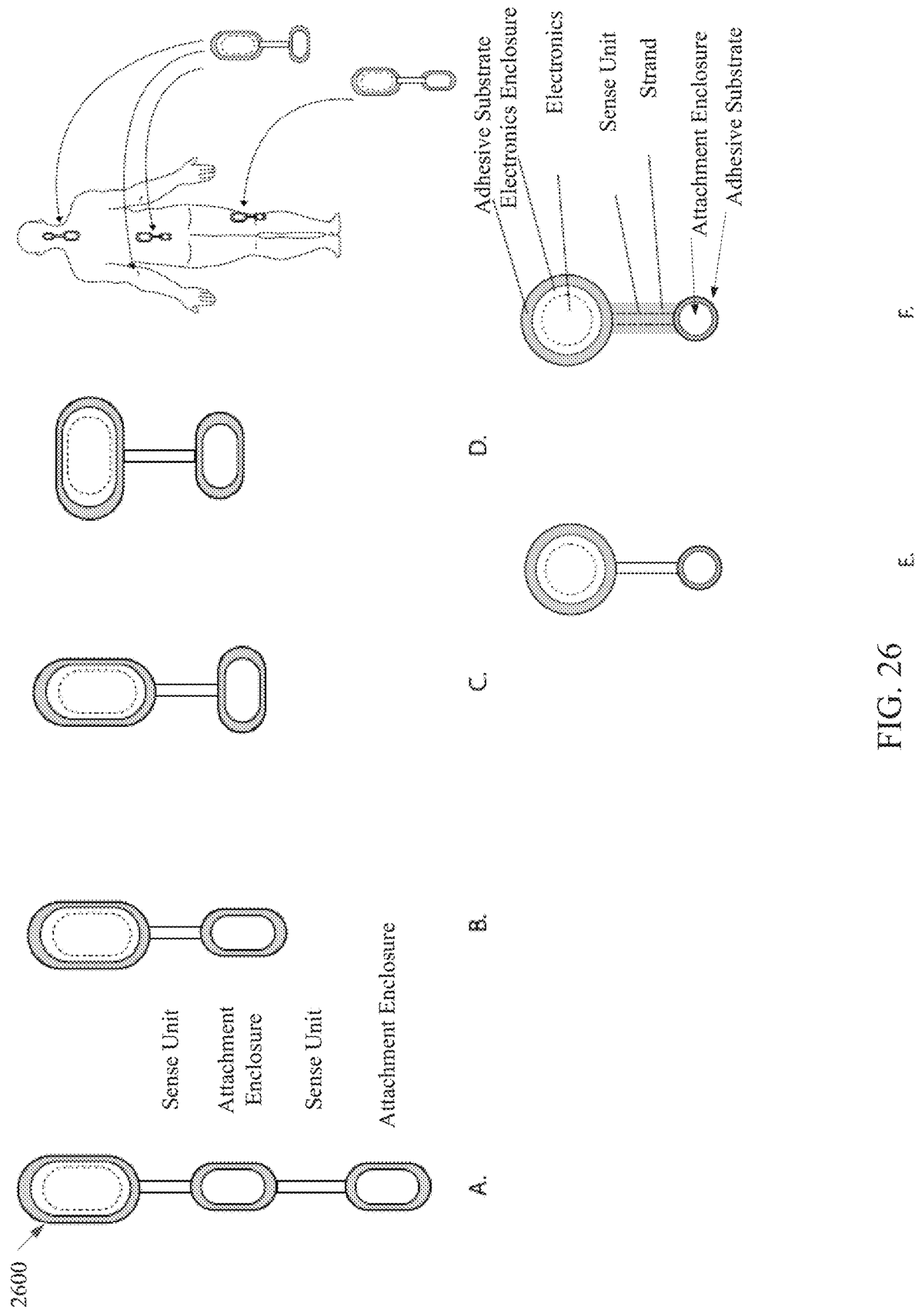
FIG. 26 illustrates tape sensors with different configurations, in accordance with another embodiment.

FIG. 26 illustrates tape sensors 2600 with different configurations, in accordance with another embodiment. For the sake of simplicity, the sense units illustrated may refer to a single sense unit or multi-region sensor. It may be noted that any sense unit, such as force sensor unit, angular displacement unit, haptic actuator unit, strain unit, or otherwise, may configured in a similar manner as described with respect to FIG. 26. Tape sensor 2600 may be similar to tape sensor 2400 of FIG. 24.

In embodiments, tape sensors 2600A-F may contain one or more various elements as illustrated with respect to 2600F. In embodiments, tape sensors may be applied to various locations of the human body, such as across joints to measure angular displacement.

Figure 27:
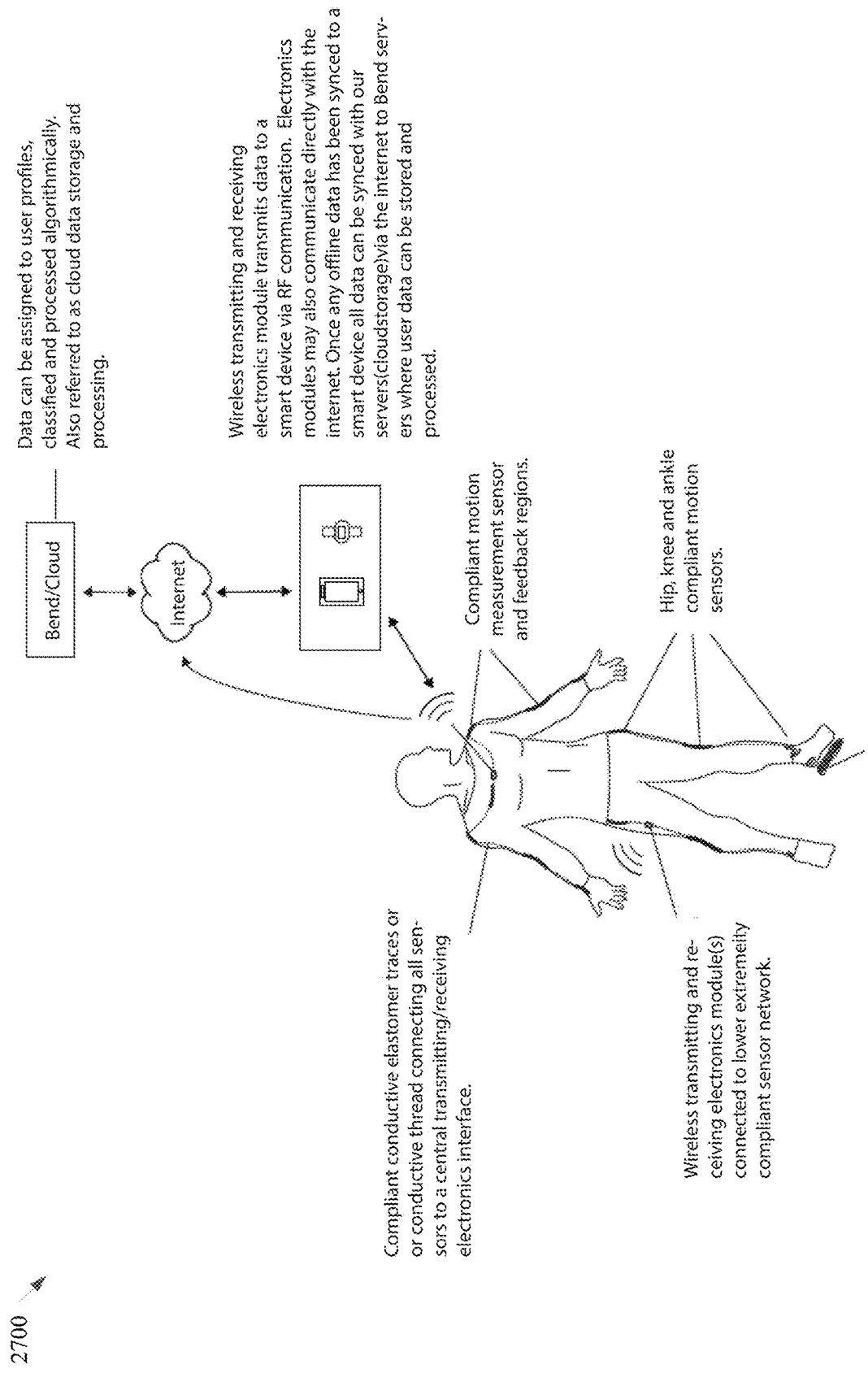
FIG. 27 illustrates a wearable motion measurement system, in accordance with some embodiments.

FIG. 27 illustrates a wearable motion measurement system, in accordance with some embodiments. System 2700 shows different embodiments of sense units integrated into wearable clothing or devices, along with associated electronics, conductive traces, associated mobile devices (e.g., user device), and internet-based communications. In embodiments, system 2700 can be used for measuring a number of motions and physiological functions and processes. For the sake of simplicity, the sense units illustrated may refer to a single sense unit or multi-region sensor. It may be noted that any sense unit, such as force sensor unit, angular displacement unit, haptic actuator unit, strain unit, etc. may be used with elements of FIG. 27.

Systems for measuring human motion are ubiquitous to numerous fields, such as biomechanics, medicine, athletic performance, computer animation, gaming or others. Measuring human kinematics (i.e. motion) may be performed using multi-camera video based systems using marker based tracking, and depth camera based methods that do not require markers. Although such systems can be highly accurate, they may either be expensive or require dedicated motion capture facilities (e.g. marker based motion capture) or are less accurate and require the user to be located directly in front of a camera system. A large number of circumstances and applications (e.g. medical, athletic, gaming, etc.) are not conducive to being located in front of an image based capture system.

A number of alternative systems utilize one or more sensors for measuring the kinematics of a single joint, joint system, or the entire body. Such systems may be integrated into a garment, brace, piece of clothing or similar article that can be placed on the body. Such systems may consist of a motion sensor, such as one or more IMU's (inertial measurement units consisting of accelerometers, gyroscopes and magnetometers and a sensor fusion algorithm) or plastic film-based flex sensors, and metallic-based electrically conductive leads, which is connected to additional electronics such as a microcontroller, a power supply (typically battery-based), RF transceiver, and other electronics, which may either be directly integrated into the garment or a detachable electronics module. However, such systems may have a number of significant drawbacks. For example, motion sensors, such as fiber optic bending sensors, resistive ink based thin film sensors, resistive wire based bending sensors, microelectromechanical (MEMS) based motion sensors such as IMU's, amongst others, are generally too rigid or stiff to be easily integrated into the soft, flexible and stretchable garment fabrics. Such systems may also consume too much power to be practical for wearable applications. Furthermore, creating electrical interconnects between such sensors and the other system electrical components may use wires, which do not easily integrate into fabric.

Aspects of the present disclosure address the above challenges and others by providing a wearable motion measurement system 2700 that implements compliant sensors and networks.

In one embodiment, system 2700 includes compliant sensors, such as capacitive angular displacement sensors (e.g., angular displacement units or bending sensors), stretching sensors (e.g., strain units), pressure sensors (e.g., force sensor units) and surface bio-potential sensors that are soft, flexible, and seamlessly integrate with garment fabrics. In embodiments, the compliant sensors are electrically connected to electronics or each other using compliant electrical interconnects or stretchable patterning of conductive thread. Interconnects or thread may transmit sensor signals, data, or power for system 2700. In embodiments, system 2700 may be partially or wholly integrated into garments, integrated into a fabric, or be a compliant insert that can then be readily attached (or detached) to the garment. In some embodiments, the compliant sensors herein may measure joint angles accurately and with very low power consumption. In other embodiments, additional parameters may also be measured, such as respiration, the fit of clothes, contact forces (such as foot pressure), or others.

In embodiments, system 2700 may use wireless data or power transfer between the compliant sensors and external electronics. In other embodiments, system 2700 may use electrical connections, such as compliant traces, to transmit power or digitally encode data over the power supply voltage. In some embodiments, power is harvested from an RF field, and data is transferred either from the same charging RF field (as in Near Field Communication, NFC), or through another RF based means (e.g. Bluetooth). In some embodiments, an external device (e.g. a small electronics module or an NFC enabled phone) may power the compliant sensors or associated electronics and facilitate data transmission. In some embodiments, all or some of the electronics may be fully sealed and require no battery.

In some embodiments, an electronics module, which has at least two exposed electrical contacts, is attached to the clothing (e.g. slid into a small pocket) and makes electrical contact with conductive leads on the fabric (e.g. made from conductive elastomer, conductive spandex or threads), to transfer power and data. In embodiments, data is transmitted digitally by superimposing an AC signal on the DC power supply (e.g. using 1-wire protocol). In embodiments with two contact points and digital data transfer, bulky assemblies to align connections and prevent noise may be eliminated. Other embodiments may include three wire approaches (+V, ground and Tx lines), and could also include four wire approaches (e.g. I2C) or five wire approaches (SPI).

In one embodiment, system 2700 includes an insert that includes some or all of complaint sensors, leads, and associated electronics. In some embodiments, the insert may be sealed within a waterproof barrier and on a substrate (e.g. spandex fabric or an elastomer membrane) that can easily be attached to a garment using conventional sewing, laminating, adhesives, snaps or heat press equipment. In embodiments, an insert may contain a number of compliant sensors, wireless power, or data transmission electronics, and provide a motion measurement solution that is easy to be integrated into existing manufacturing methods.

In some embodiments, the inserts may contain specific compliant sensors or groups of compliant sensors, which may then connect to the central electronics for the garments either with compliant leads or conductive threads sewn into the fabric. In another embodiment, a number of biofeedback mechanisms, such as compliant electrodes for muscle stimulation via electric current, vibrating sensors, audible buzzers and similar devices may be included in the system. In embodiments, compliant sensors that measure strain, angular displacement, or compressive force may be combined with additional electronics, such as low power MUC's (microcontrollers), or further combined with RF data transfer or RF power transfer to form an integrated system for measuring motion, gestures, and providing training and feedback.

In some embodiments, system 2700 may include one or more sensing regions. In embodiments, system 2700 may be have one or more sensing regions having sense units capable of measuring movement, compressive force, stretch, bend, surface bio-potential, or deliver tactile sensation, such as vibration, electrical or other. In embodiments, system 2700 may also include a transmission region where signals and/or power are transmitted via elastomeric, wire, or thread conductors. In embodiments, system 2700 may include a communication region where data is exchanged between sensing regions and external electronic devices (e.g. cell phone or separate electronics module). In embodiments, the communication regions may include an electromechanical interface, analog and digital signal processing, a power storage module (e.g. supercapacitor), a physical electrical connection, or RF connection for transmitting power and data. In embodiments, system 2700 may include a storage region such as a connecting pocket or apparatus that allows for an external electronics device (e.g. smart phone or dedicated electronics system) to be mechanically coupled to the garment and may or may not include wired electrical connections.

Figure 28:
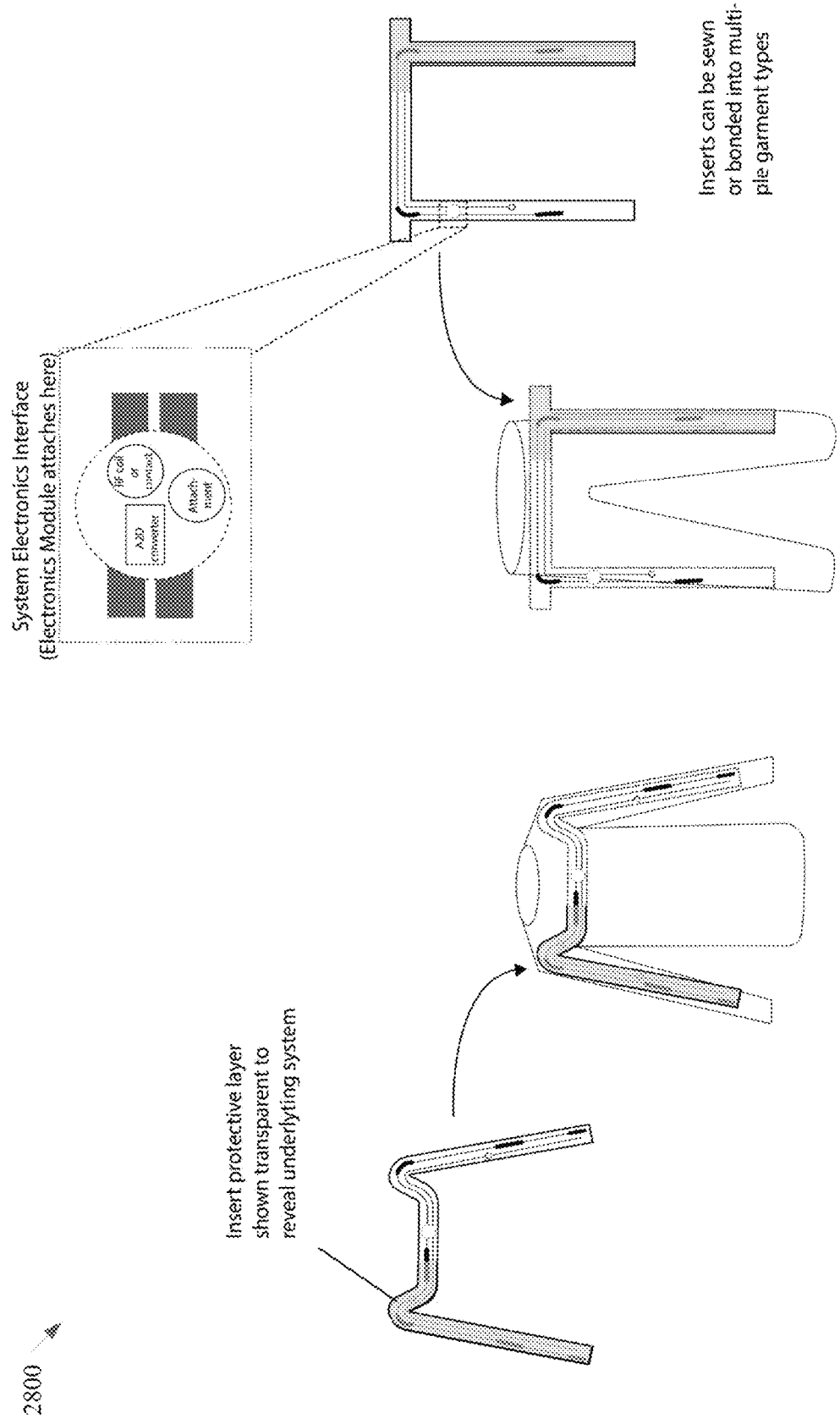
FIG. 28 illustrates inserts of a wearable motion measurement system, in accordance with another embodiment.

FIG. 28 illustrates inserts of a wearable motion measurement system, in accordance with another embodiment. System 2800 shows a motion measurement insert system for a shirt and pants, where multiple sense units measure joint angles and are electrically connected to the system electronics interface, which may include integrated or detachable components such as an AD converter, analog electronics, digital electronics and RF based communications and power, as well as possible power supplies such as batteries and ultra capacitors. For the sake of simplicity, the sense units illustrated may refer to a single sense unit or multi-region sensor. It may be noted that any sense unit, such as force sensor unit, angular displacement unit, haptic actuator unit, strain unit, etc. may be used with elements of FIG. 28.

Figure 29:
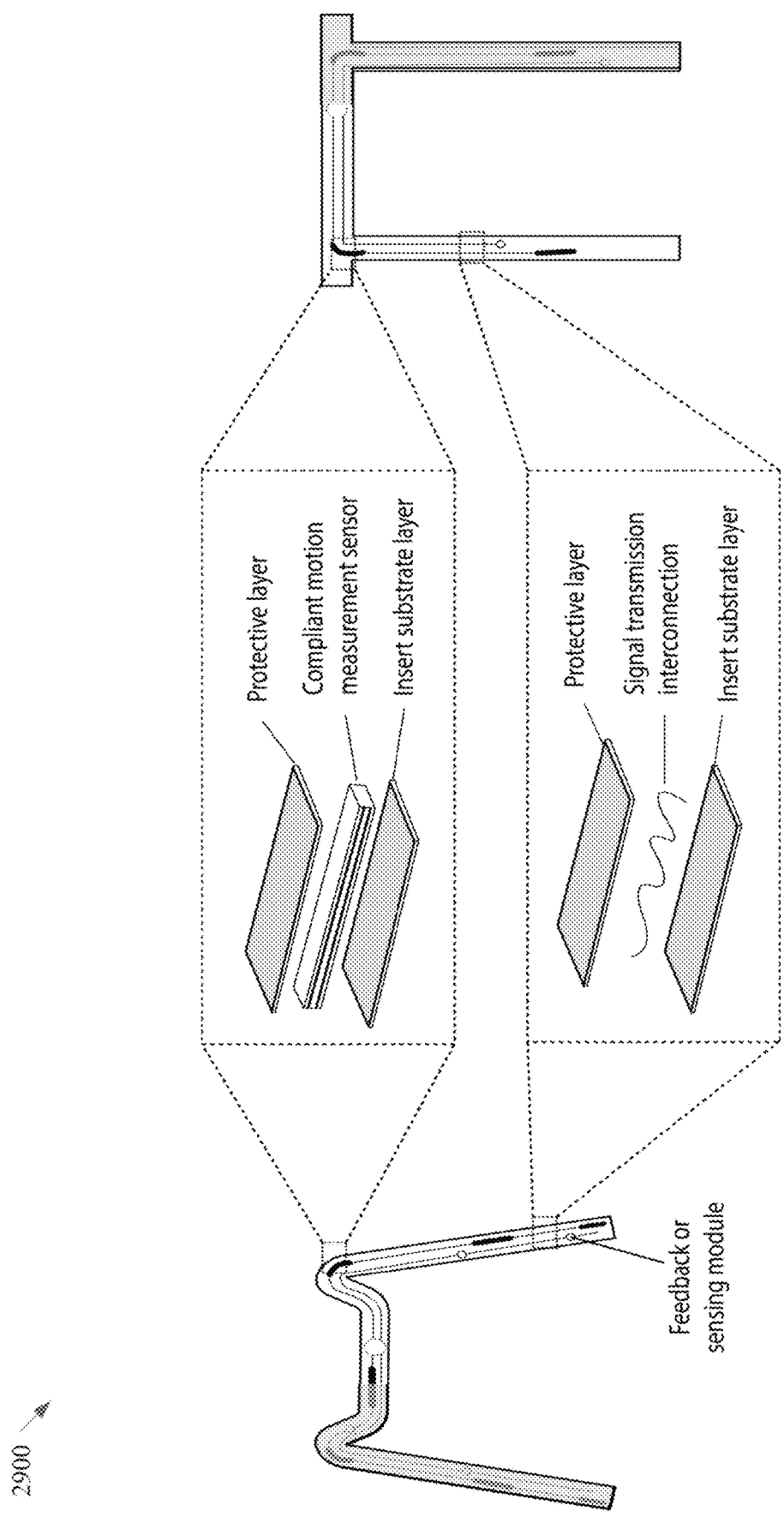
FIG. 29 illustrates inserts of a wearable motion measurement system, in accordance with an embodiment.

FIG. 29 illustrates inserts of a wearable motion measurement system, in accordance with an embodiment. System 2900 shows complaint sensor based motion measurement system, showing protective and substrate layers, as well as signal transmission interconnects. In embodiments, the insert may be water resistant or water proof. System 2900 also illustrates feedback sensors for providing biofeedback via current, vibration, heat or other means.

Figure 30:
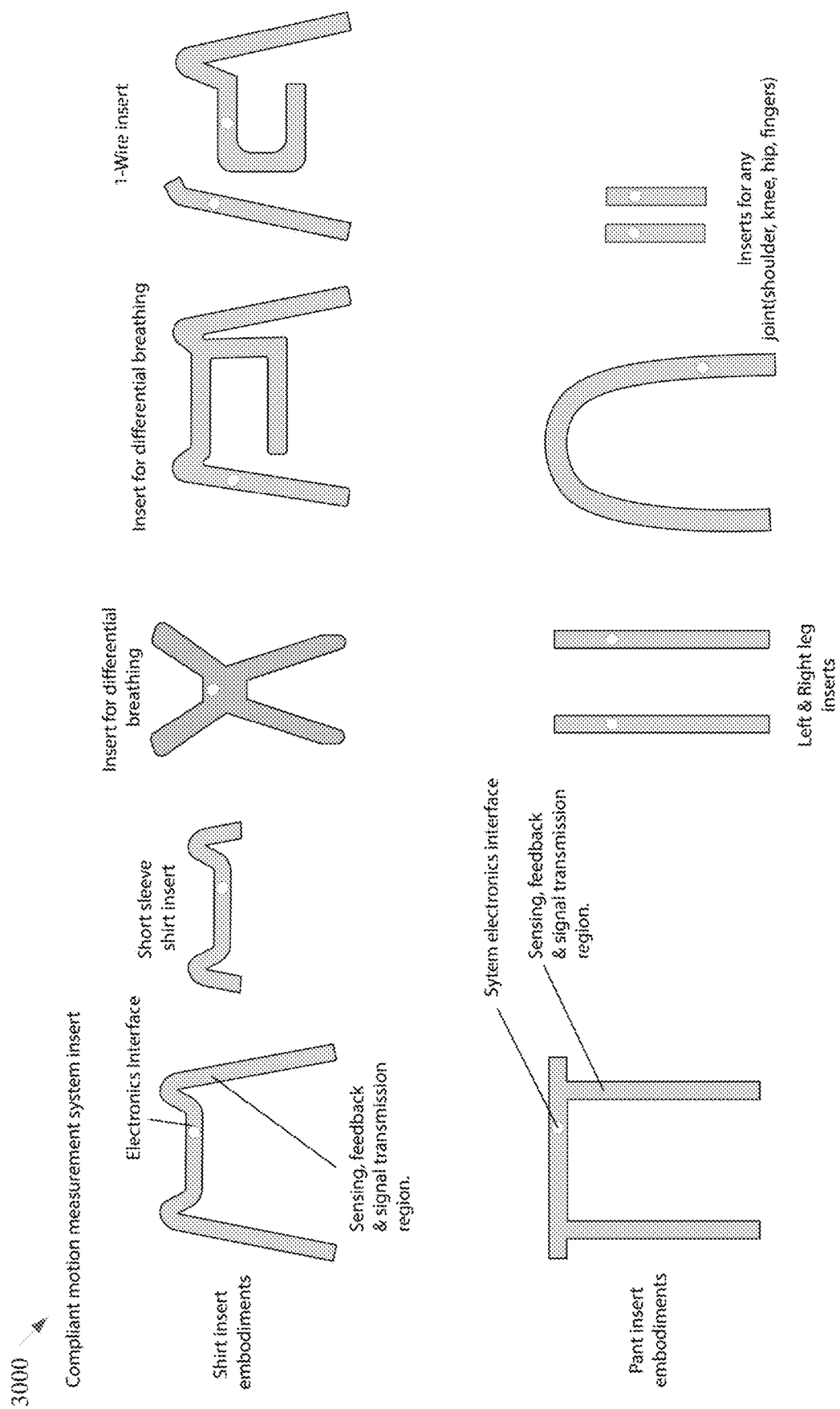
FIG. 30 illustrates inserts for a motion measurement system, in accordance with embodiments.

FIG. 30 illustrates inserts for a motion measurement system, in accordance with embodiments. System 3000 shows different embodiments of the compliant inserts with one or more compliant sensors. In embodiments, the inserts include inserts for full shirt, short sleeve shirt, respiration monitoring, pants, individual joints, or others.

Figure 31:
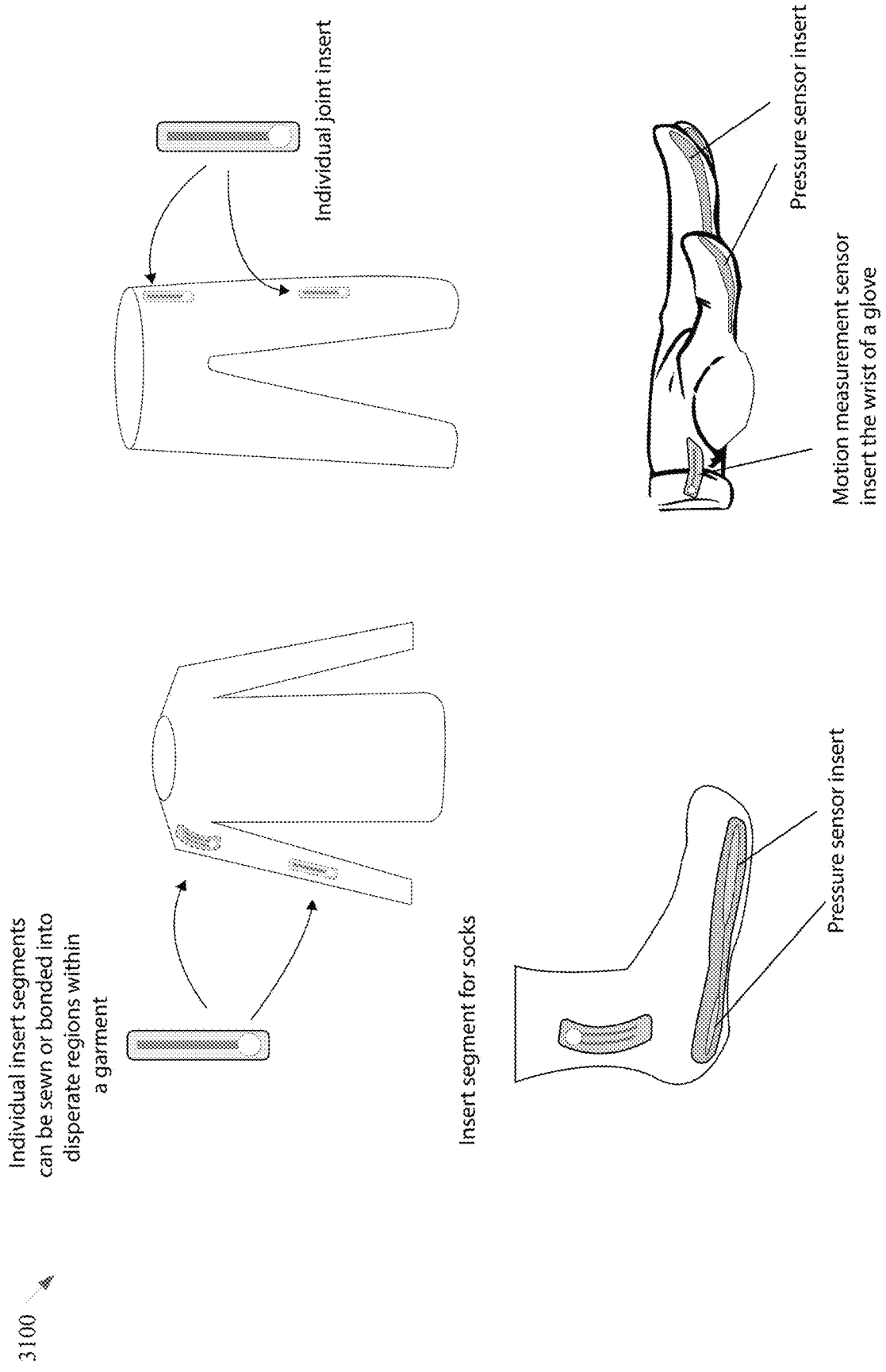
FIG. 31 illustrates inserts for a motion measurement system, in accordance with other embodiments.

FIG. 31 illustrates inserts for a motion measurement system, in accordance with other embodiments. System 3100 shows additional embodiments of inserts with compliant sensors or integration of compliant sensors with fabric and garments. For example, system 3100 show inserts in individual joint inserts in a shirt and pants, inserts in a sock, and inserts for a glove. In one embodiment, inserts may include inserts on the underside of the glove for measuring pressure (e.g., compressive force) and inserts on the top and between fingers of the glove for measuring finger and wrist motion and position.

Figure 32:
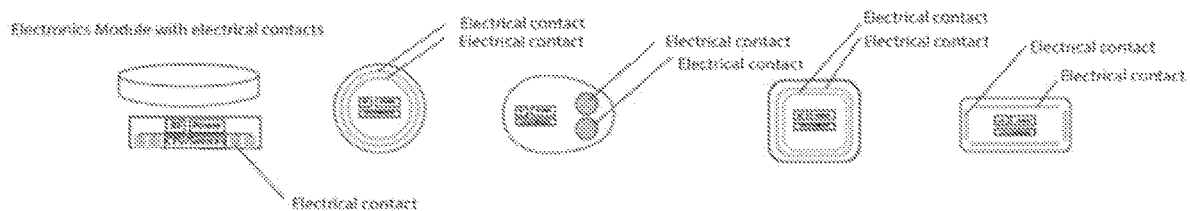
FIG. 32 illustrates an interface component of a motion measurement system, in accordance with an embodiment.
Figure 32:
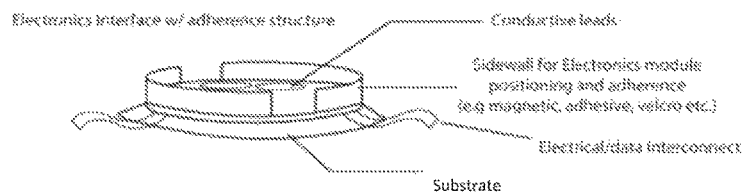
Figure 32:
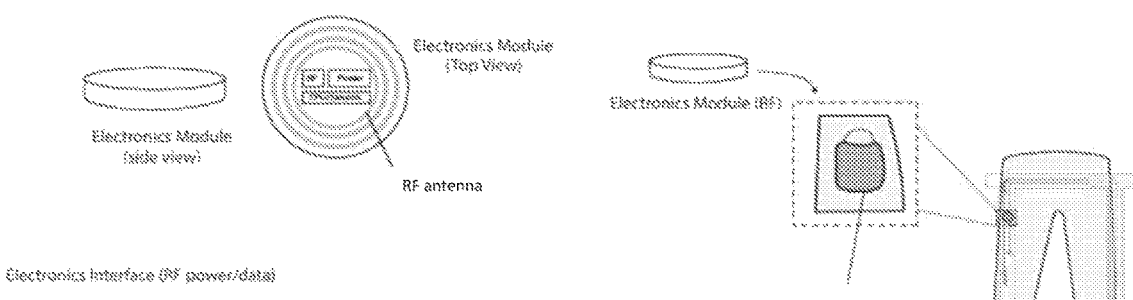
Figure 32:
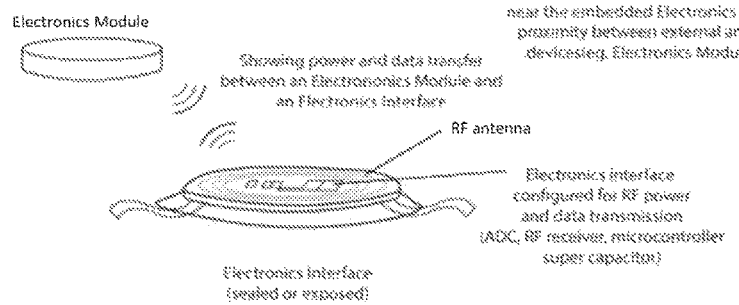

FIG. 32 illustrates an interface device of a motion measurement system, in accordance with an embodiment. System 3200 shows electronics for compliant sensor motion measurement system, including an electronics module that may be fully integrated or detachable, as well as having RF antennas for both communication and power transfer between the electronics and insert as well as between the electronics and an external device.

Figure 33:
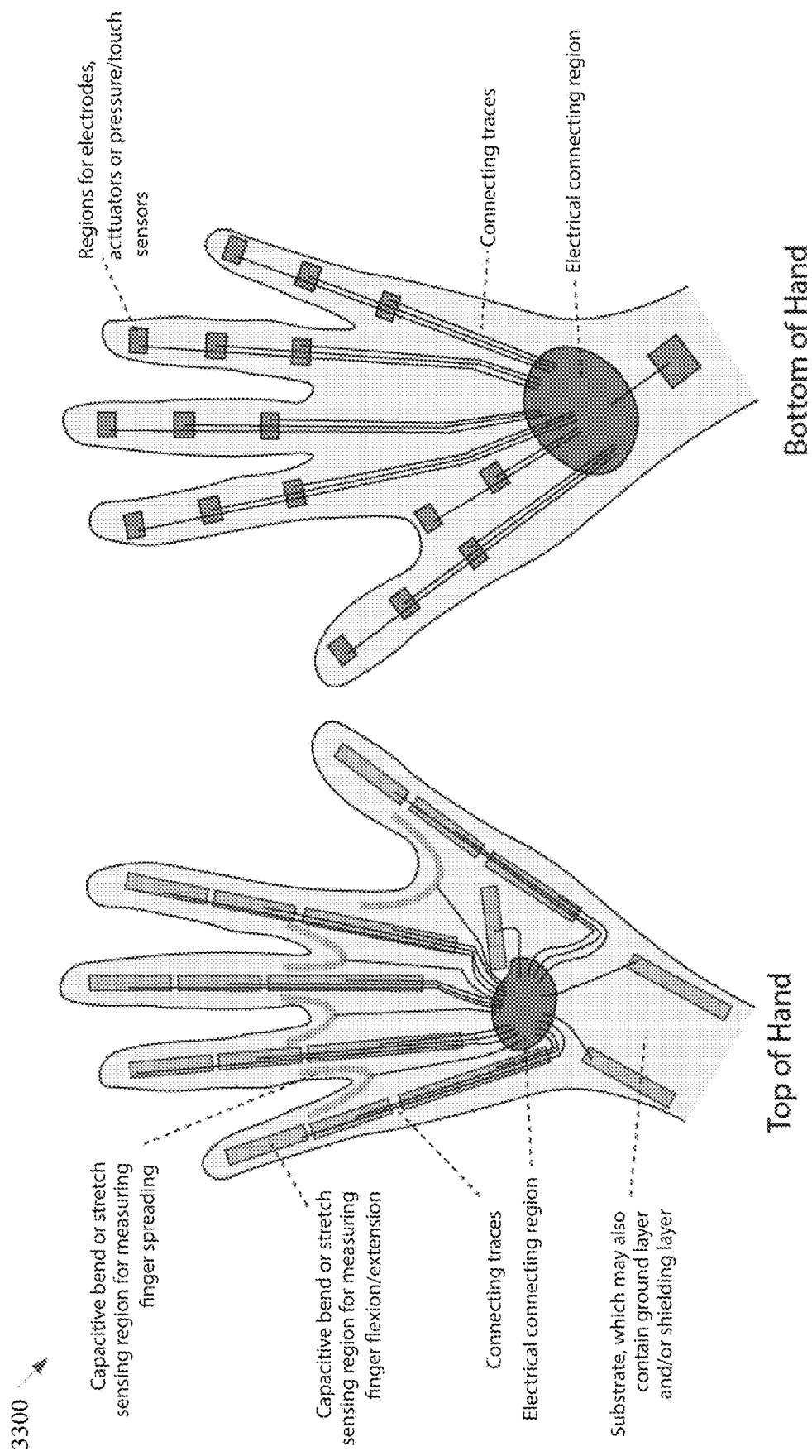
FIG. 33 illustrates a compliant sensor network, in accordance with one embodiment.

FIG. 33 illustrates a compliant sensor network 3300, in accordance with one embodiment. In embodiments, multiple multi-region sensors are overlaid on the human hand. The compliant sensor network may be integrated into a glove, for example.

In one embodiment, several multi-region angular displacement sensors are illustrated on the top of the hand and may be used to measure hand and finger motion. In embodiments, one or more fingers may have a multi-region angular displacement sensor to measure the motion of the joints of the finger. In embodiments, the motion of a joint of the hand may be measured independently respective another joint. In embodiments, the sensing regions may be spatially separated. In embodiments, the sensing regions may be connected via conductive traces to an electrical connecting region. In embodiments, the conductive traces may be conductive elastomer traces. In embodiments, one or more of the multi-region angular displacement sensors may be connected to the electrical connecting region. In embodiments, the electrical connecting region may contain or connect to additional sensing electronics. Although one electrical connecting region is shown on the top of the hand, different configurations may be used that include multiple electrical connecting regions.

In embodiments, the compliant sensor network 3300 may also include one or more compliant strain units or angular displacement units in an area between the fingers to measure the movement between the fingers (e.g., to measure finger spreading and contracting). In embodiments, the one or more compliant sensor units in each area between the fingers are coupled to the electrical connecting region with connecting traces, as illustrated.

In embodiments, the compliant sensor network 3300 may also include additional compliant strain units or angular displacement units to measured changes in wrist joint angles and thumb joint angles. Any number of compliant strain sensing elements may be used. In embodiments, the additional compliant strain sensing elements may also be connected to the electrical connecting region using conductive traces.

In embodiments, one or more multi-region haptic actuator sensors (or multi-region force sensors, or both) may be used on the bottom of the hand to provide haptic feedback to a user. In embodiments, multi-region haptic actuator sensors may have one or more sensing regions (also referred to as "actuating regions" or "actuator sensing regions" herein) that include one or more haptic actuator sense elements. For example, a multi-region haptic actuator sensor may have three sensing regions capable of providing haptic feedback to a finger. The sensing regions may be spatially separated and provide independent and varied tactile sensation with varying magnitudes to each sensing region. In embodiments, the haptic actuator units may be interspersed in different sensing regions and connected by conductive traces that connect to the electrical connecting region. It may be noted that haptic actuator units may be interspersed or combined other sense units in any manner. It should also be appreciated that the multi-region angular displacement sensors measuring motion is shown on the top of the hand and the multi-region haptic actuator sensor is shown on the bottom of the hand is used for purposes of illustration rather than limitation. In other embodiments, any configuration of any sense units may be used.

Figure 34:
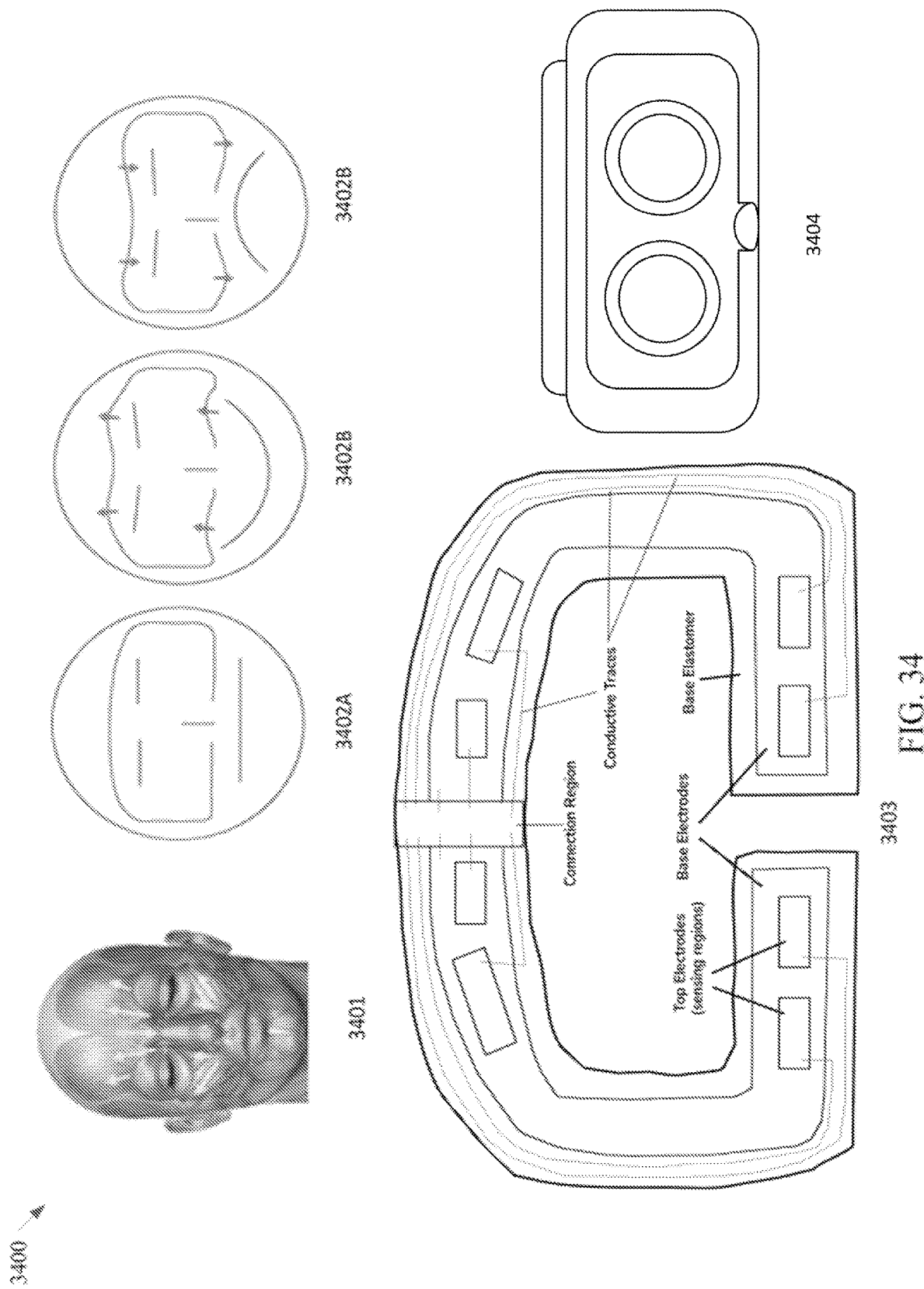
FIG. 34 illustrates a facial expression recognition system using a multi-region strain sensor, in accordance with one embodiment.

FIG. 34 illustrates a facial expression recognition system 3400 using a multi-region strain sensor, in accordance with one embodiment. Head mount display 3404 may be wearable device that makes images visible to the user and/or may allow a user to see through the head mount display. For example, head mount device may be a virtual reality (VR) headset. In embodiments, one or more multi-region strain sensors and/or multi-region angular displacement sensors may be embedded in head mount display 3404, such as in the foam sealing component 3403 of head mount display 3404, to measure facial deformations indicative of facial expressions.

Human face 3401 shows muscles of the face. The arrows show the directions of muscle contractions for facial expressions. The facial expressions 3402A-C show different deformations of a foam sealing component 3403 of a head mounted display 3404 responsive to different facial expressions. In embodiments, the foam sealing component 3403 may deform in response to different facial expressions. Facial expression 3402A shows a neutral face. Facial expression 3402B shows a happy face. Facial expression 3402C shows a sad face. It may be noted that any number of deformations may be measured and any number of facial expressions may be determined.

In embodiments, foam sealing component 3403 shows a multi-region strain sensor embedded in the foam sealing component 3403. In embodiments, the different sensing regions of the multi-region strain sensor may share a compliant substrate, such as an elastomer substrate. In embodiments, the different sensing regions, illustrated by the top electrode, may be spatially separate to sense muscle contractions of different areas of human face 3401. In embodiments, multiple top electrodes may share a single base electrode, or may have individual base electrodes. In embodiments, electrical connections may be formed by conductive traces, such as compliant conductive traces. In embodiments, the conductive traces may attach to a connecting region, which may include a printed circuit board and/or other associated electronics.

Figure 35:
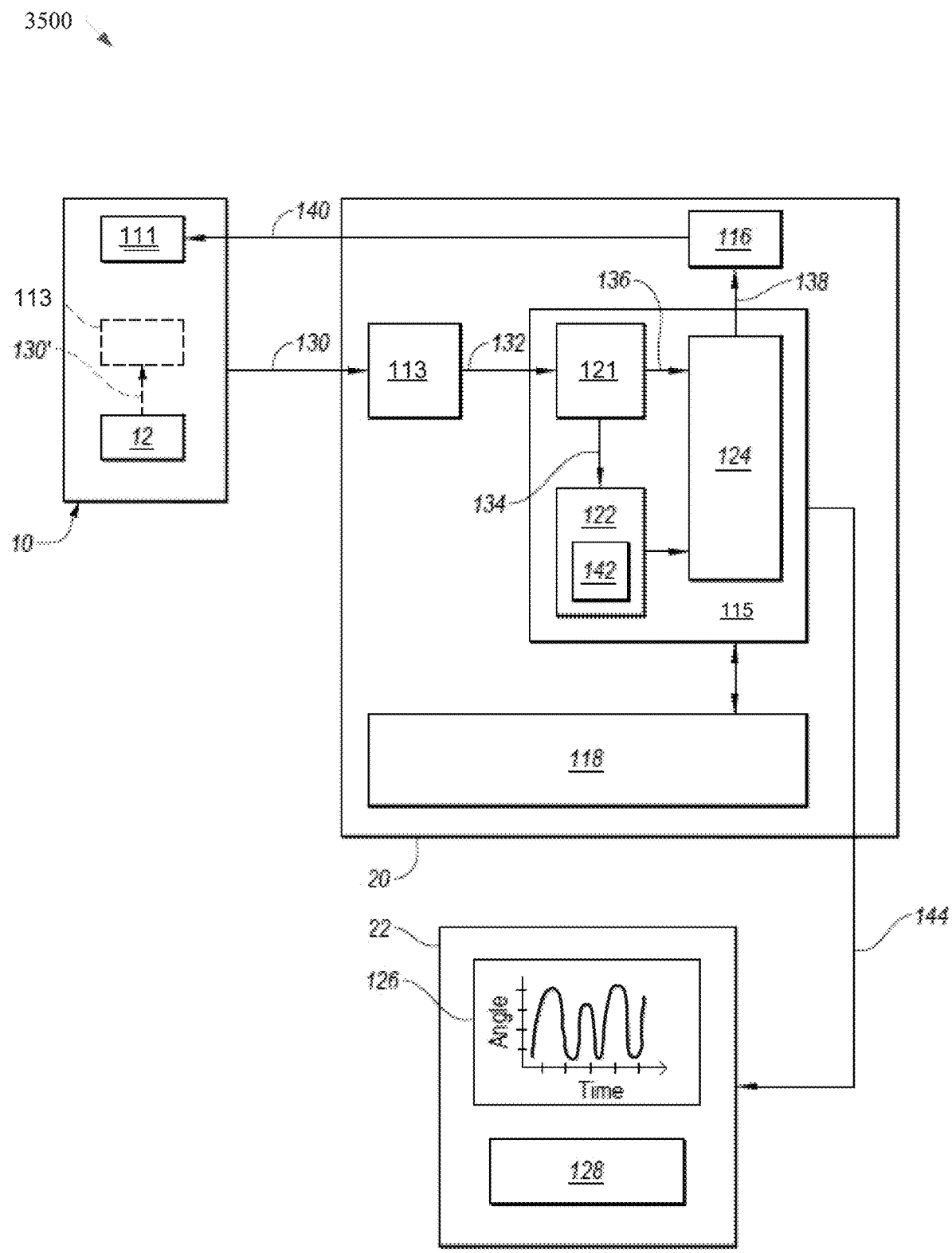
FIG. 35 illustrates a schematic diagram of various components of a system for analyzing data relative to sense units, according to one embodiment.

FIG. 35 illustrates a schematic diagram of various components of a system 3500 for analyzing data relative to sense units, according to one embodiment. In one embodiment, the system 3500 may include the sensor system 10 (e.g., multi-region angular displacement sensor and/or multi-region strain sensor, etc.), the interface device 20 (all or part also referred to as "circuit device", "electronics module", "associated electronics", "electronics", "sensor electronics" herein), and the remote device 22. For purposes of illustration, rather than limitation, the system 3500 may be described as measuring angular displacement. It may be appreciated that system 3500 may be used for other measurements, such as compressive force.

In embodiments, the sensor system 10 may include a sense unit 12 and a biofeedback device 111. The interface device 20 may include a capacitance measurement circuit 113, a micro-controller 115, a biofeedback amplifier 116, or a user interface 118. The micro-controller 115 may include a calculation circuit 121, a memory 122, and control and analysis software 124. The remote device 22 may include a display 126 and user input 128, and may include the processors and computing devices of, for example, a smart phone or personal computer, as known in the art. In other embodiments, the micro-controller 115 may include both analog and digital circuitry to perform the functionality of the capacitance measurement circuit 113, the calculation circuit 121, and biofeedback amplifier 116. In some embodiments, interface device 20 may be a processing device, such as a microprocessor or central processing unit, a controller, special-purpose processor, digital signal processor ("DSP"), an application specific integrated circuit ("ASIC"), a field programmable gate array ("FPGA"), or one or more other processing devices known by those of ordinary skill in the art.

In use, for example, upon bending movement of the sense unit 12 (such as an angular displacement unit), the capacitance measurement circuit 113 measures capacitances of the compliant capacitors. In embodiments, capacitance measurement circuit 113 can be housed in the interface device 20 and coupled to the sense unit 12 via wires, as indicated by arrow 130. In other embodiments, the capacitance measurement circuit 113 may be housed adjacent to or with the sense unit 12 itself (as indicated with dashed arrow 130') or within, for example, one of the first and second members (not shown) coupled to the sense unit 12. It should be noted that the capacitance measurement circuit 113 can measure capacitance between the at least two electrodes of one of the compliant capacitors. In another embodiment, the capacitance measurement circuit 113 may measure a differential capacitance of the two compliant capacitors. In embodiments where sense unit 12 includes the single compliant capacitor, the capacitance measurement circuit 113 can measure a single capacitance between the electrodes of the single compliant capacitor. In embodiments, the capacitance measurement circuit 113 can measure the capacitance(s) or differential capacitance in terms of voltage or current. In embodiments, the capacitance measurement circuit 113 then transmits voltage data or current data to the micro-controller 115, such as to the calculation circuit 121, as indicated by arrow 132.

In embodiments, the calculation circuit 121 calculates the values of the voltage data or current data provided by the capacitance measurement circuit 113 to calculate, for example, the angular displacement between the first and second vectors. The calculation circuit 121 may then transmit angle data to the memory 122 (which then becomes logged data) and the control and analysis software 124, as indicated by respective arrows 134, 136. In one embodiment, parameters may be input as maximum/minimum limits for angular displacement through, for example, the user interface 118. The user interface 118 may include a display and/or a user input, such as input keys. The maximum limits (and minimum limits) may be useful for a user to know once the user has reached a particular angular displacement with the sensor system 10. As such, if the user does meet the desired parameters (or undesired as the case may be), the control and analysis software 124 may transmit a signal to the biofeedback amplifier 116, as indicated by arrow 138, which in turn may transmit a signal back to the biofeedback device 111, as indicated by arrow 140, at the sensor system 10.

In embodiments, the biofeedback device 111 may then produce a notification to the user that a predefined input parameter has been reached, such as the maximum angular displacement, so that the user understands in real-time the limits relative to the movement of the user's particular joint being analyzed, for example. The notification may be at least one of a visual notification, an audible notification, and a tactile notification or some other notification to facilitate the user's understanding of the user's maximum limit. Alternatively, the notification can be any combination of visual, audible and tactile notifications. The visual notification may be in the form of a blinking (or various colored) light or the like displayed on the sensor system 10 itself or the interface device 20 and/or also may be visualized on a display of the interface device 20. The audible notification may be a ring or beep or the like that may preferably be audibly transmitted from the interface device 20, but may also be transmitted from the sensor system 10. The tactile notification may be coupled to or integrated with the sensor system 10 or may be integrated in the interface device 20. Such tactile notification may be in the form of a vibration or some other tactile notification. In this manner, the biofeedback device 111 may notify the user in real time upon extending or contracting ones anatomical joint at a maximum angular displacement according to a predetermined input parameter. Similarly, in another embodiment, a user may input parameters of a minimum angular displacement into the interface device 20 for biofeedback notification. Further, in another embodiment, the user may input parameters for both a minimum angular displacement and a maximum angular displacement. Inputting such parameters may be useful for exercises during physical therapy and for athletes training to obtain particular movements at various anatomical joints.

In embodiments, upon completing a session of rehabilitation therapy or training or the like, for example, logged data 142 may be stored in the memory 122 or storage device of the interface device 20. Such logged data 142 may also be viewable on the interface device 20 on a display at the user interface 118. The logged data 142 may then be transferred to the remote device 22, as indicated by arrow 144. The remote device 22 may be any known computing device, such as a mobile device, smart phone, tablet, personal computer, gaming system, etc. In one embodiment, the logged data 142 may be transferred to a smart phone by, for example, wireless technology (e.g., over a wireless local area network (WLAN) such as a Bluetooth® network or Wi-Fi® network) or transferred via mini-USB ports or the like, as known to one of ordinary skill in the art. In another embodiment, the logged data 142 may be transferred to a personal computer via a port, such as a USB port with, for example, a portable memory device, such as a thumb drive. The user may then save the logged data 142 on the remote device 22 for further analysis. As previously set forth, the user may save several sessions of logged data 142 to the remote device 22 to obtain further analysis and comparison data to better understand, for example, progress or regress in the user's angular displacement of the user's anatomical joints.

Although not illustrated, the elements described in FIG. 35 may be powered by numerous power sources that include one or more of batteries, rechargeable batteries, wired power, capacitive storage, and power scavenging techniques such as radio frequency (RF) power scavenging, among others.

Figure 36:
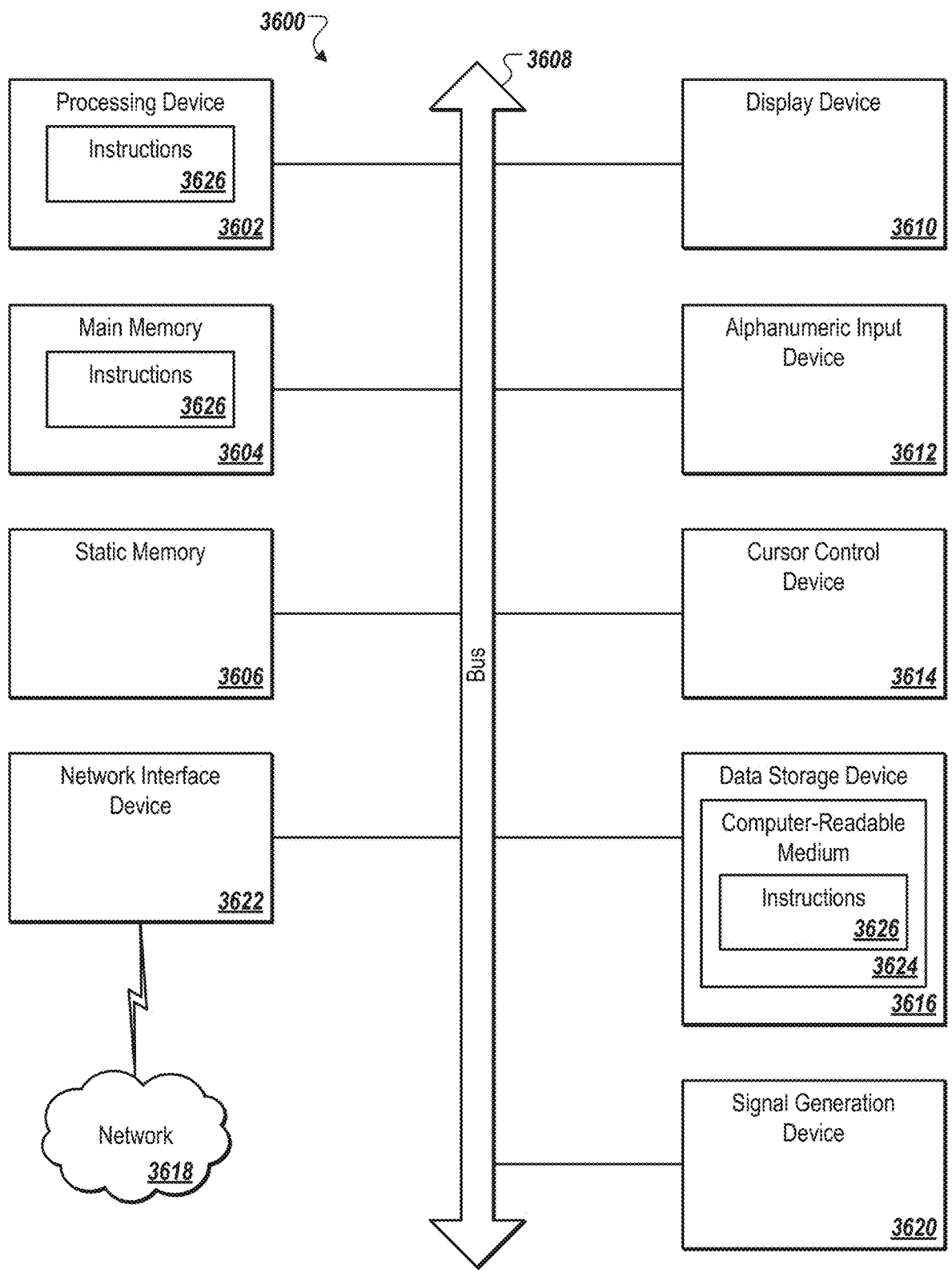
FIG. 36 illustrates a diagrammatic representation of a machine in the example form of a computer system, according to embodiments.

FIG. 36 illustrates a diagrammatic representation of a machine in the example form of a computer system 3600 within which a set of instructions, for causing the machine to perform any one or more of the methodologies discussed herein, may be executed. In embodiments, the computer system 3600 may correspond one or more of elements of FIG. 35, such as interface device 20, remote device 22, or micro-controller 115 that executes the control and analysis software 124.

In embodiments, the computer system 3600 may correspond to an IMU or a computer system in communication with an IMU, as described herein. In embodiments, the machine may be connected (e.g., networked) to other machines in a Local Area Network (LAN), an intranet, an extranet, or the Internet. In embodiments, the machine may operate in the capacity of a server or a client machine in a client-server network environment, or as a peer machine in a peer-to-peer (or distributed) network environment. In embodiments, the machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computer system 3600 includes a processing device 3602, a main memory 3604 (e.g., read-only memory (ROM), flash memory, dynamic random access memory (DRAM) such as synchronous DRAM (SDRAM), a static memory 3606 (e.g., flash memory, static random access memory (SRAM), etc.), and a secondary memory 3616 (e.g., a data storage device), which communicate with each other via a bus 3608.

The processing device 3602 represents one or more general-purpose processors such as a microprocessor, central processing unit, or the like. The term "processing device" is used herein to refer to any combination of one or more integrated circuits and/or packages that include one or more processors (e.g., one or more processor cores). Therefore, the term processing device encompasses a microcontroller, a single core CPU, a multi-core CPU and a massively multi-core system that includes many interconnected integrated circuits, each of which may include multiple processor cores. The processing device 3602 may therefore include multiple processors. The processing device 3602 may include a complex instruction set computing (CISC) microprocessor, reduced instruction set computing (RISC) microprocessor, very long instruction word (VLIW) microprocessor, processor implementing other instruction sets, or processors implementing a combination of instruction sets. The processing device 3602 may also be one or more special-purpose processing devices such as an application specific integrated circuit (ASIC), a field programmable gate array (FPGA), a digital signal processor (DSP), network processor, or the like.

The computer system 3600 may further include one or more network interface devices 3622 (e.g., NICs). The computer system 3600 also may include a video display unit 3610 (e.g., a liquid crystal display (LCD) or a cathode ray tube (CRT)), an alphanumeric input device 3612 (e.g., a keyboard), a cursor control device 3614 (e.g., a mouse), and a signal generation device 3620 (e.g., a speaker).

The secondary memory 3616 may include a machine-readable storage medium (or more specifically a computer-readable storage medium) 3624 on which is stored one or more sets of instructions 3654 embodying any one or more of the methodologies or functions described herein. The instructions 3654 may also reside, completely or at least partially, within the main memory 3604 and/or within the processing device 3602 during execution thereof by the computer system 3600; the main memory 3604 and the processing device 3602 also constituting machine-readable storage media.

While the computer-readable storage medium 3624 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine that cause the machine to perform any one or more of the methodologies of the present embodiments. The term "computer-readable storage medium" shall accordingly be taken to include, but not be limited to, non-transitory media such as solid-state memories, and optical and magnetic media.

The modules, components and other features described herein can be implemented as discrete hardware components or integrated in the functionality of hardware components such as ASICS, FPGAs, DSPs or similar devices. In addition, the modules can be implemented as firmware or functional circuitry within hardware devices. Further, the modules can be implemented in any combination of hardware devices and software components, or only in software.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "measuring", "storing", "transforming", "detecting", "sensing", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the required purposes, or it may comprise a general purpose computer system selectively programmed by a computer program stored in the computer system. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic disk storage media, optical storage media, flash memory devices, other type of machine-accessible storage media, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear as set forth in the description above. In addition, the present embodiments are not described with reference to any particular programming language. It will be appreciated that a variety of programming languages may be used to implement the teachings of the embodiments as described herein.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims may generally be construed to mean "one or more" unless specified otherwise or clear from context to be directed to a singular form. Moreover, use of the term "an embodiment" or "one embodiment" or "an embodiment" or "one embodiment" throughout is not intended to mean the same embodiment or embodiment unless described as such. The terms "first," "second," "third," "fourth," etc. as used herein are meant as labels to distinguish among different elements and may not necessarily have an ordinal meaning according to their numerical designation.

It is to be understood that the above description is intended to be illustrative, and not restrictive. Many other embodiments will be apparent to those of skill in the art upon reading and understanding the above description. Although the present embodiments has been described with reference to specific examples, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A system comprising:
    a first force sensing region of footwear, wherein the first force sensing region comprises a first array of force sensor units at least partially embedded in the footwear, the first array of force sensor units comprising:
        a plurality of compliant capacitors disposed in a first plane, wherein the plurality of compliant capacitors each comprise a compliant dielectric layer disposed parallel to the first plane and between a first electrode and a second electrode; and
        a plurality of strain transformation structures coupled to the plurality of compliant capacitors, each of the plurality of strain transformation structures comprising:
            a first transformation element coupled to an outer surface of the first electrode of at least one of the plurality of compliant capacitors; and
            a second transformation element coupled to an outer surface of the second electrode of the at least one of the plurality of compliant capacitors, wherein a compressive force perpendicular to the first plane applied to the coupled strain transformation structure by a human foot induces a substantially linear change in a capacitance of the coupled compliant capacitors, and wherein the change in capacitance of the coupled compliant capacitors is indicative of the compressive force applied by the human foot to the first force sensing region of the footwear;
    a second force sensing region of the footwear, spatially distinct from the first force sensing region, wherein the second force sensing region comprises a second array of force sensor units at least partially embedded in the footwear, the second array of force sensor units comprising:
        a plurality of compliant capacitors disposed in the first plane, wherein the plurality of compliant capacitors each comprise a compliant dielectric layer disposed parallel to the first plane and between a first electrode and a second electrode; and
        a plurality of strain transformation structures coupled to the plurality of compliant capacitors, each of the plurality of strain transformation structures comprising:
            a first transformation element coupled to an outer surface of the first electrode of at least one of the plurality of compliant capacitors; and
            a second transformation element coupled to an outer surface of the second electrode of the at least one of the plurality of compliant capacitors, wherein a compressive force perpendicular to the first plane applied to the coupled strain transformation structure by a human foot induces a substantially linear change in a capacitance of the coupled compliant capacitors, and wherein the change in capacitance of the coupled compliant capacitors is indicative of the compressive force applied by the human foot to the second force sensing region of the footwear;
    a volume reduction structure that at least partially surrounds the plurality of strain transformation structures; and
    a reinforcement structure to at least partially surround the first force sensing region.

2. The system of claim 1, wherein the first force sensing region is at least partially embedded in an insole of the footwear.

3. The system of claim 1, wherein the plurality of compliant capacitors in the first array of force sensing units are electrically connected in parallel.

4. The system of claim 1, further comprising a third force sensing region of the footwear, spatially distinct from the first force sensing region and the second force sensing region, wherein the third force sensing region comprises a third array of force sensor units at least partially embedded in the footwear, the third array of force sensor units comprising:
  a plurality of compliant capacitors disposed in the first plane, wherein the plurality of compliant capacitors each comprise a compliant dielectric layer disposed parallel to the first plane and between a first electrode and a second electrode; and
  a plurality of strain transformation structures coupled to the plurality of compliant capacitors, each of the plurality of strain transformation structures comprising:
    a first transformation element coupled to an outer surface of the first electrode of at least one of the plurality of compliant capacitors; and
    a second transformation element coupled to an outer surface of the second electrode of the at least one of the plurality of compliant capacitors, wherein a compressive force perpendicular to the first plane applied to the coupled strain transformation structure by a human foot induces a substantially linear change in a capacitance of the coupled compliant capacitors, and wherein the change in capacitance of the coupled compliant capacitors is indicative of the compressive force applied by the human foot to the third force sensing region of the footwear.

5. The system of claim 1, wherein the first force sensing region and the second force sensing region are offset and reflected about a center axis in opposite directions, wherein the center axis is parallel to the first plane.

6. The system of claim 1, further comprising:
  a capacitance measuring circuit coupled to the first force sensing region of the footwear, wherein the capacitance measuring circuit to generate data indicative of the capacitance associated with the first force sensor unit;
  a transceiver coupled to the capacitance measuring circuit; and
  an antenna coupled to the transceiver to transmit to a user device the data indicative of the capacitance associated with the first force sensor unit.

7. An apparatus, comprising:
  a first array of force sensor units comprising:
    a plurality of compliant capacitors disposed in a first plane, wherein the plurality of compliant capacitors each comprise a compliant dielectric layer disposed parallel to the first plane and between a first electrode and a second electrode; and
    a plurality of strain transformation structures coupled to the plurality of compliant capacitors, each of the plurality of strain transformation structures comprising:
      a first transformation element coupled to an outer surface of the first electrode of at least one of the plurality of compliant capacitors;
      a second transformation element coupled to an outer surface of the second electrode of the at least one of the plurality of compliant capacitors, wherein a compressive force perpendicular to the first plane and applied to the coupled strain transformation structure induces a substantially linear change in a capacitance of the coupled compliant capacitor; and
    a volume reduction structure that at least partially surrounds the plurality of strain transformation structures.

8. The apparatus of claim 7, wherein the compressive force perpendicular to the first plane and applied to the coupled strain transformation structure induces a deformation of a surface of the coupled strain transformation structure that is parallel to the first plane, wherein the deformation of the coupled strain transformation structure is substantially linear to the compressive force and induces a substantially linear change in area of the coupled compliant capacitor.

9. The apparatus of claim 7, wherein a volume of the volume reduction structure is configured to decrease responsive to a lateral deformation of at least one of the plurality of strain transformation structures that is parallel to the first plane.

10. The apparatus of claim 7, wherein the volume reduction structure is a compressible material.

11. The apparatus of claim 7, further comprising a reinforcement structure coupled to the first array of force sensor units, wherein the reinforcement structure is configured to provide rigidity to the first array of force sensor units.

12. The apparatus of claim 7, wherein at least one of the plurality of compliant capacitors of the first array of force sensor units further comprises a third electrode disposed between the first electrode and the second electrode, wherein the third electrode is disposed parallel to the first plane, and wherein at least one of the first electrode or the second electrode is to couple to a ground voltage potential.

13. The apparatus of claim 7, wherein the first transformation element and the second transformation element are an incompressible material.

14. The apparatus of claim 7, wherein the first transformation element and the second transformation element are a same material.

15. The apparatus of claim 7, wherein the first transformation element and the second transformation element are a same geometric shape.

16. The apparatus of claim 7, wherein the first transformation element and the second transformation element are aligned along an axis perpendicular to the first plane.

17. The apparatus of claim 7, further comprising a second array of force sensor units, wherein the first array of force sensor units and the second array of force sensor units are coupled in parallel.

18. The apparatus of claim 17, wherein the first array of force sensor units and the second array of force sensor units are offset and reflected about a center axis in opposite directions, wherein the center axis is parallel the first plane.

* * * * *